US008703305B2

(12) United States Patent
Egawa et al.

(10) Patent No.: US 8,703,305 B2
(45) Date of Patent: Apr. 22, 2014

(54) QUINOXALINE DERIVATIVE, AND LIGHT EMITTING ELEMENT, LIGHT EMITTING DEVICE, AND ELECTRONIC DEVICE USING THE QUINOXALINE DERIVATIVE

(75) Inventors: Masakazu Egawa, Tochigi (JP); Satoshi Seo, Kanagawa (JP); Nobuharu Ohsawa, Kanagawa (JP)

(73) Assignee: Semiconductor Energy Laboratory Co., Ltd. (JP)

( * ) Notice: Subject to any disclaimer, the term of this patent is extended or adjusted under 35 U.S.C. 154(b) by 0 days.

(21) Appl. No.: 13/459,981

(22) Filed: Apr. 30, 2012

(65) Prior Publication Data

US 2012/0242936 A1 Sep. 27, 2012

Related U.S. Application Data

(63) Continuation of application No. 11/859,422, filed on Sep. 21, 2007, now abandoned.

(30) Foreign Application Priority Data

Sep. 29, 2006 (JP) .................................. 2006-270084

(51) Int. Cl.
*C07D 403/14* (2006.01)
*G02F 1/13357* (2006.01)
*H01L 51/54* (2006.01)

(52) U.S. Cl.
USPC ........ 428/690; 428/411.1; 428/917; 548/440; 549/456

(58) Field of Classification Search
None
See application file for complete search history.

(56) References Cited

U.S. PATENT DOCUMENTS

| | | | |
|---|---|---|---|
| 2005/0123791 A1* | 6/2005 | Deaton et al. | 428/690 |
| 2005/0186446 A1* | 8/2005 | Shitagaki et al. | 428/690 |
| 2008/0079354 A1* | 4/2008 | Egawa et al. | 313/503 |
| 2012/0313506 A1* | 12/2012 | Egawa et al. | 313/502 |

FOREIGN PATENT DOCUMENTS

| | | |
|---|---|---|
| EP | 1 616 864 A1 | 1/2006 |
| JP | 2003-40873 | 2/2003 |
| WO | WO 2004-094389 A1 | 11/2004 |

OTHER PUBLICATIONS

Tang, C.W. et al, "Organic Electroluminescent Diodes," Applied Physics Letters, vol. 51, No. 12, Sep. 21, 1987, pp. 913-915.
Adachi, C. et al, "Electroluminescence in Organic Films with Three-Layer Structure," Japanese Journal of Applied Physics, vol. 27, No. 2, 1988, pp. L269-L271.
Hirayama, T. et al, "Fluorescent Solvatochromism of Bi-Polar N,N-diphenylaminoaryl-Substituted Hexaazatriphenylenes, Tetraazaphenanthrene, and Quinoxalines," Dyes and Pigments, vol. 67, 2005, pp. 105-110.

* cited by examiner

*Primary Examiner* — Jennifer Chriss
*Assistant Examiner* — J. L. Yang
(74) *Attorney, Agent, or Firm* — Husch Blackwell LLP

(57) ABSTRACT

To provide a new bipolar organic compound. In particular, to provide a bipolar organic compound having excellent heat resistance and to provide a bipolar organic compound which is electrochemically stable. Further, to provide a light emitting element and a light emitting device of which a driving voltage and power consumption are reduced by using a new bipolar organic compound. Further, to provide a light emitting element and a light emitting device which have excellent heat resistance by using a new bipolar organic compound. Further, to provide a light emitting element and a light emitting device which have a long life by using a new bipolar organic compound.

20 Claims, 35 Drawing Sheets

QUINOXALINE DERIVATIVE, AND LIGHT EMITTING ELEMENT, LIGHT EMITTING DEVICE, AND ELECTRONIC DEVICE USING THE QUINOXALINE DERIVATIVE

This application is a continuation of application Ser. No. 11/859,422 filed on Sep. 21, 2007 now abandoned.

BACKGROUND OF THE INVENTION

1. Field of the Invention

The present invention relates to a quinoxaline derivative, and a light emitting element, a light emitting device, and an electronic device each of which uses the quinoxaline derivative.

2. Description of the Related Art

An organic compound has various material systems compared with an inorganic compound, and has possibility to synthesize materials having various functions depending on the molecular design. Owing to these advantages, photo electronics and electronics which use a functional organic material have been attracting attention in recent years.

For example, a solar cell, a light emitting element, an organic transistor, and the like can be given as examples of an electronic device using an organic compound as a functional organic material. These are devices that take advantage of electric properties and optical properties of the organic compound. Of these, a light emitting element has, in particular, shown remarkable development.

It is said that a light emission mechanism of a light emitting element is as follows: by applying a voltage between a pair of electrodes which interpose a light emitting layer, electrons injected from a cathode and holes injected from an anode are recombined in the luminescent center of the light emitting layer so as to form molecular excitons, and energy is released to emit light when the molecular excitons return to a ground state. As excitation states, a singlet excitation state and a triplet excitation state are known, and it is thought that light emission can be obtained through either of these excitation states.

Such a light emitting element has a lot of problems depending on its material in the case where an element property thereof is improved. In order to solve the problems, improvement of element structure, development of materials, and the like have been carried out.

As the most basic structure of a light emitting element, the following structure is known: a hole transporting layer formed of an organic compound having a hole transporting property and an electron transporting light emitting layer formed of an organic compound having an electron transporting property are stacked to form a thin film approximately 100 nm thick in total, and this thin film is interposed between electrodes (e.g., Non-Patent Document 1: C. W. Tang and one other, *Applied Physics Letters*, vol. 51, No. 12, 913-915 (1987)).

By applying a voltage to the light emitting element described in Non-Patent Document 1, light emission can be obtained from an organic compound having a light emitting property and an electron transporting property.

Further, in the light emitting element described in Non-Patent Document 1, functional separation is carried out; that is, a hole transporting layer transports holes, and an electron transporting layer transports electrons and emits light. However, various interactions (e.g., formation of exciplexes) occur in an interface of the stacked layers. As a result, a change in the light emission spectrum or a decline in light emission efficiency may occur.

In order to decrease the amount of change in the light emission spectrum or the amount of decline in light emission efficiency which is caused by the interaction at an interface, a light emitting element in which functional separation is further carried out has been devised. For example, a light emitting element having a structure in which a light emitting layer is interposed between a hole transporting layer and an electron transporting layer has been supposed (e.g., Non-Patent Document 2: Chihaya Adachi and three others, *Japanese Journal of Applied Physics*, vol. 27, No. 2, L269-L271 (1988)).

In such a light emitting element as described in Non-Patent Document 2, the light emitting layer is preferably formed by using a bipolar organic compound which has both an electron transporting property and a hole transporting property, in order to further suppress the interaction occurring at the interface.

Most organic compounds are, however, monopolar materials in which either a hole transporting property or an electron transporting property is more pronounced than the other one.

Therefore, development of a bipolar organic compound having both an electron transporting property and a hole transporting property has been required.

In Patent Document 1 (PCT International Publication No. 2004/094389), a bipolar quinoxaline derivative has been described. However, since characteristics such as heat resistance are not high enough yet, development of more varied bipolar organic compounds has been required.

SUMMARY OF THE INVENTION

In view of the foregoing problems, an object of the present invention is to provide a new bipolar organic compound. In particular, an object of the present invention is to provide a bipolar organic compound having excellent heat resistance and to provide a bipolar organic compound which is electrochemically stable.

Further, another object is to provide a light emitting element and a light emitting device of which a driving voltage and power consumption are reduced by using the bipolar organic compound of the present invention. Further, another object is to provide a light emitting element and a light emitting device which have excellent heat resistance by using the bipolar organic compound of the present invention. Further, another object is to provide a light emitting element and a light emitting device which have a long life by using the bipolar organic compound of the present invention.

Still another object is to provide an electronic device in which power consumption is reduced by using the bipolar organic compound of the present invention. Further, another object is to provide an electronic device having excellent heat resistance. Further, another object is to provide a long-life electronic device.

One mode of the present invention is a quinoxaline derivative represented by the general formula (1).

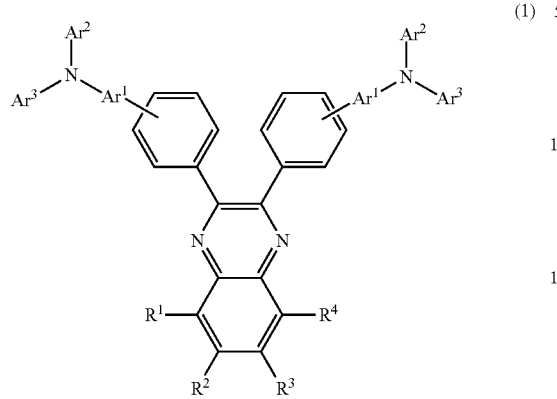

(1)

(In the formula, $R^1$ to $R^4$ may be the same or different and each represent any one of a hydrogen atom, an alkyl group of carbon number 1 to 4, and an aryl group of carbon number 6 to 25. $R^1$, $R^2$, and $R^3$ may bond to $R^2$, $R^3$, and $R^4$, respectively, to form a condensed ring. $Ar^1$ represents an arylene group of carbon number 6 to 25. $Ar^2$ and $Ar^3$ may be the same or different and each represent an arylene group of carbon number 6 to 25. $Ar^1$ and $Ar^2$ may bond to $Ar^2$ and $Ar^3$, respectively.)

Another mode of the present invention is a quinoxaline derivative represented by the general formula (2).

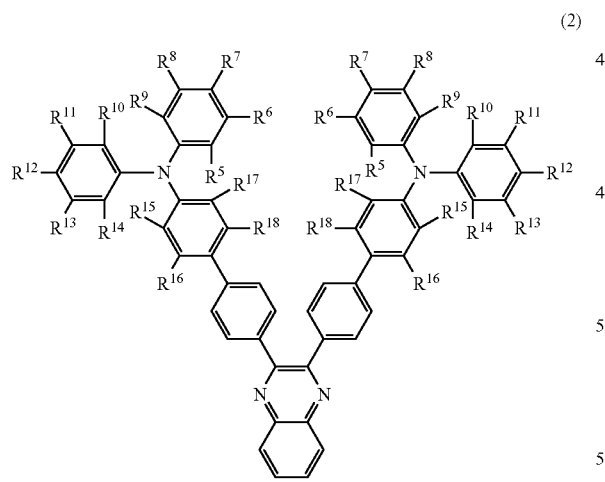

(2)

(In the formula, $R^5$ to $R^{18}$ may be the same or different and each represent any one of a hydrogen atom, an alkyl group of carbon number 1 to 4, and an aryl group of carbon number 6 to 15. $R^5$, $R^6$, $R^7$, $R^8$, $R^{10}$, $R^{11}$, $R^{12}$, $R^{13}$, $R^{15}$, and $R^{17}$ may bond to $R^6$, $R^7$, $R^8$, $R^9$, $R^{11}$, $R^{12}$, $R^{13}$, $R^{14}$, $R^{16}$, and $R^{18}$, respectively, to form a condensed ring.)

Another mode of the present invention is a quinoxaline derivative represented by the general formula (3).

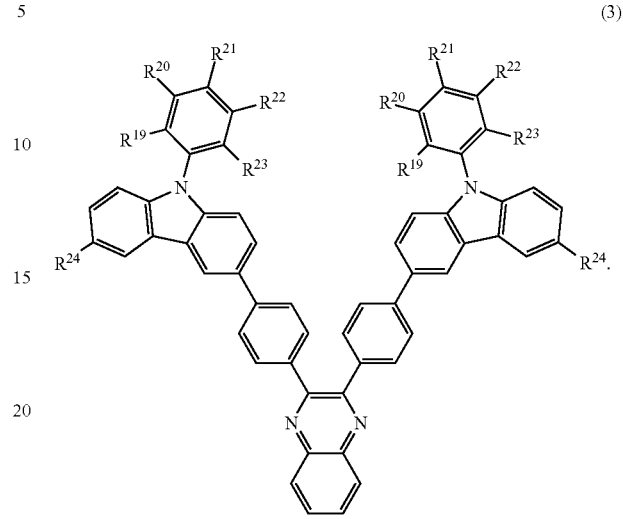

(3)

(In the formula, $R^{19}$ to $R^{24}$ may be the same or different and each represent any one of a hydrogen atom, an alkyl group of carbon number 1 to 4, and an aryl group of carbon number 6 to 15. $R^{19}$, $R^{20}$, $R^{21}$, and $R^{22}$ may bond to $R^{20}$, $R^{21}$, $R^{22}$, and $R^{23}$, respectively, to form a condensed ring.)

Another mode of the present invention is a quinoxaline derivative represented by the general formula (4).

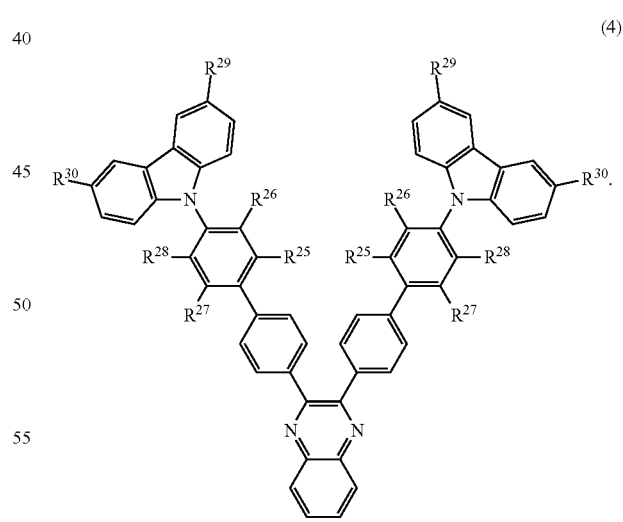

(4)

(In the formula, $R^{25}$ to $R^{30}$ may be the same or different and each represent any one of a hydrogen atom, an alkyl group of carbon number 1 to 4, and an aryl group of carbon number 6 to 15. $R^{25}$ and $R^{27}$ may bond to $R^{26}$ and $R^{28}$, respectively, to form a condensed ring.)

Another mode of the present invention is a quinoxaline derivative represented by the structural formula (11).

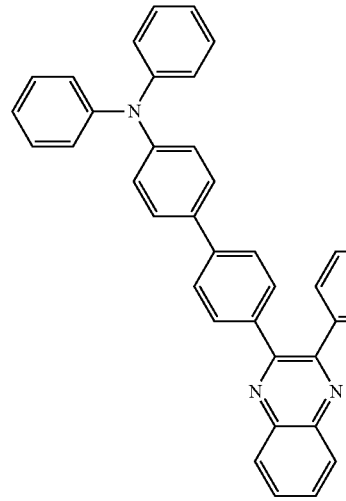

(11)

Another mode of the present invention is a quinoxaline derivative represented by the structural formula (12).

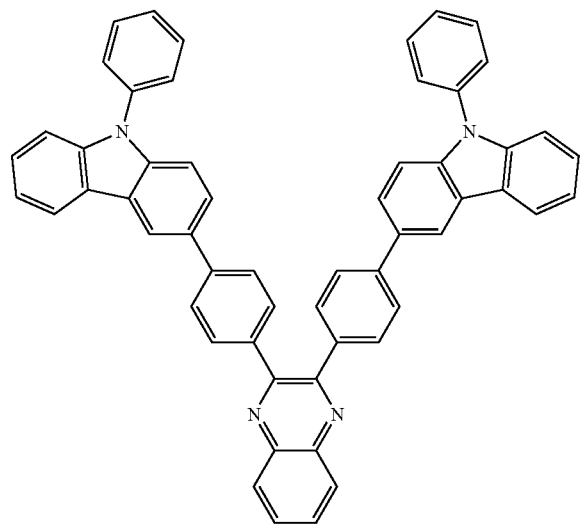

(12)

Another mode of the present invention is a quinoxaline derivative represented by the structural formula (13).

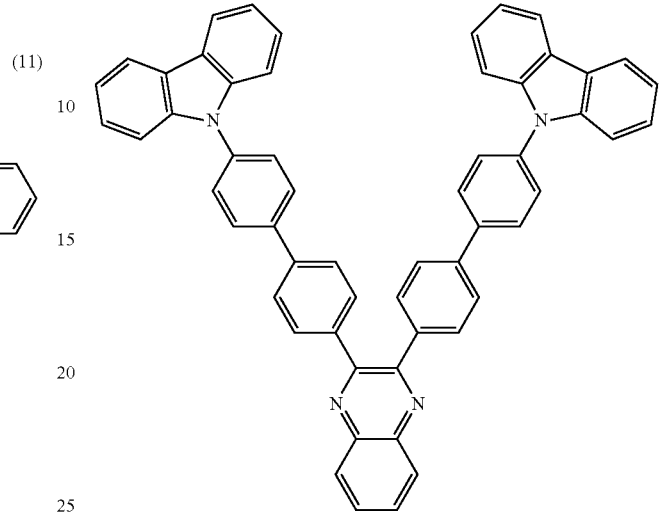

(13)

Another mode of the present invention is a light emitting element using the aforementioned quinoxaline derivative; specifically, a light emitting element in which the aforementioned quinoxaline derivative is provided between a pair of electrodes.

Another mode of the present invention is a light emitting element in which a light emitting layer is provided between a pair of electrodes and the light emitting layer contains the aforementioned quinoxaline derivative.

Another mode of the present invention is a light emitting element in which a light emitting layer is provided between a pair of electrodes and the light emitting layer contains the aforementioned quinoxaline derivative and a fluorescent material.

Another mode of the present invention is a light emitting element in which a light emitting layer is provided between a pair of electrodes and the light emitting layer contains the quinoxaline derivative and a phosphorescent material.

In the above-described structure, it is preferable that a light emission spectrum of the phosphorescent material have a peak at 560 nm to 700 nm (both inclusive).

The light emitting device of the present invention includes: between a pair of electrodes, a light emitting element containing the above-described quinoxaline derivative and a control means for controlling light emission of the light emitting element. It is to be noted that a "light emitting device" in this specification includes in its category, an image displaying device, a light emitting device, or a light source (including a lighting device). In addition, it also includes a module in which a connector such as an FPC (Flexible Printed Circuit), a TAB (Tape Automated Bonding) tape, or a TCP (Tape Carrier Package) is attached to a panel, a module in which a printed wiring board is mounted on the tip of a TAB tape or a TCP, and a module in which an IC (integrated circuit) is directly mounted on a light emitting element by COG (Chip On Glass).

Further, an electronic device using the light emitting element of the present invention for its display portion is included in the category of the present invention. Therefore, the electronic device of the present invention includes a display portion provided with the aforementioned light emitting element and control means for controlling light emission of the light emitting element.

The quinoxaline derivative of the present invention is bipolar and excellent in both electron transporting property and hole transporting property. Further, the quinoxaline derivative of the present invention has a high glass transition point and excellent heat resistance. Further, the quinoxaline derivative of the present invention is stable with respect to electrochemical oxidation or reduction.

By using the quinoxaline derivative of the present invention, which is bipolar, a light emitting element and a light emitting device in which a driving voltage is low and power consumption is low can be obtained.

Further, by using the quinoxaline derivative of the present invention, which has a high glass transition point, a light emitting element and a light emitting device which have high heat resistance can be obtained.

Further, by using the quinoxaline derivative of the present invention, which is stable with respect to electrochemical oxidation or reduction, a long-life light emitting element and a long-life light emitting device can be obtained.

Further, by using the quinoxaline derivative of the present invention, an electronic device in which power consumption is low. Further, an electronic device which has high heat resistance can be obtained. Further, a long-life electronic device can be obtained.

DETAILED DESCRIPTION OF THE INVENTION

Figure 1A:
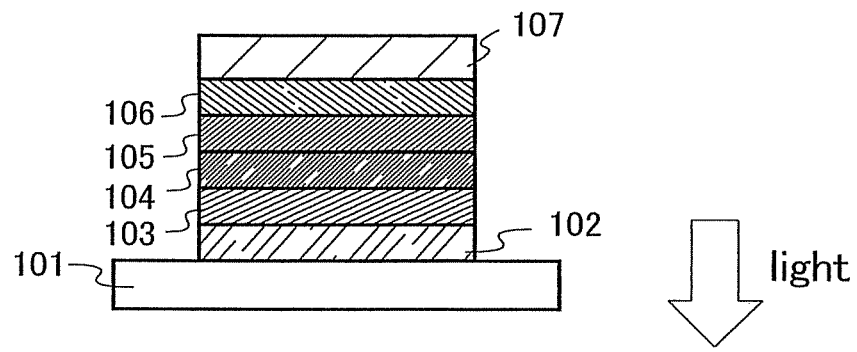
FIGS. 1A to 1C are diagrams each showing a light emitting element of the present invention.

Although the present invention will be fully described by way of embodiment modes and embodiments with reference to the accompanying drawings, it is to be understood that various changes and modifications will be apparent to those skilled in the art. Therefore, unless such changes and modifications depart from the spirit and scope of the present invention, they should be construed as being included therein.

(Embodiment Mode 1)

A quinoxaline derivative of the present invention is represented by the general formula (1).

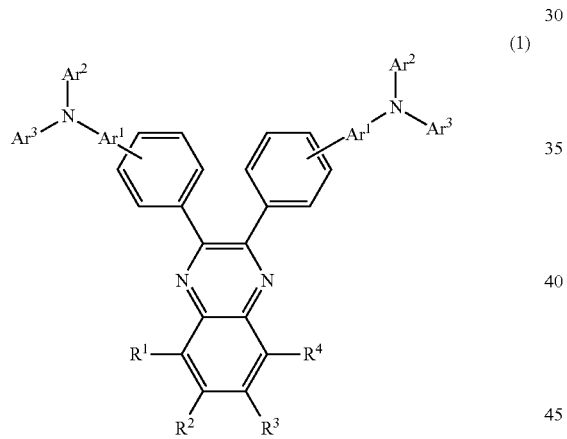

(1)

(In the formula, $R^1$ to $R^4$ may be the same or different and each represent any one of a hydrogen atom, an alkyl group of carbon number 1 to 4, and an aryl group of carbon number 6 to 25. $R^1$, $R^2$, and $R^3$ may bond to $R^2$, $R^3$, and $R^4$, respectively, to form a condensed ring. $Ar^1$ represents an arylene group of carbon number 6 to 25. $Ar^2$ and $Ar^3$ may be the same or different and each represent an arylene group of carbon number 6 to 25. $Ar^1$ and $Ar^2$ may bond to $Ar^2$ and $Ar^3$, respectively.)

In the above general formula (1), $Ar^1$ which is connected to a phenyl group may bond in any one of the ortho position, meta position, and para position on a quinoxaline skeleton.

In the above general formula (1), as examples of the alkyl group of carbon number 1 to 4, a methyl group, an ethyl group, an isopropyl group, an n-butyl group, a sec-butyl group, an isobutyl group, a tert-butyl group, and the like can be given.

Further, in the above general formula (1), as examples of the aryl group of carbon number 6 to 25, substituent groups which are represented by the structural formulae (5-1) to (5-9) can be given.

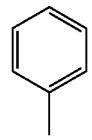

(5-1)

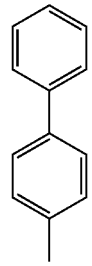

(5-2)

(5-3)

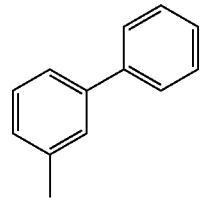

(5-4)

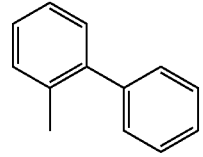

(5-5)

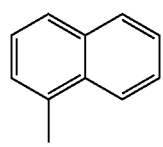

(5-6)

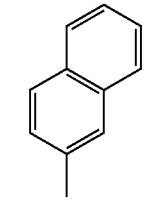

(5-7)

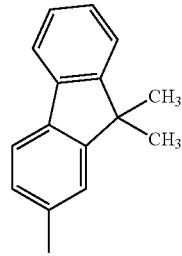

(5-8)

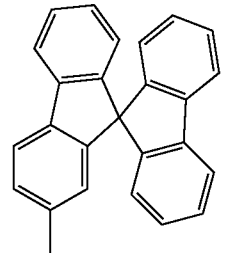

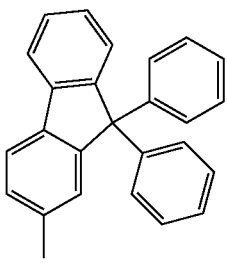
(5-9)

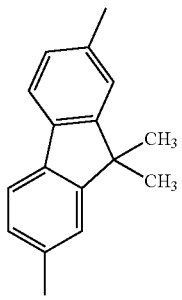
(6-7)

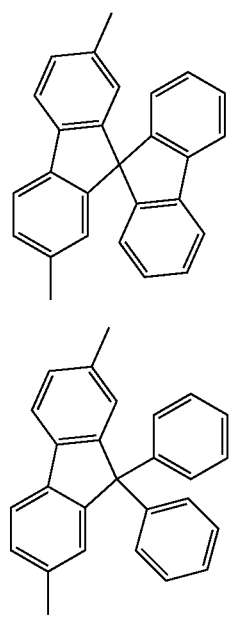
(6-8)
(6-9)

Further, in the above general formula (1), as examples of the arylene group of carbon number 6 to 25, substituent groups which are represented by the structural formulae (6-1) to (6-9) can be given.

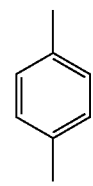
(6-1)

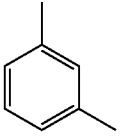
(6-2)

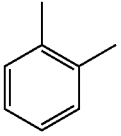
(6-3)

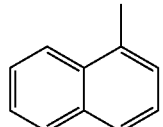
(6-4)

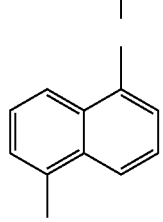
(6-5)

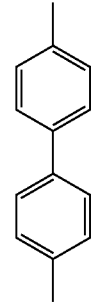
(6-6)

In the quinoxaline derivative represented by the general formula (1), the present invention is preferably a quinoxaline derivative represented by the general formula (2).

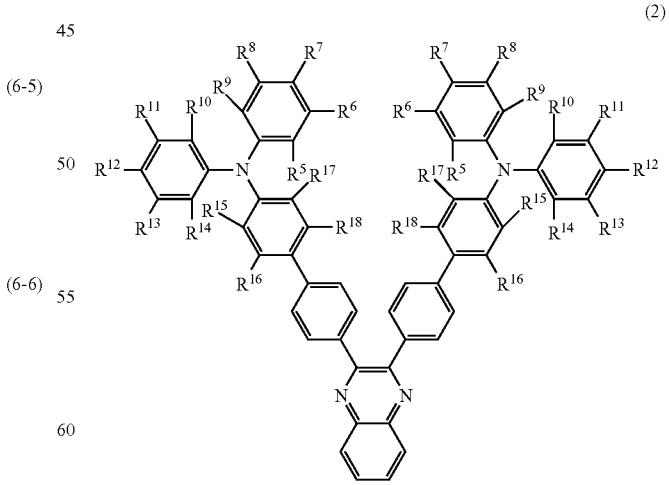
(2)

(In the formula, $R^5$ to $R^{18}$ may be the same or different and each represent any one of a hydrogen atom, an alkyl group of carbon number 1 to 4, and an aryl group of carbon number 6 to 15. $R^5$, $R^6$, $R^7$, $R^8$, $R^{10}$, $R^{11}$, $R^{12}$, $R^{13}$, $R^{15}$, and $R^{17}$ may bond to $R^6$, $R^7$, $R^8$, $R^9$, $R^{11}$, $R^{12}$, $R^{13}$, $R^{14}$, $R^{16}$, and $R^{18}$, respectively, to form a condensed ring.)

Alternatively, in the quinoxaline derivative represented by the general formula (1), the present invention is preferably a quinoxaline derivative represented by the general formula (3).

Further alternatively, in the quinoxaline derivative represented by the general formula (1), the present invention is preferably a quinoxaline derivative represented by the general formula (4).

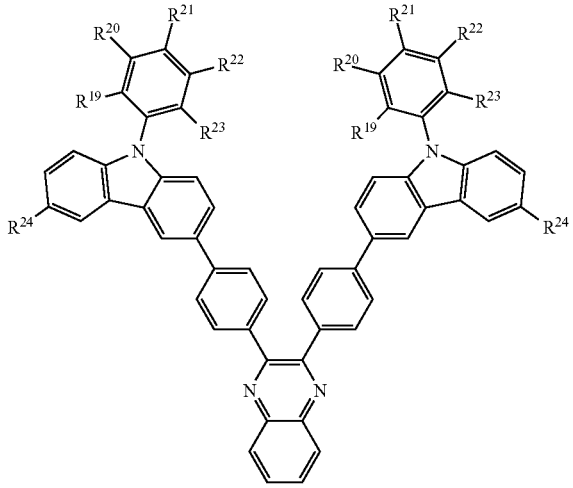

(3)

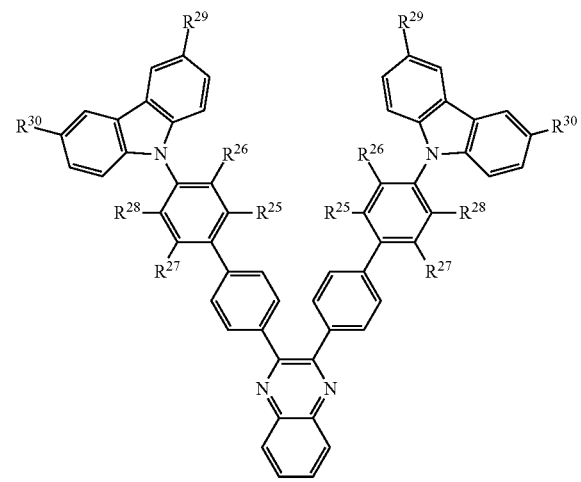

(4)

(In the formula, $R^{19}$ to $R^{24}$ may be the same or different and each represent any one of a hydrogen atom, an alkyl group of carbon number 1 to 4, and an aryl group of carbon number 6 to 15. $R^{19}$, $R^{20}$, $R^{21}$, and $R^{22}$ may bond to $R^{20}$, $R^{21}$, $R^{22}$, and $R^{23}$, respectively, to form a condensed ring.)

(In the formula, $R^{25}$ to $R^{30}$ may be the same or different and each represent any one of a hydrogen atom, an alkyl group of carbon number 1 to 4, and an aryl group of carbon number 6 to 15. $R^{25}$ and $R^{27}$ may bond to $R^{26}$ and $R^{28}$, respectively, to form a condensed ring.)

Further, as specific examples of the quinoxaline derivative of the present invention, quinoxaline derivatives represented by the structural formulae (11) to (117) can be given; however, the present invention is not limited thereto.

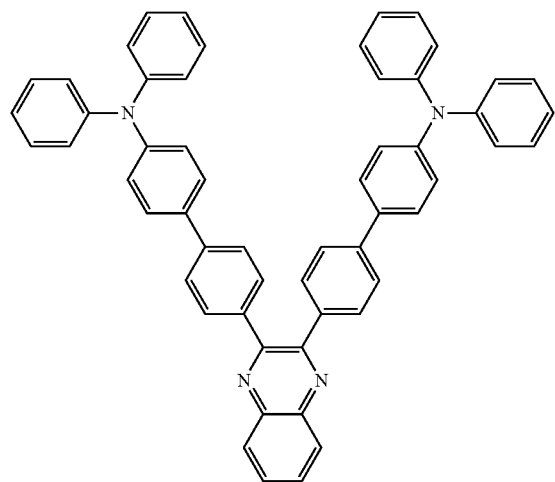

(11)

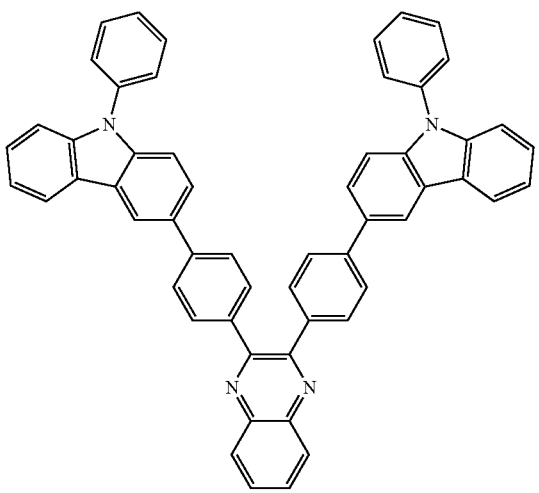

(12)

-continued
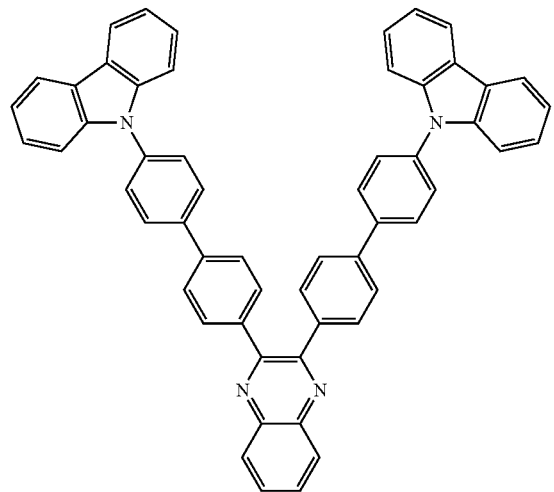
(13)
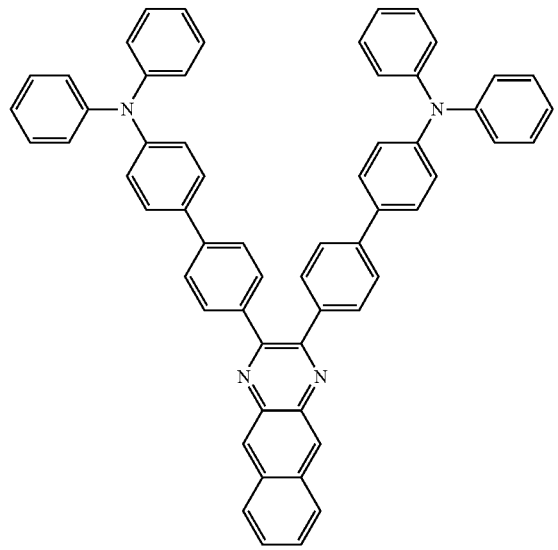
(14)
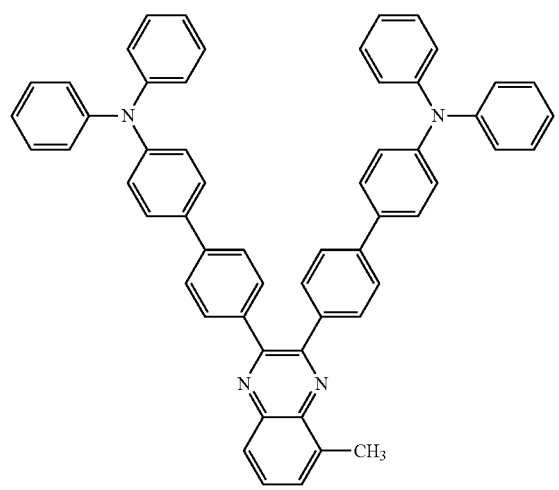
(15)
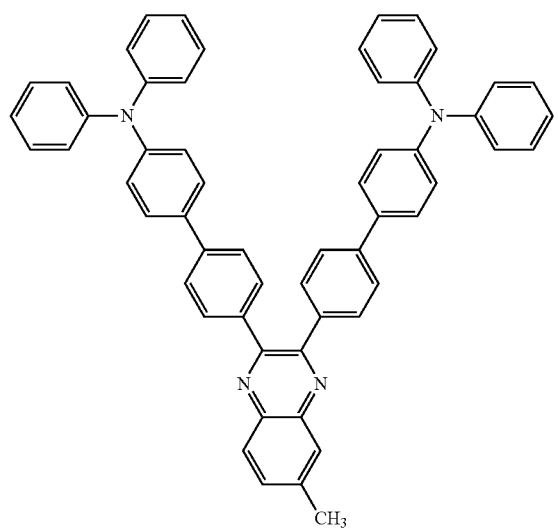
(16)
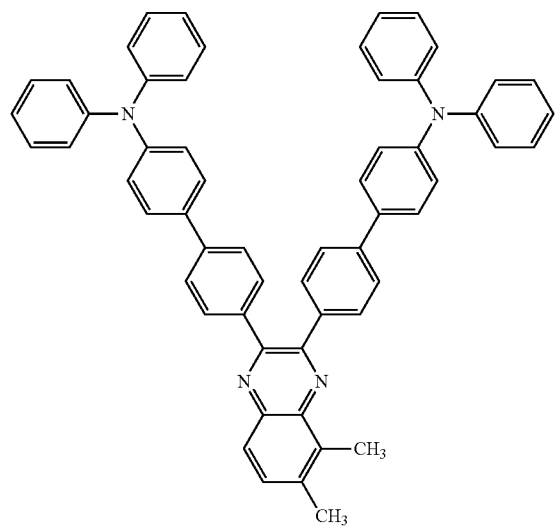
(17)
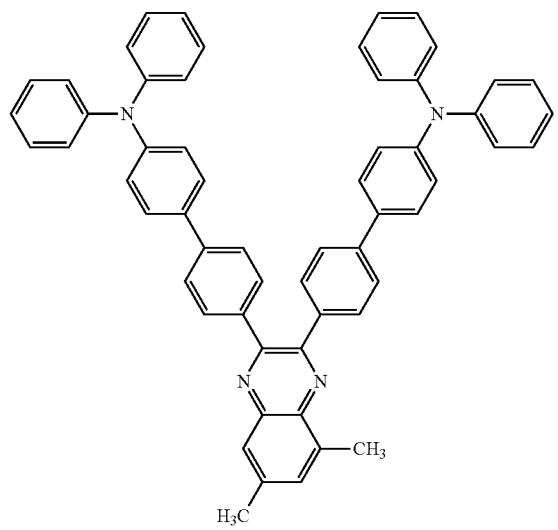
(18)

-continued
(19)
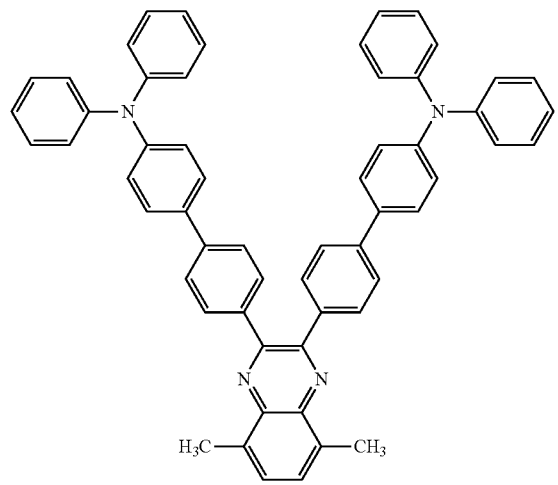
(20)
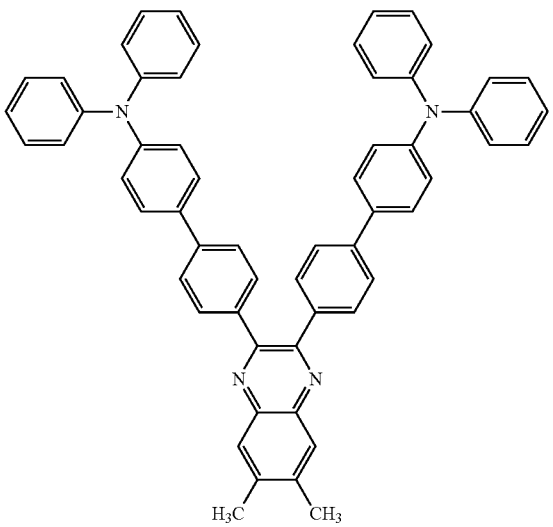
(21)
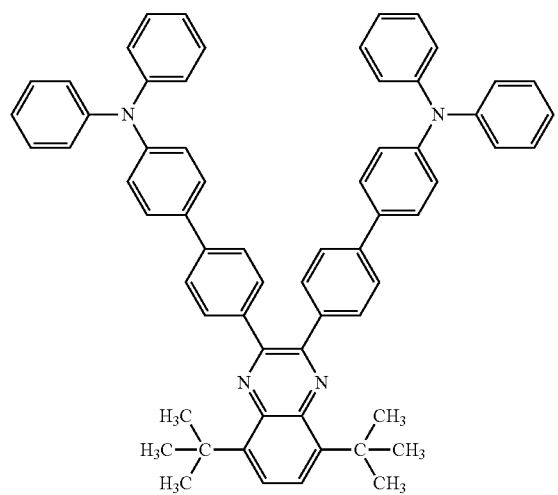
(22)
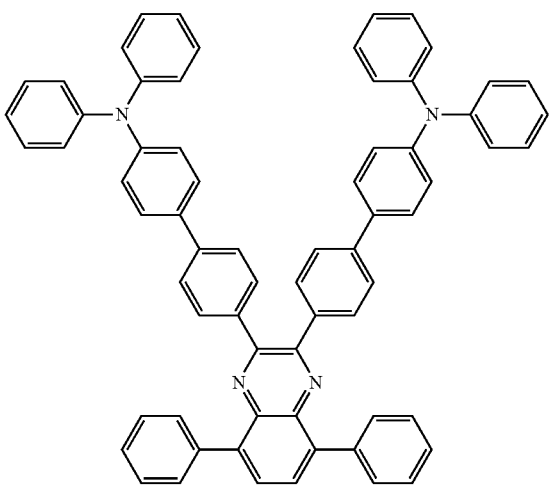
(23)
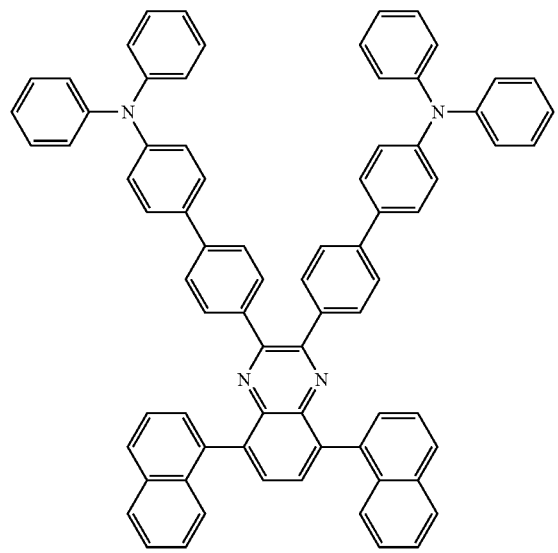
(24)
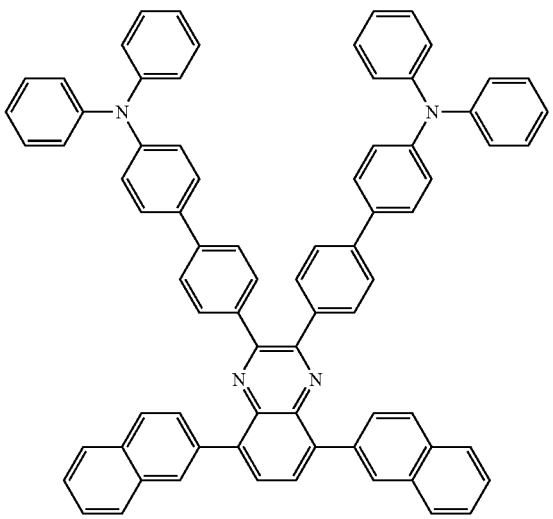

(25)
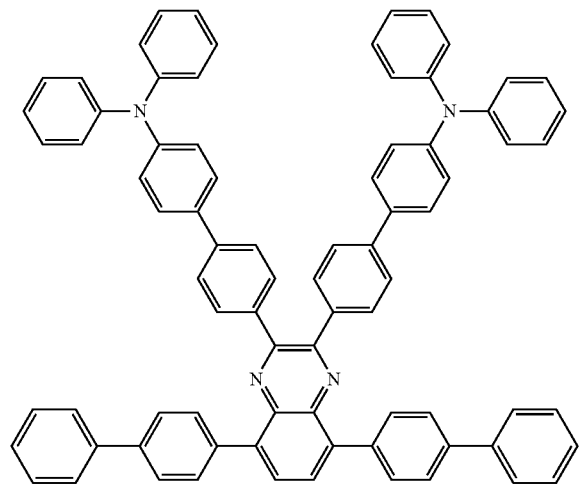
(26)
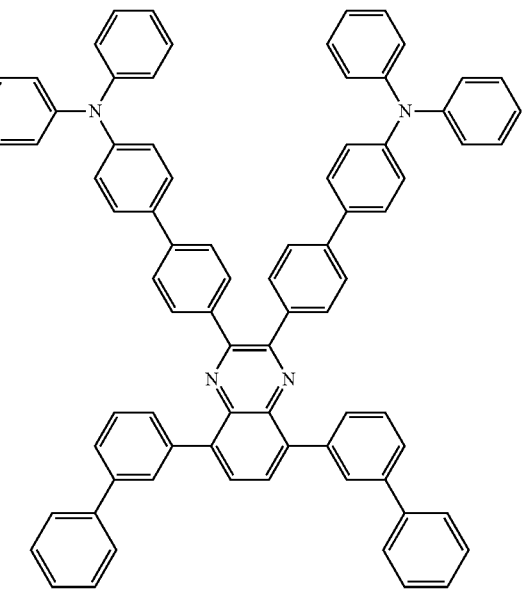
(27)
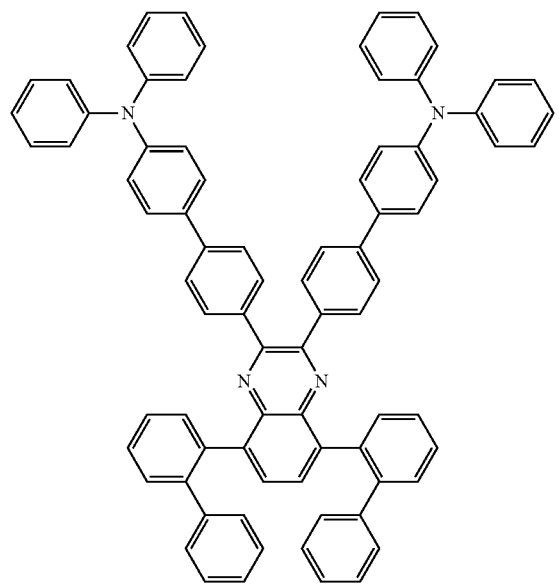
(28)
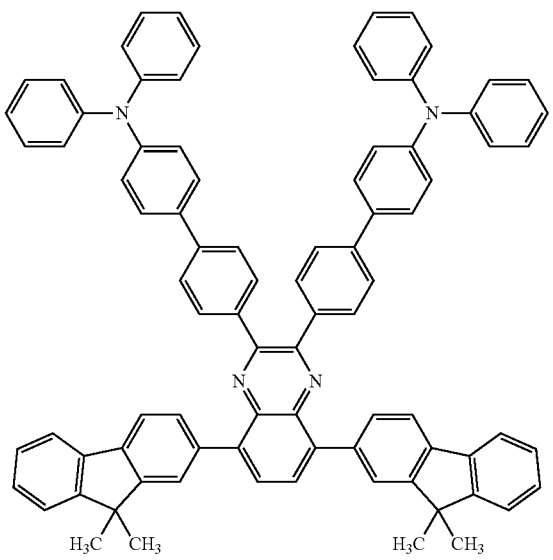

-continued
(29)
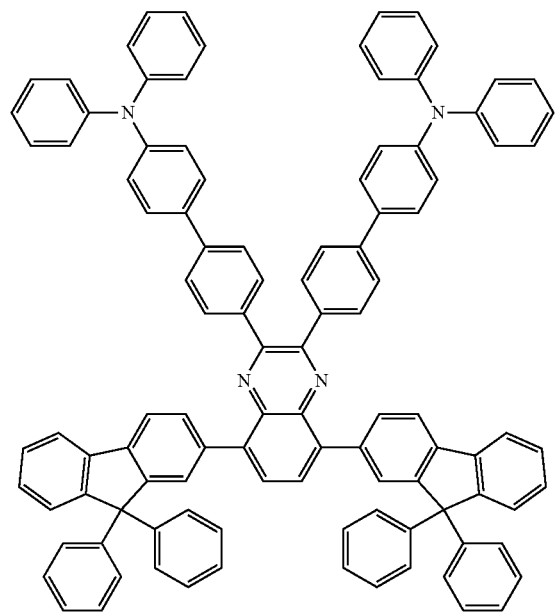
(30)
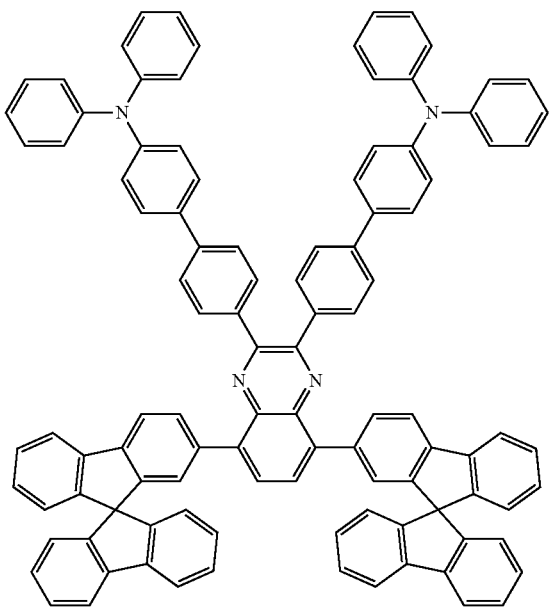
(31)
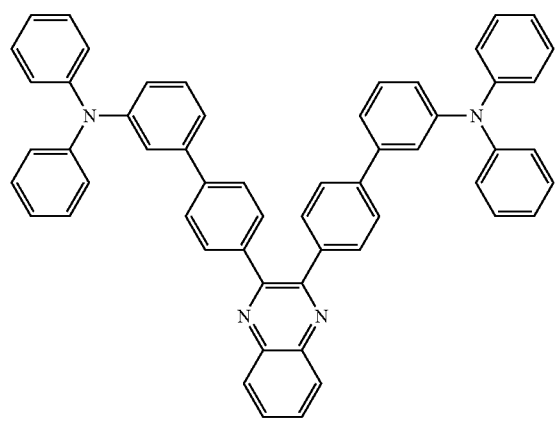
(32)
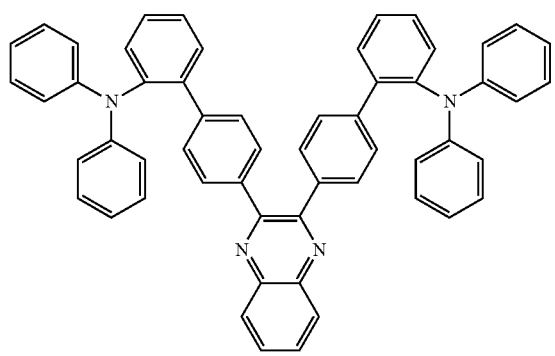
(33)
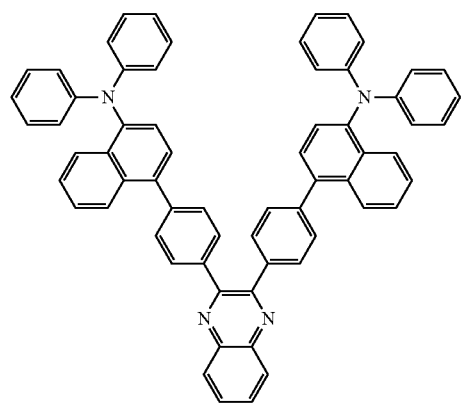
(34)
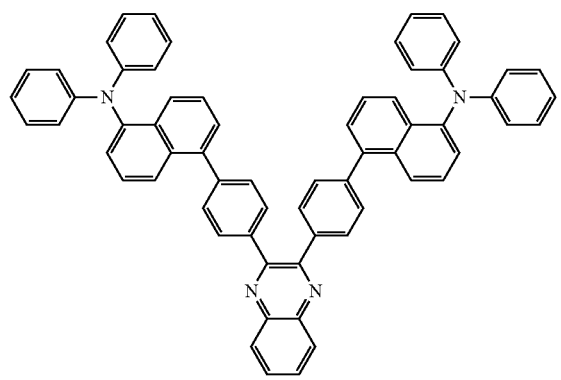

(35)
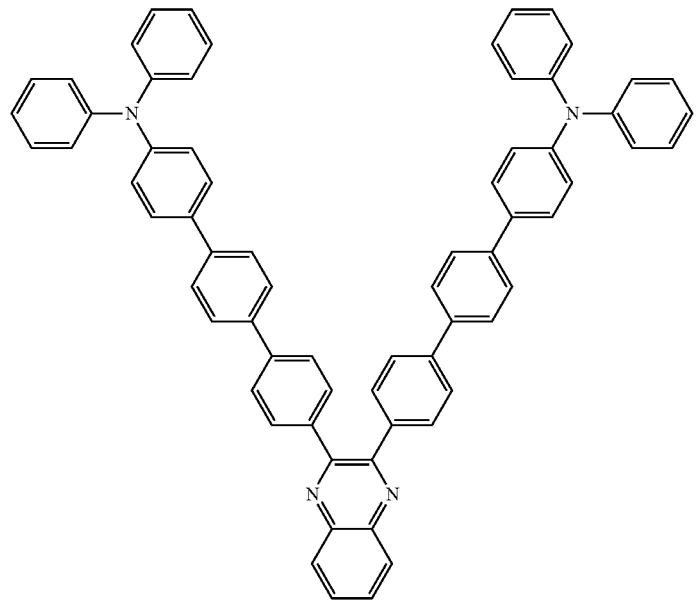
(36)
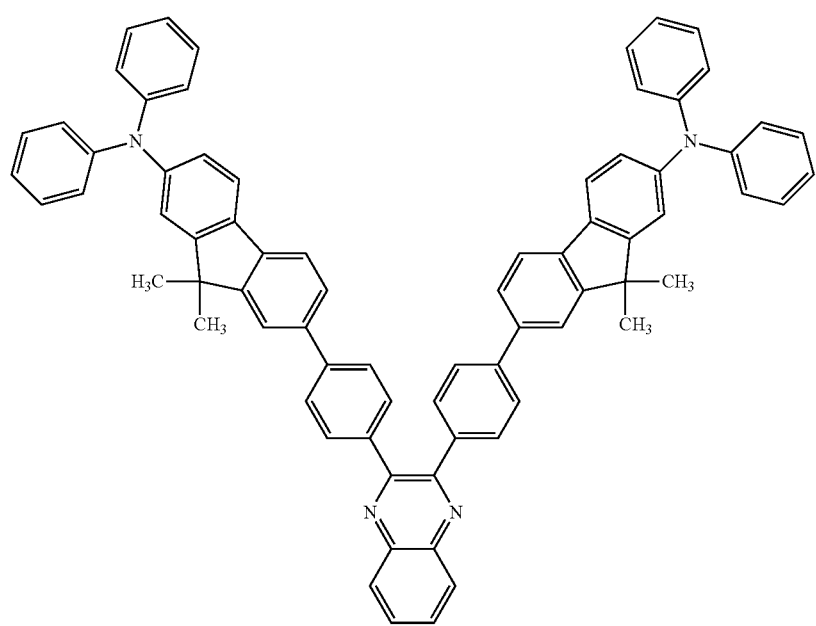

-continued
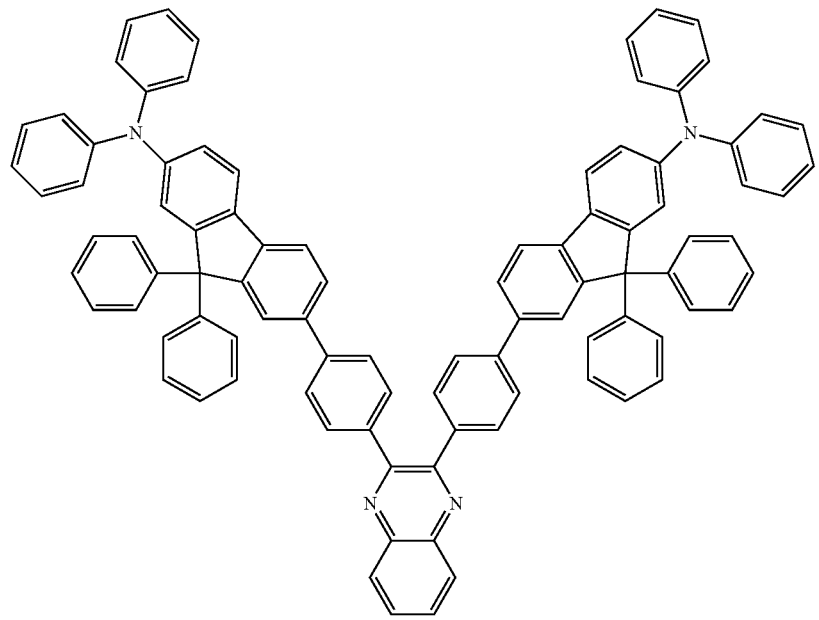
(37)
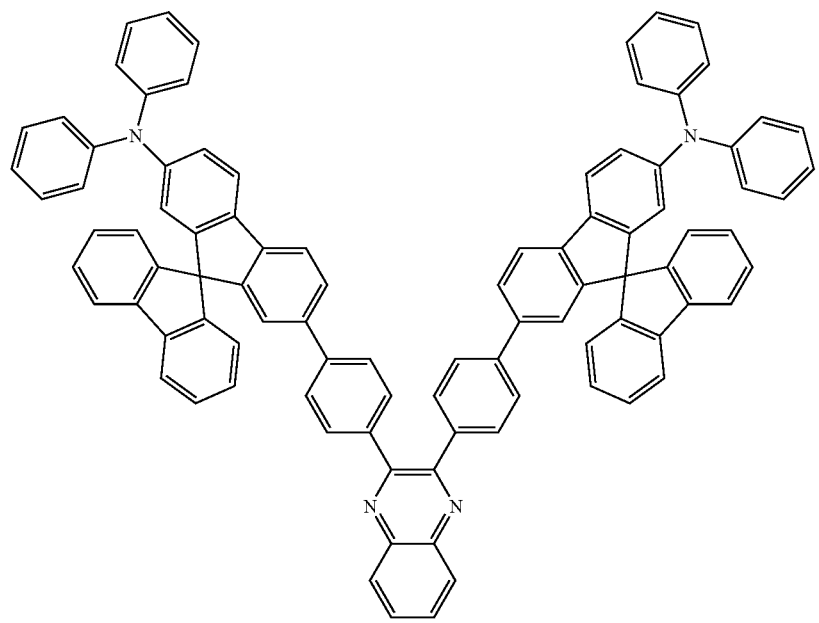
(38)
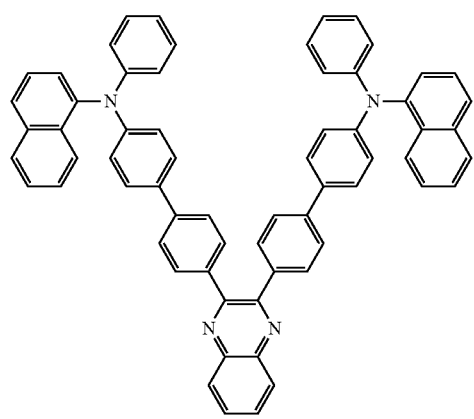
(39)
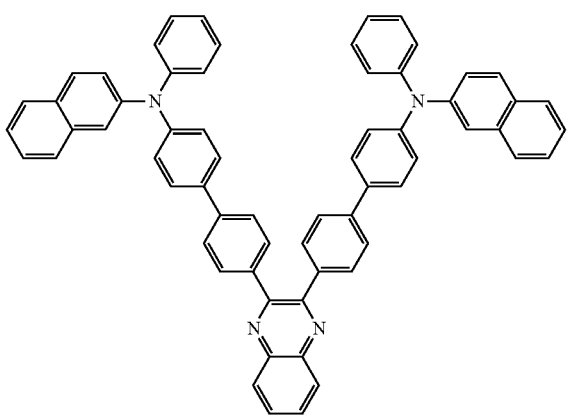
(40)

-continued
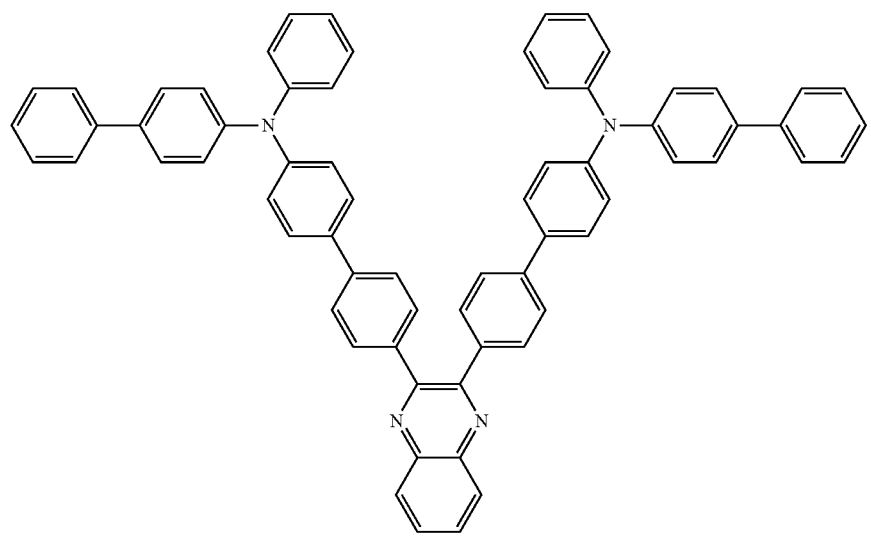
(41)
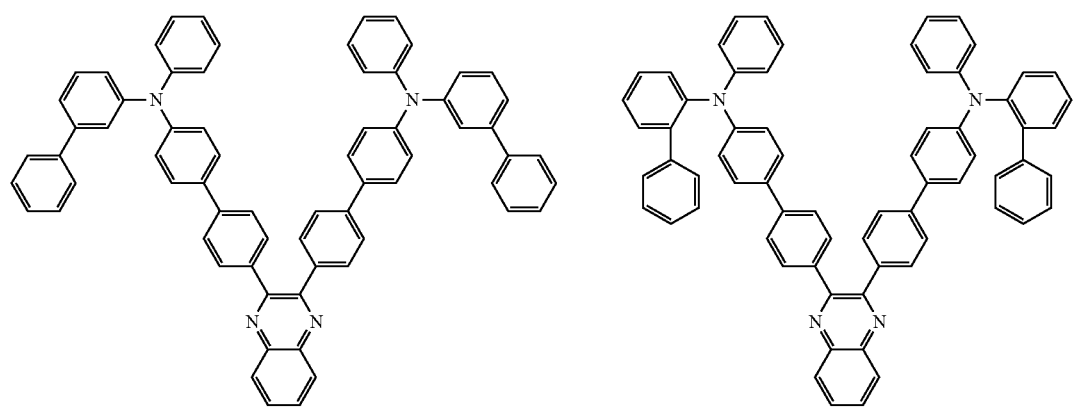
(42) (43)
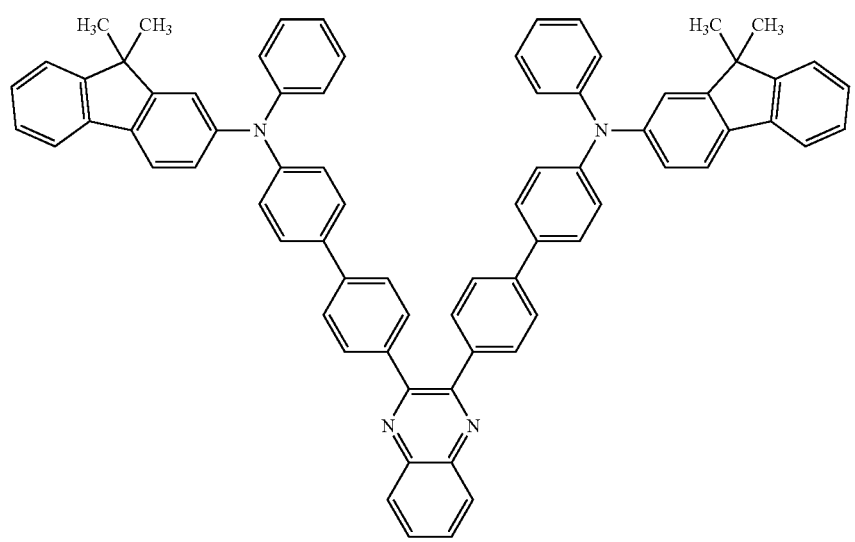
(44)

(45)
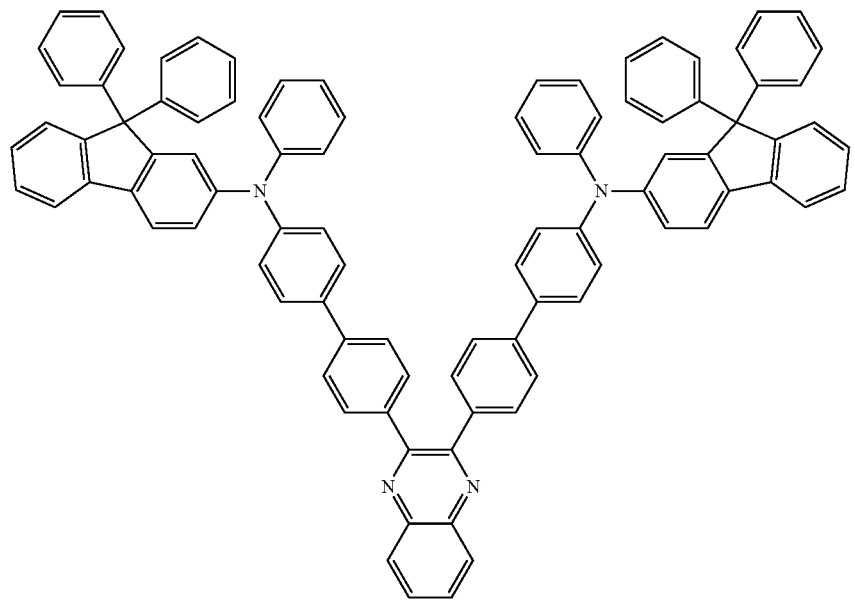
(46)
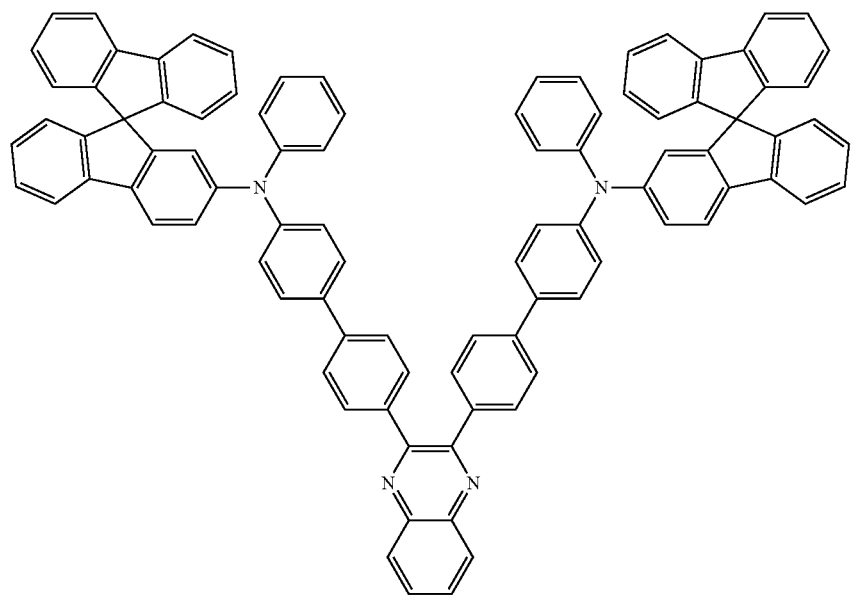
(47)
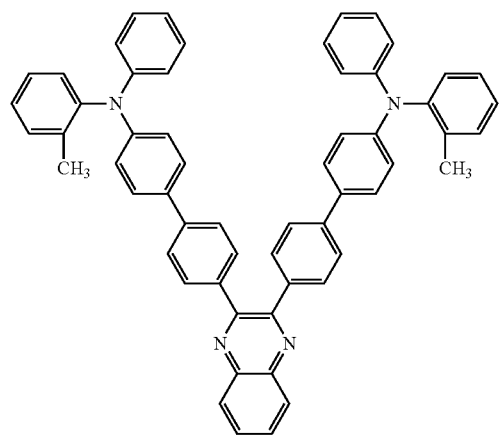
(48)
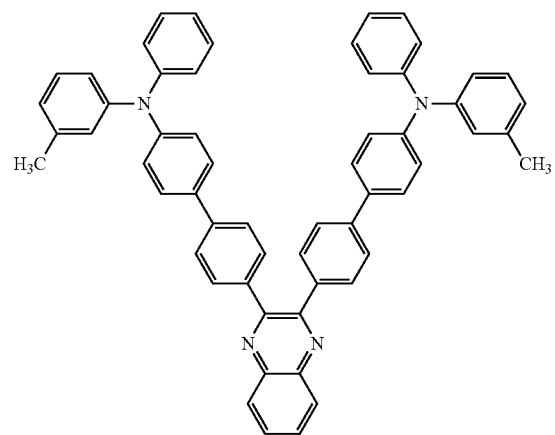

-continued
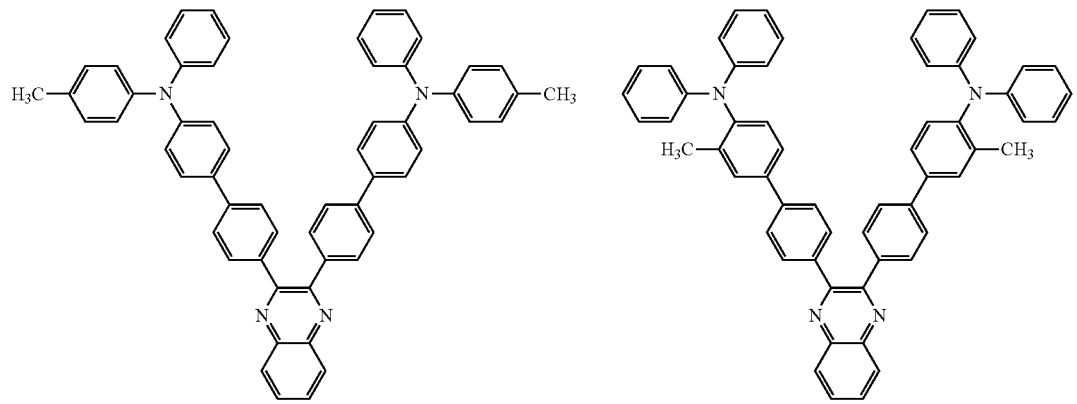
(49)
(50)
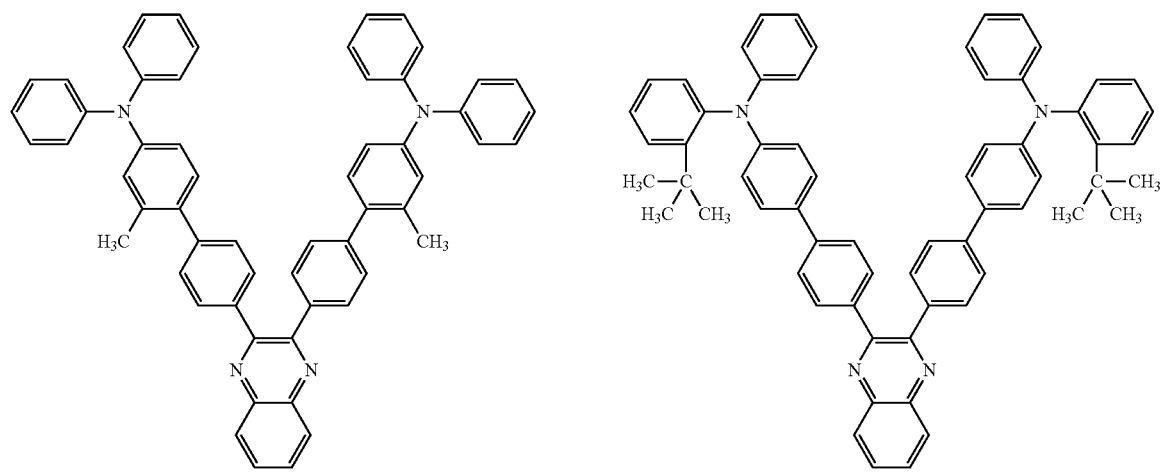
(51)
(52)
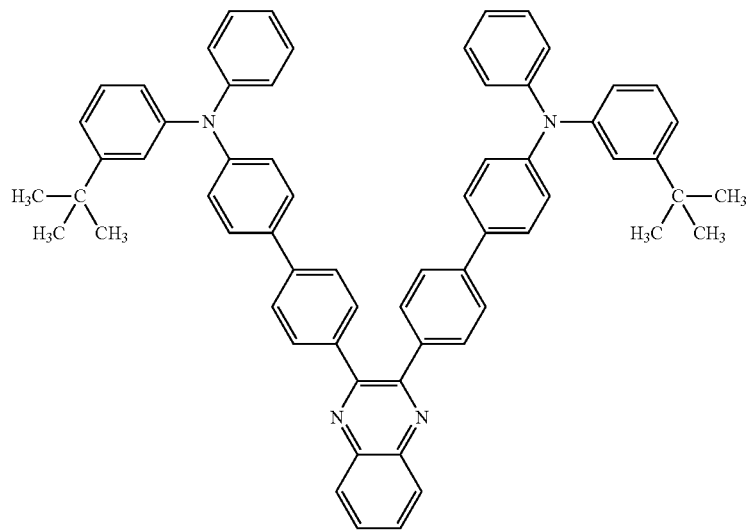
(53)

(54)
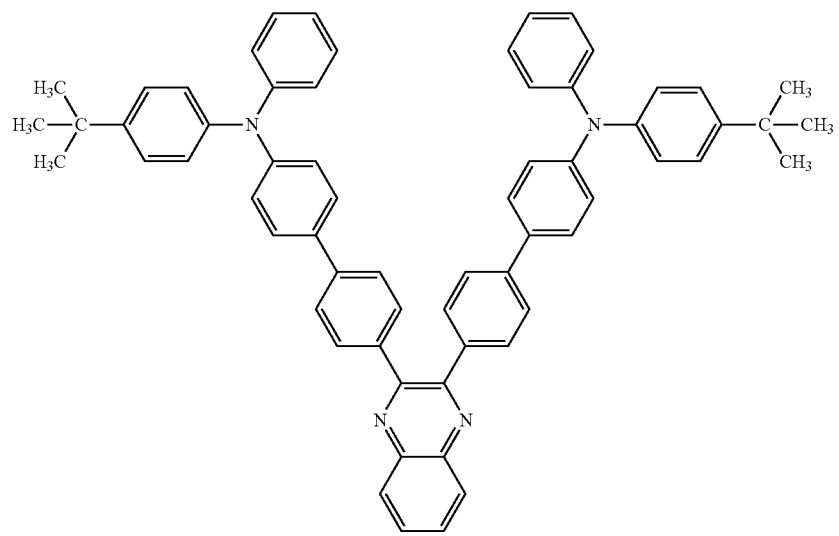
(55) (56)
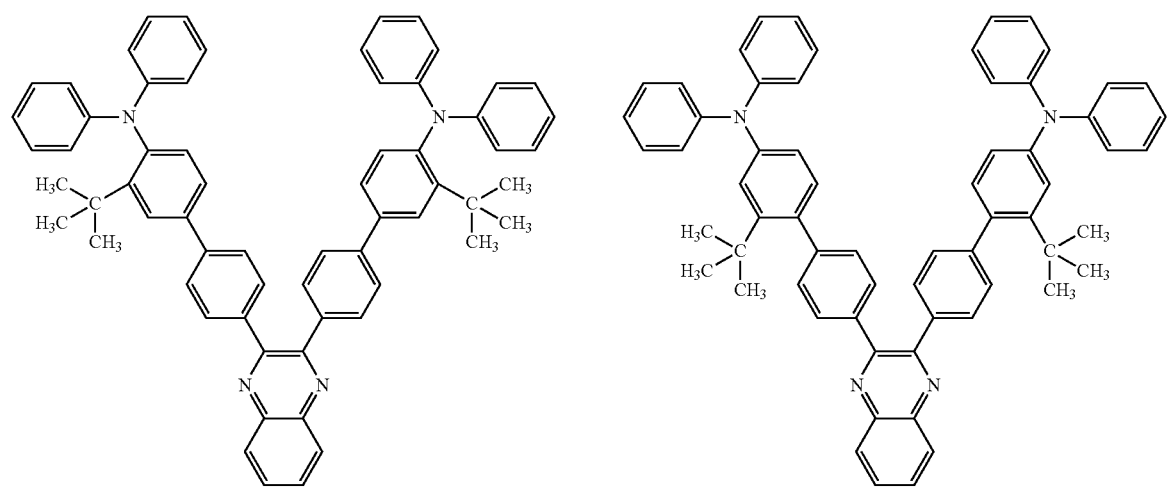
(57)
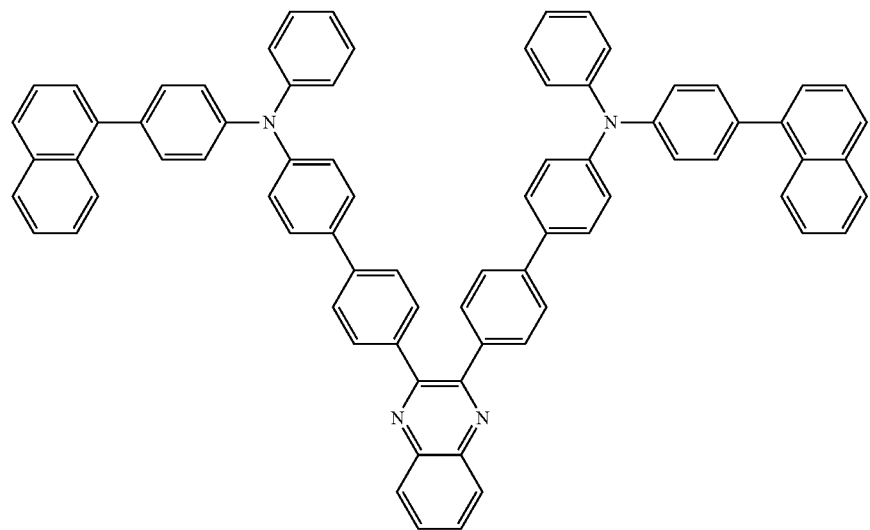

(58)
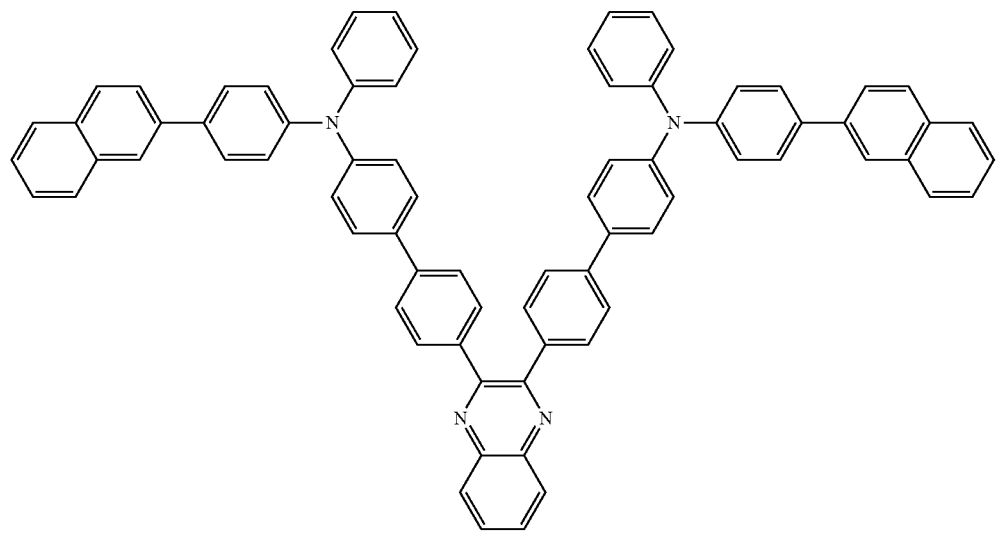
(59)
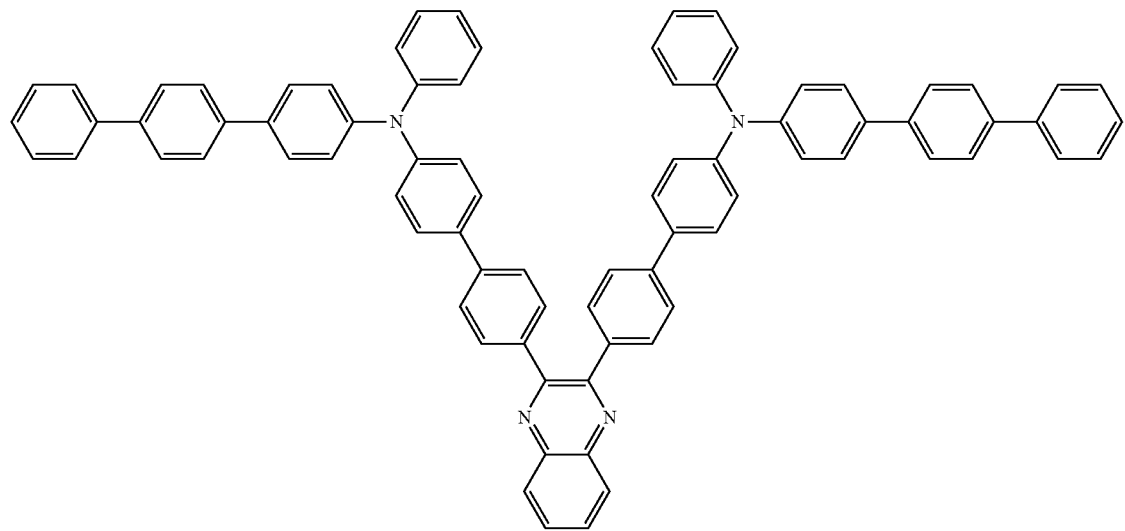
(60)
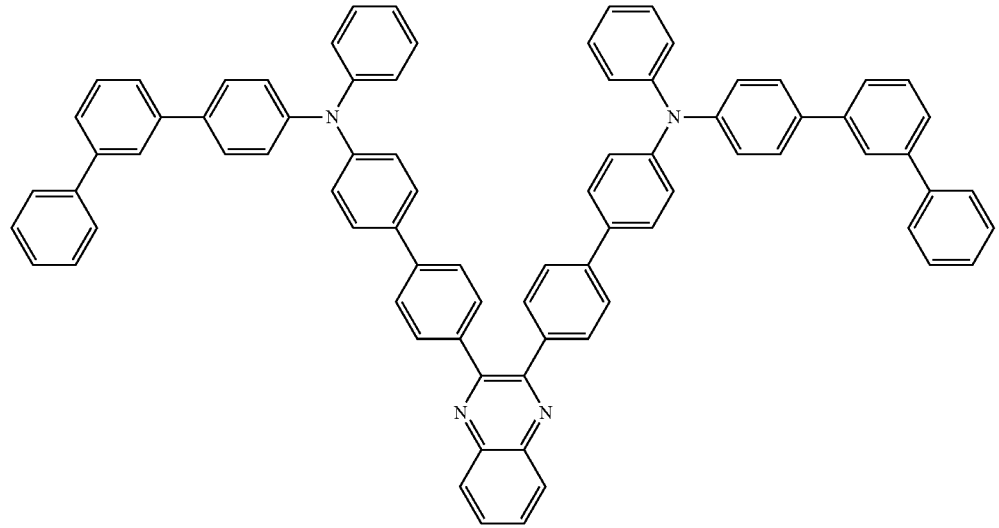

(61)
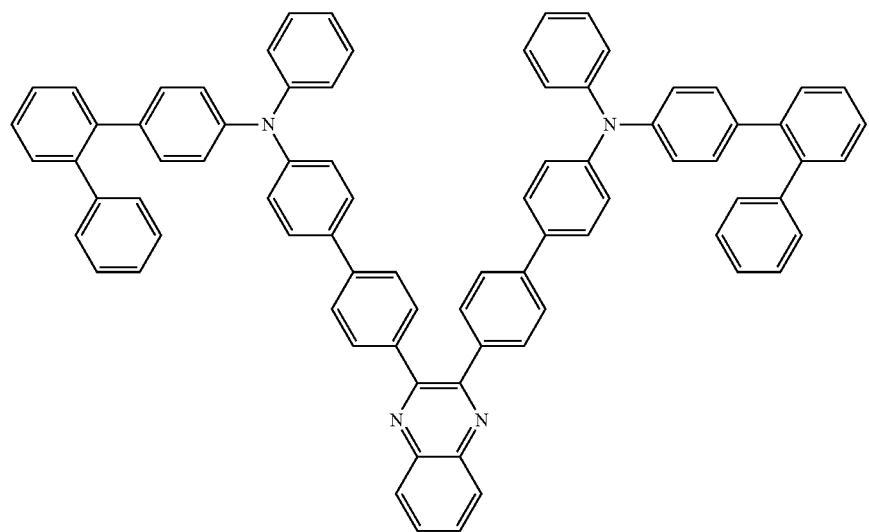
(62)
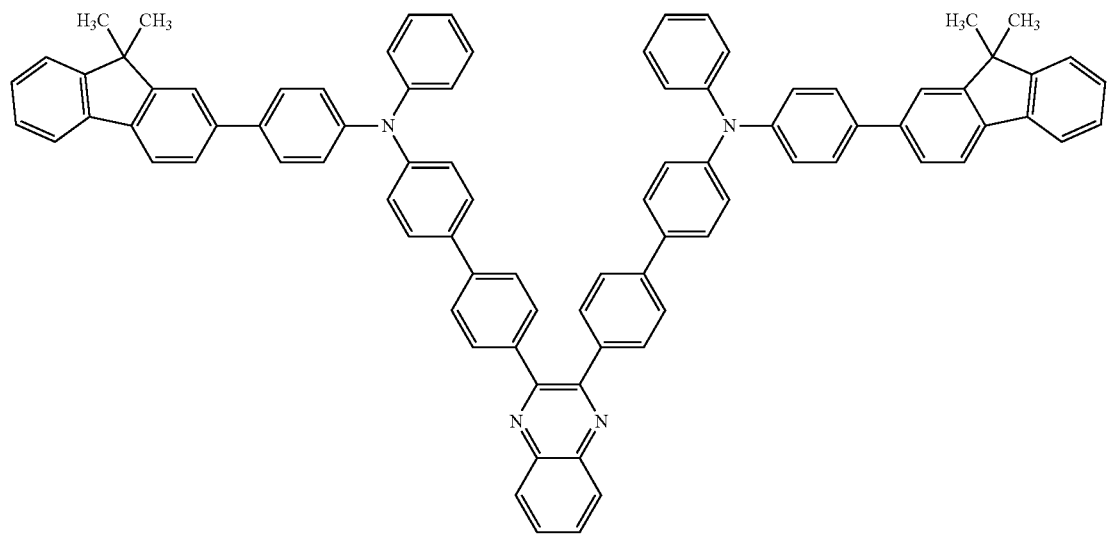
(63)
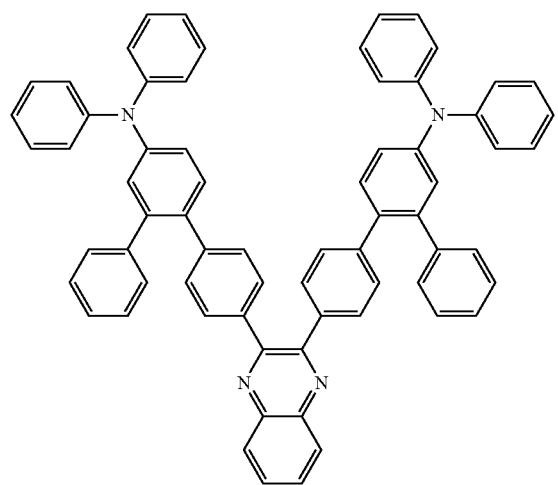
(64)
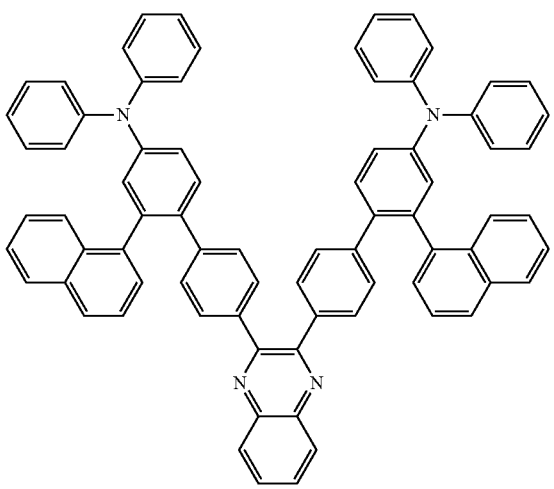

-continued
(65)
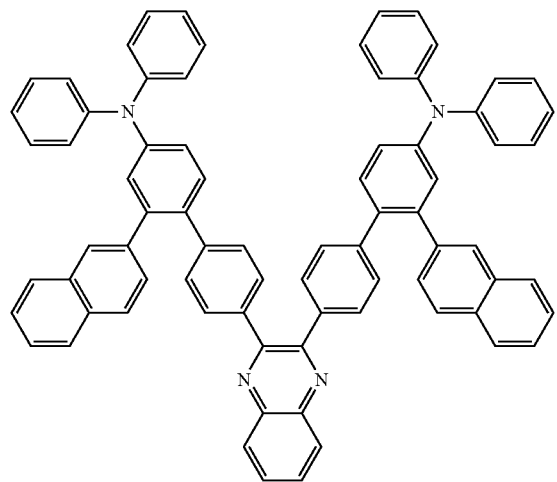
(66)
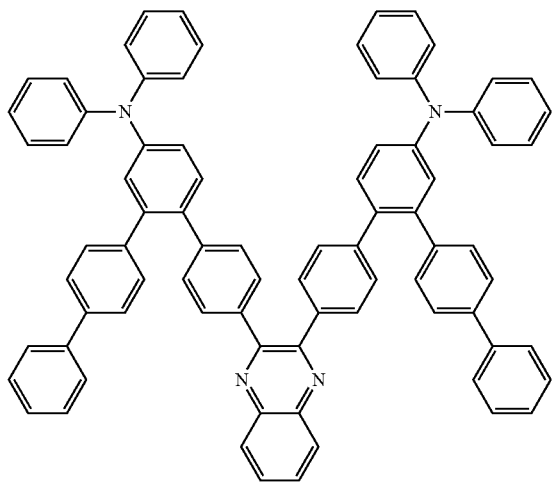
(67)
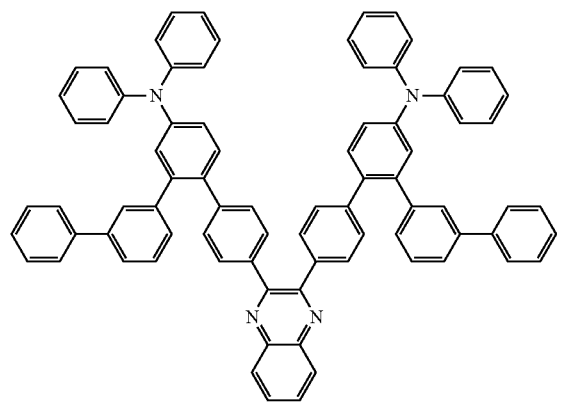
(68)
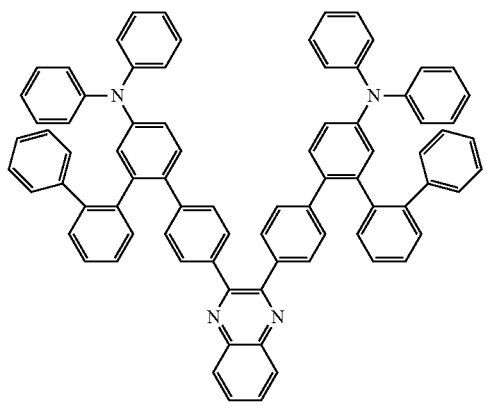
(69)
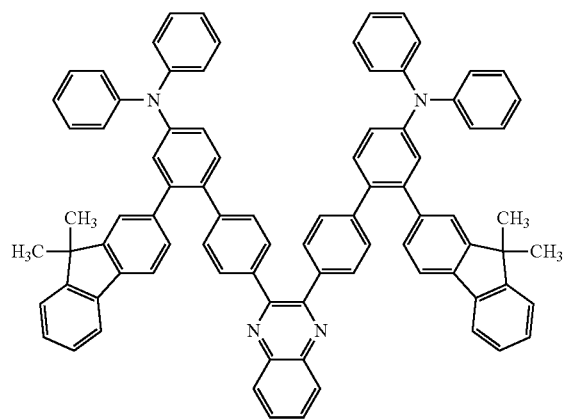
(70)
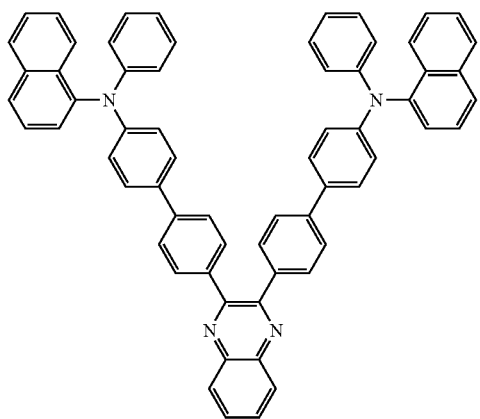

-continued
(71)
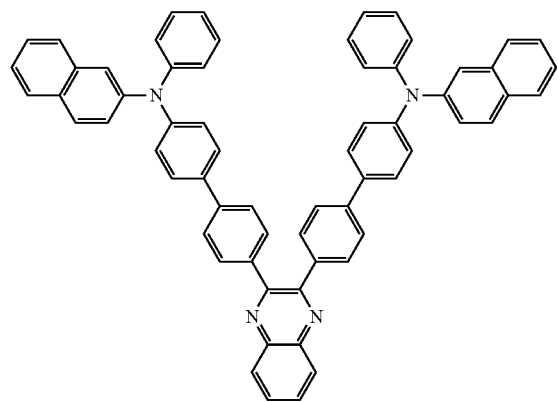
(72)
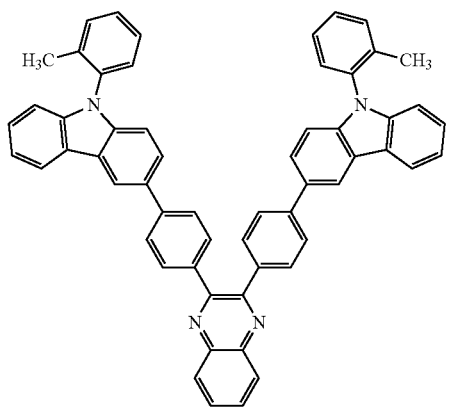
(73)
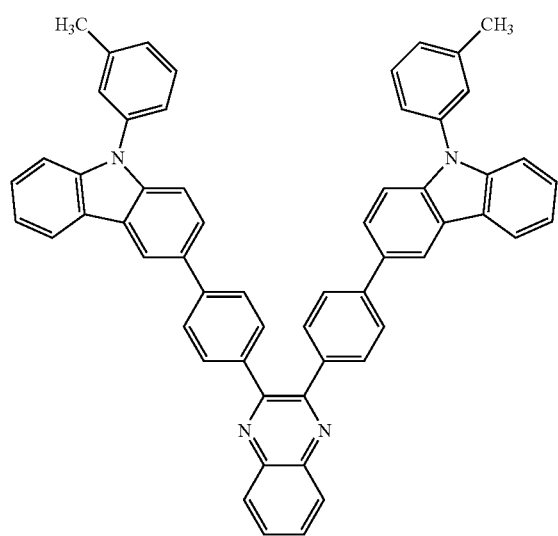
(74)
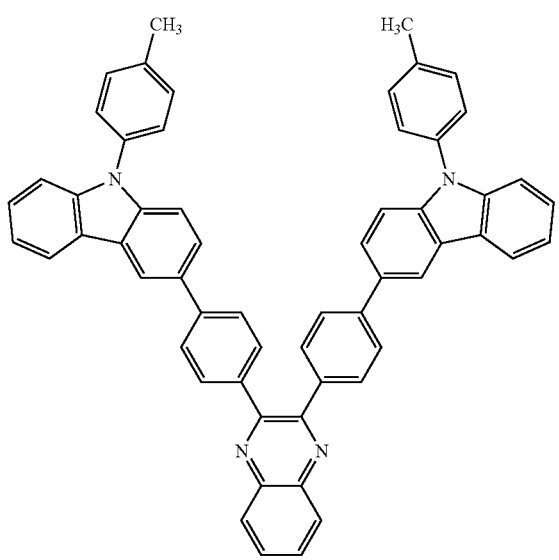
(75)
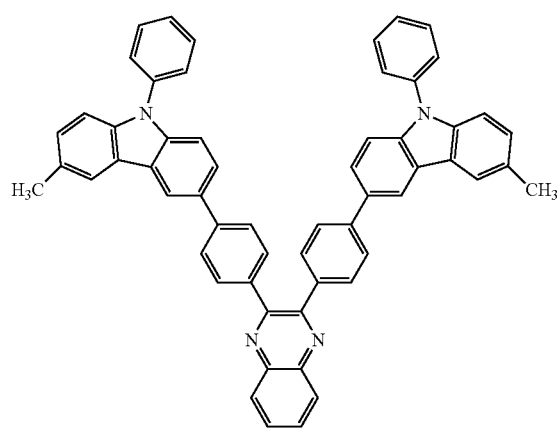
(76)
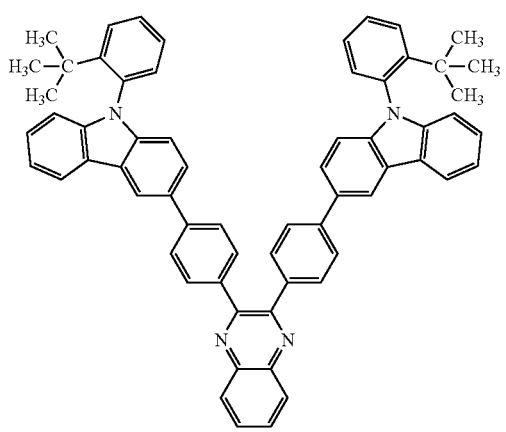

-continued
(77) 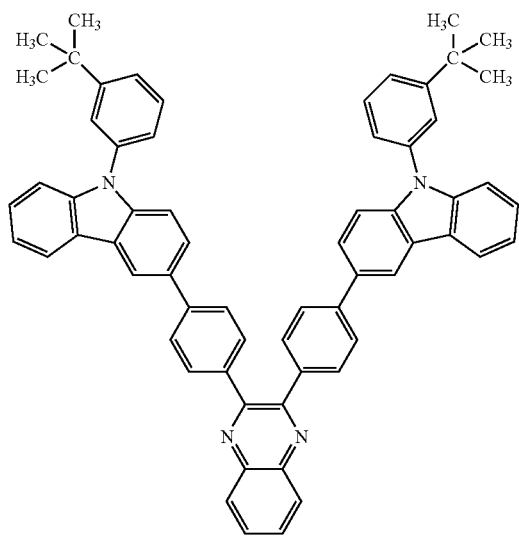
(78) 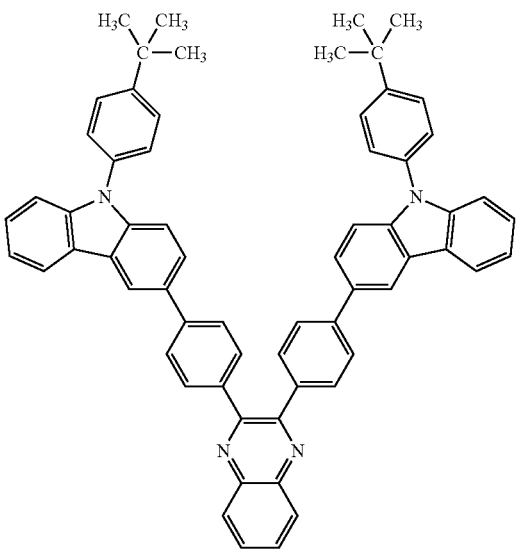
(79) 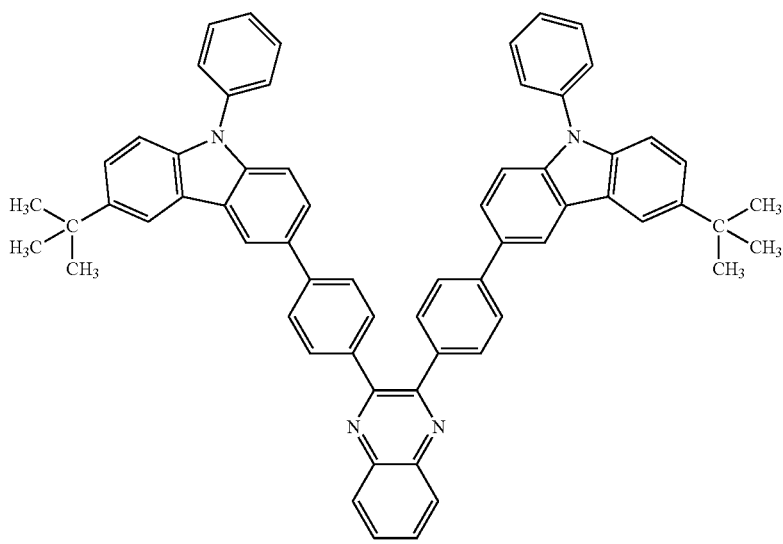
(80) 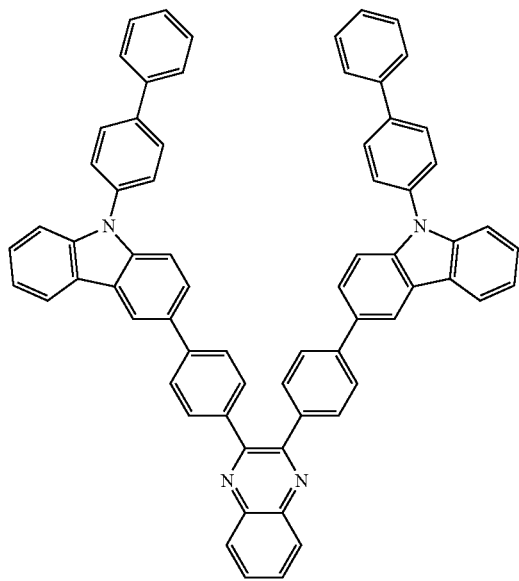
(81) 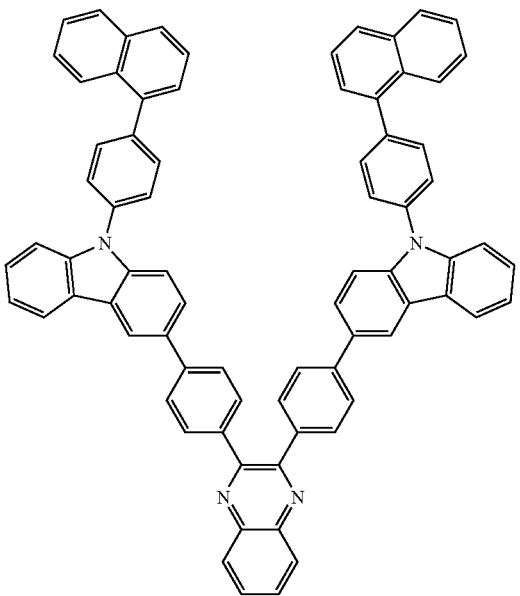

-continued
(82)
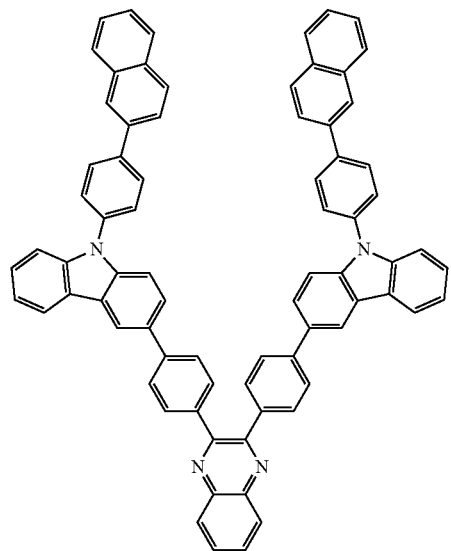
(83)
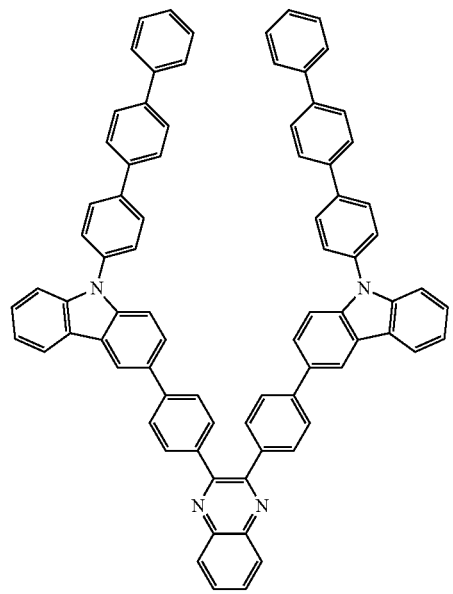
(84)
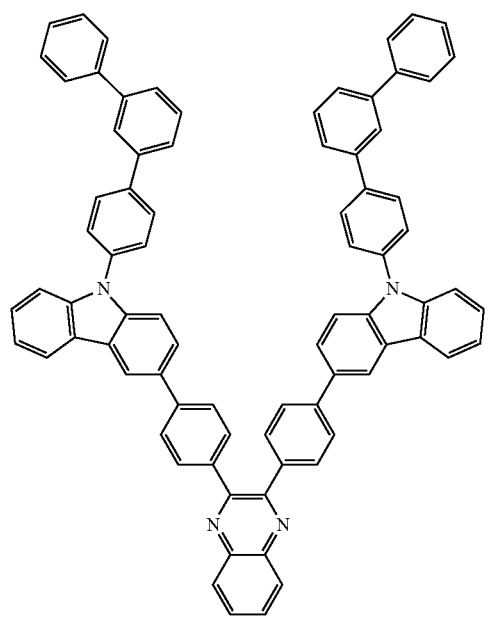
(85)
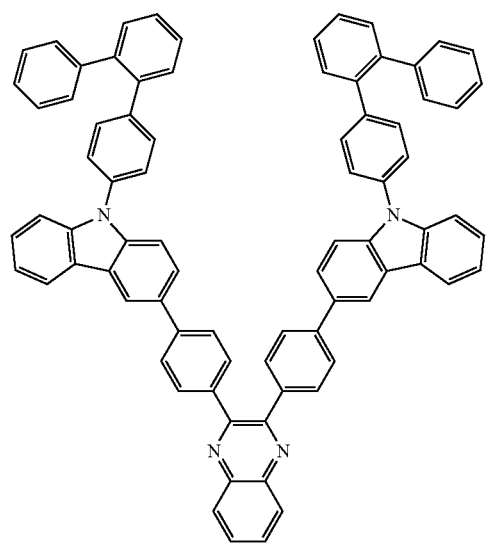

(86)
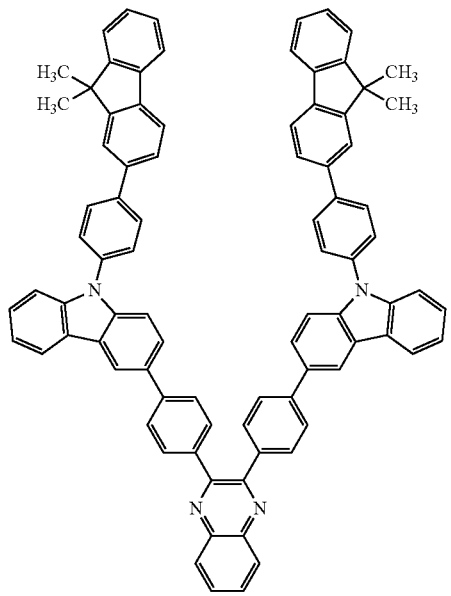
(87)
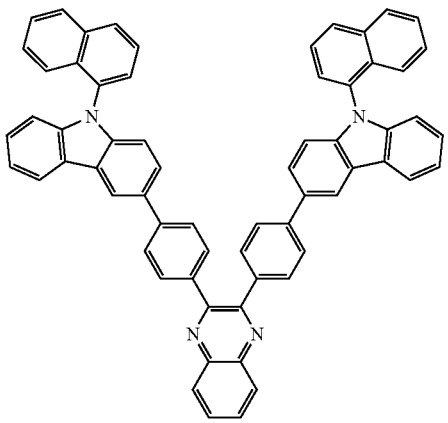
(88)
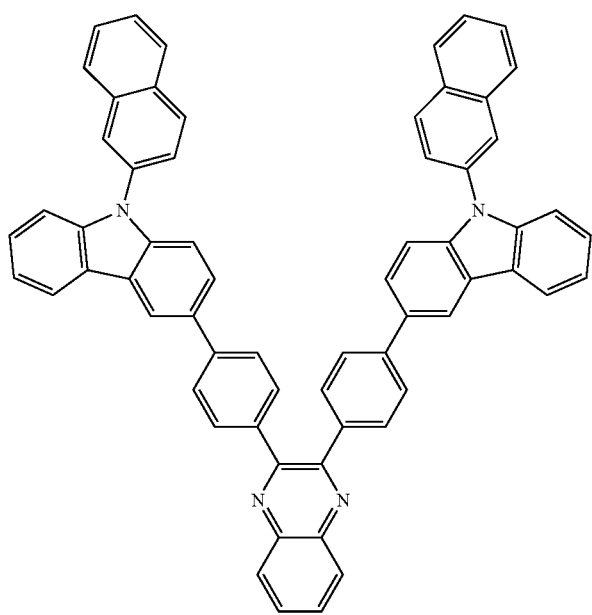

(89)
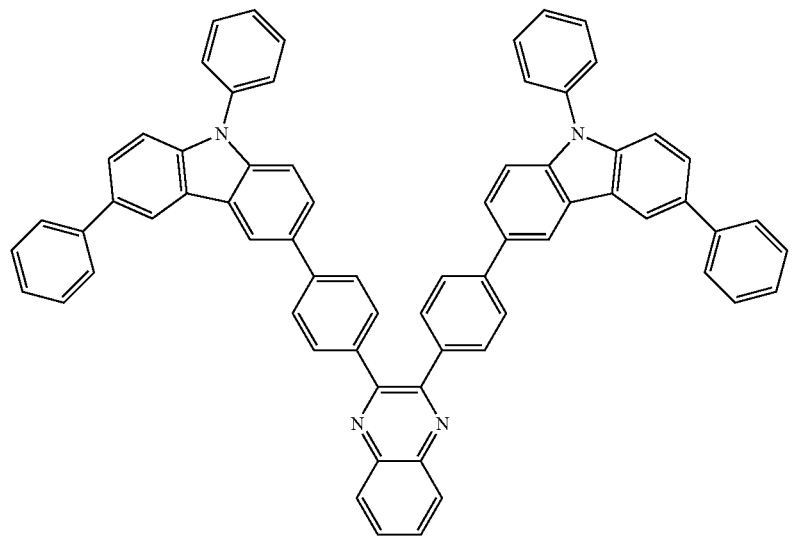
(90)
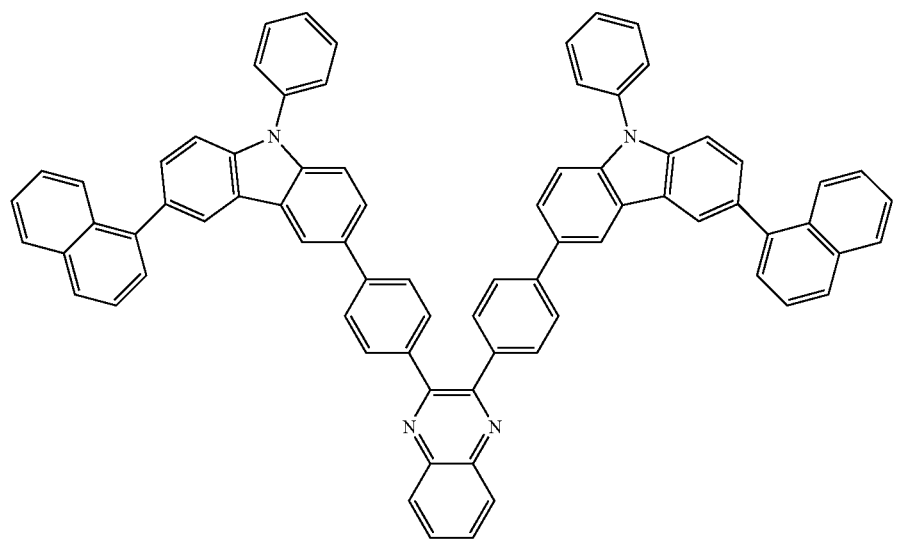
(91)
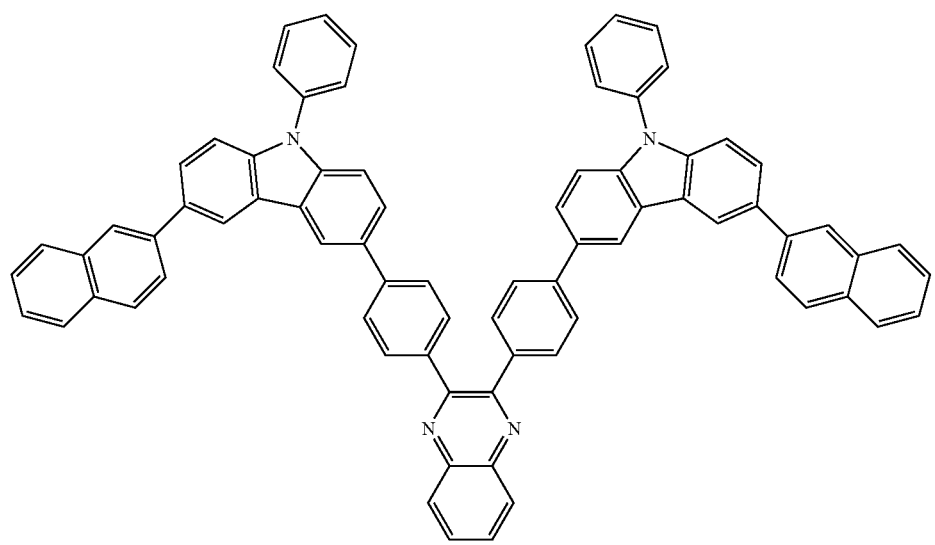

-continued
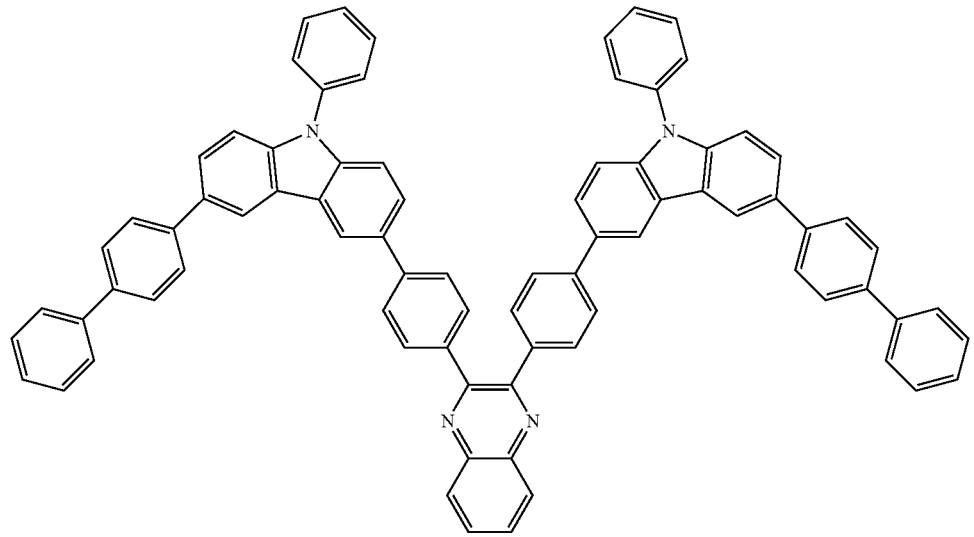
(92)
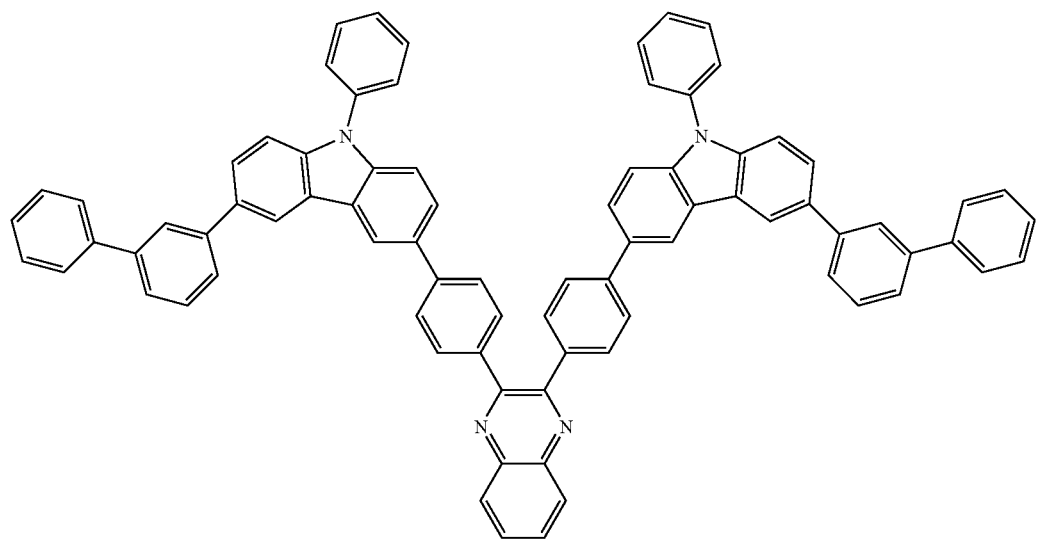
(93)
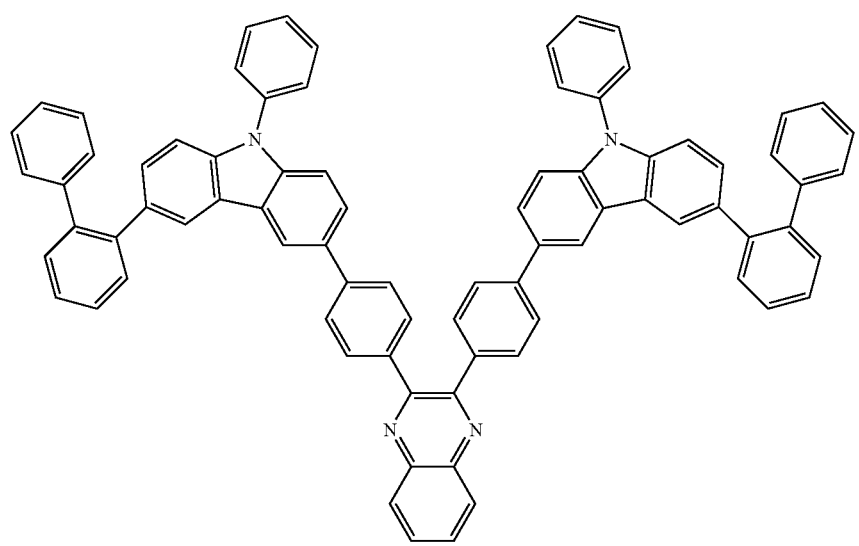
(94)

-continued
(95)
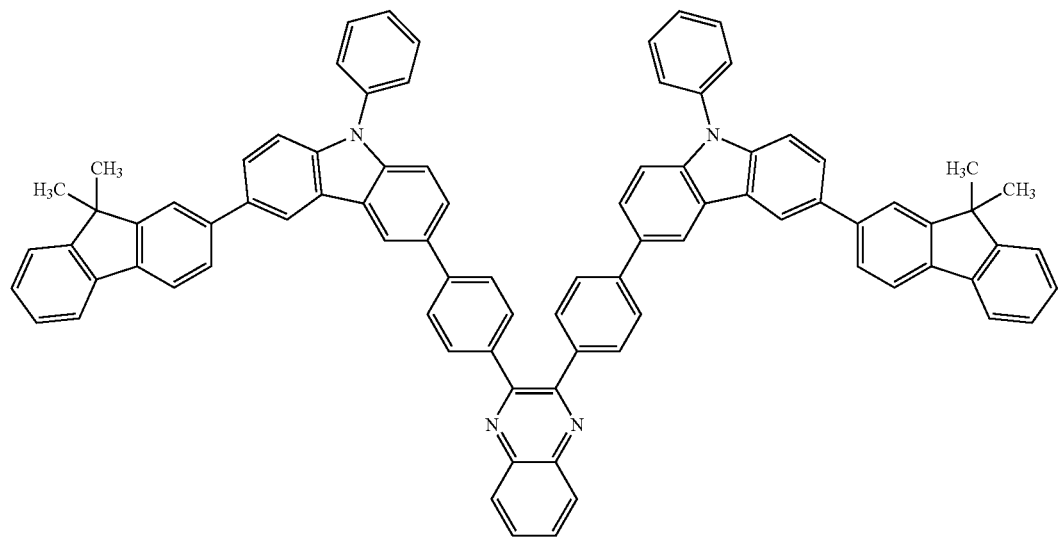
(96)
(97)
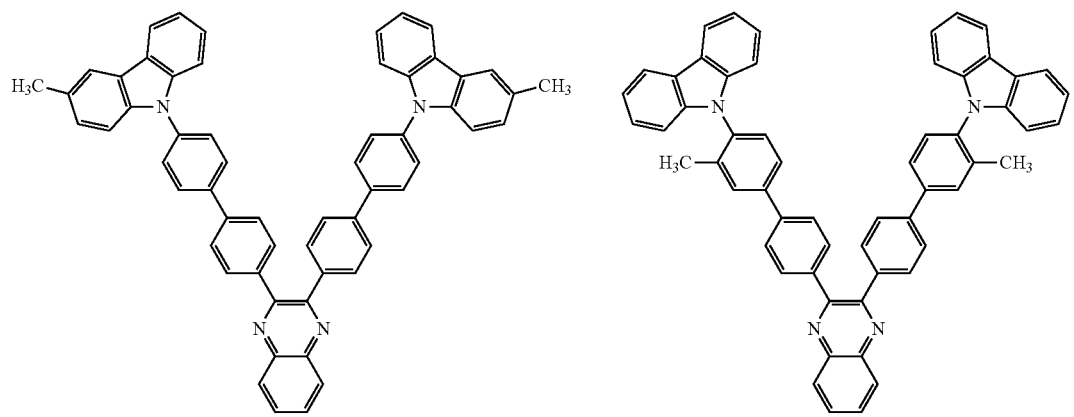
(98)
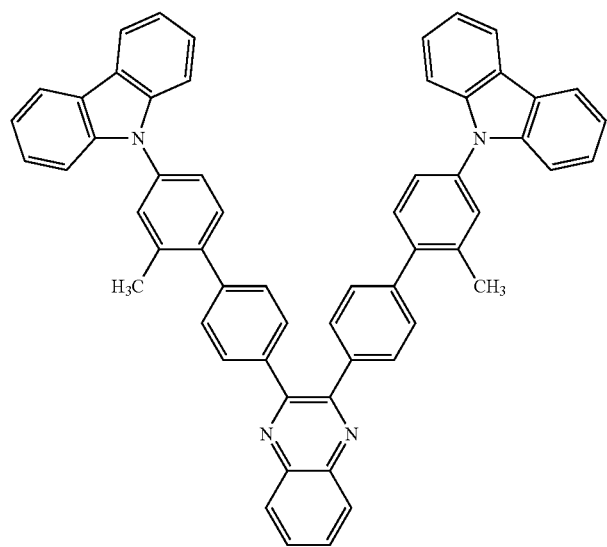

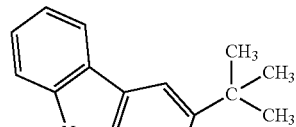
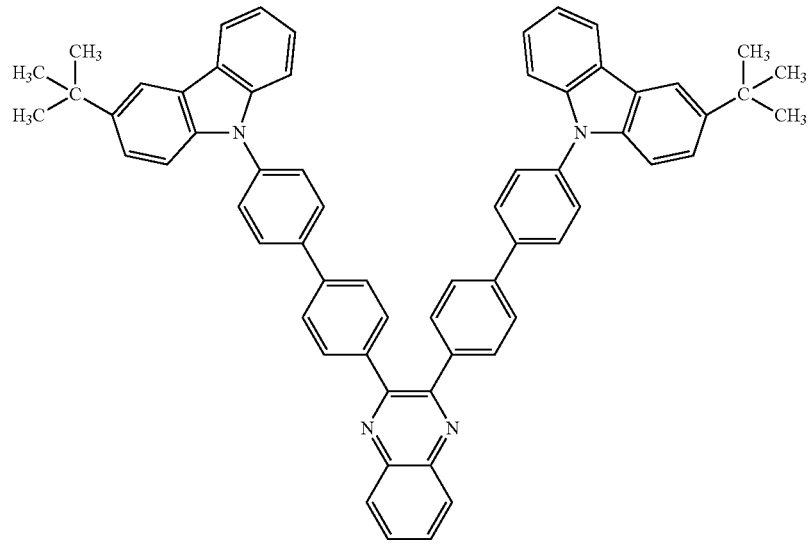
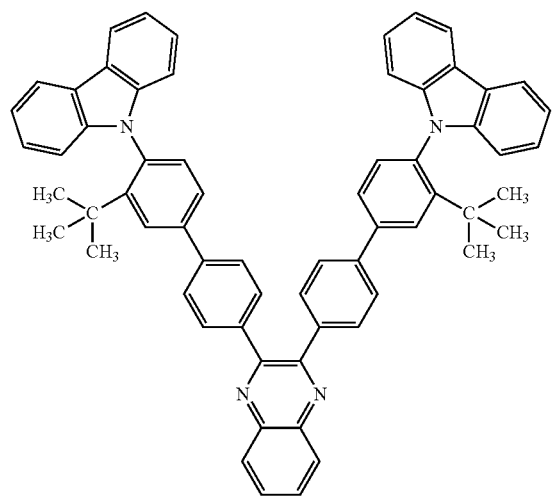 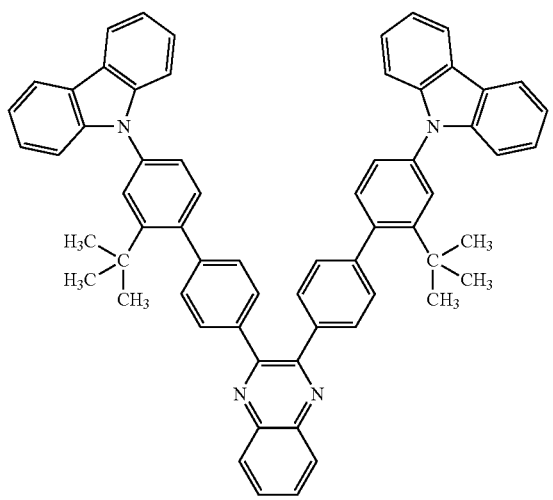
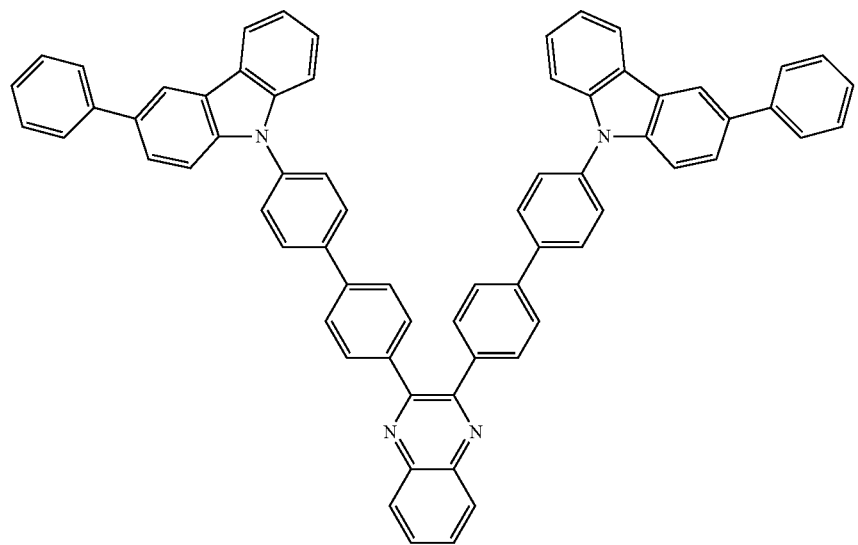

(103)
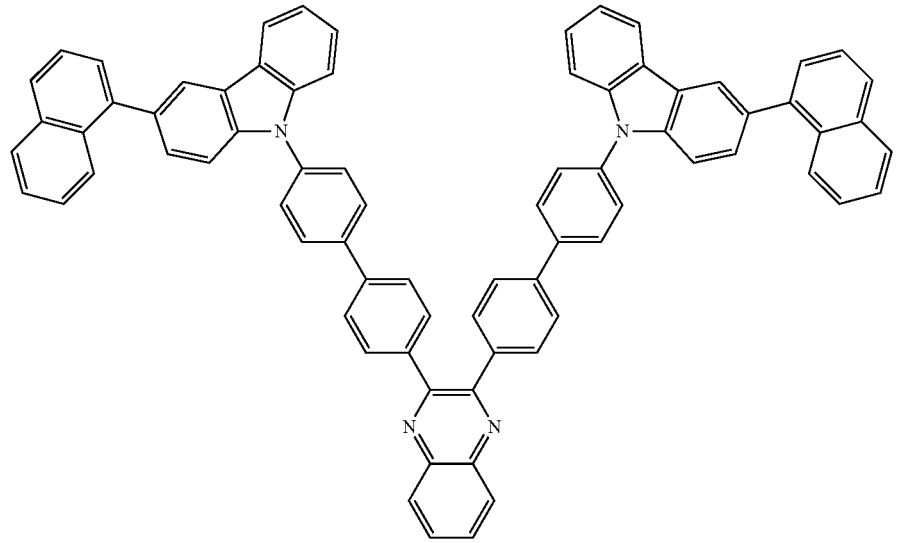
(104)
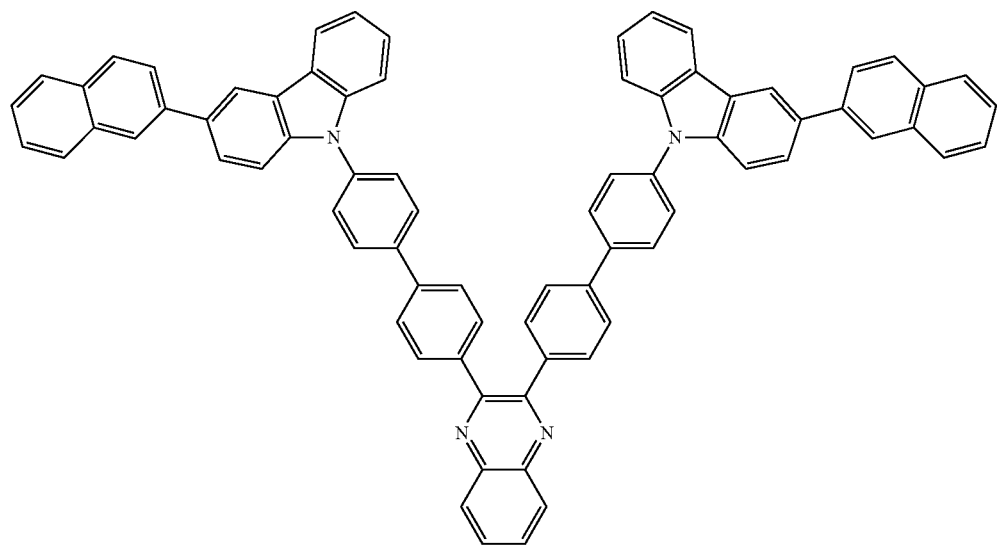
(105)
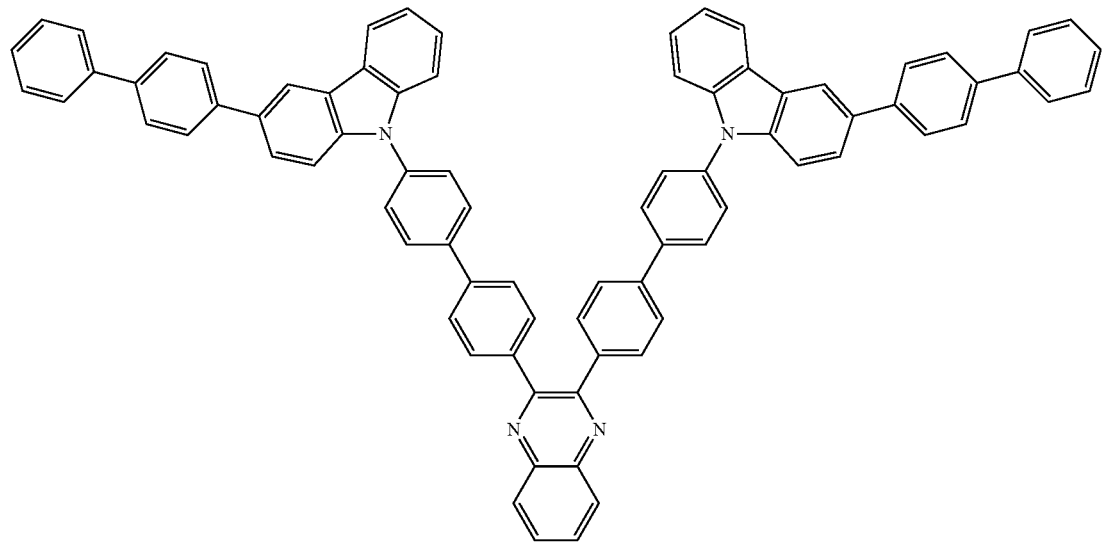

(106)
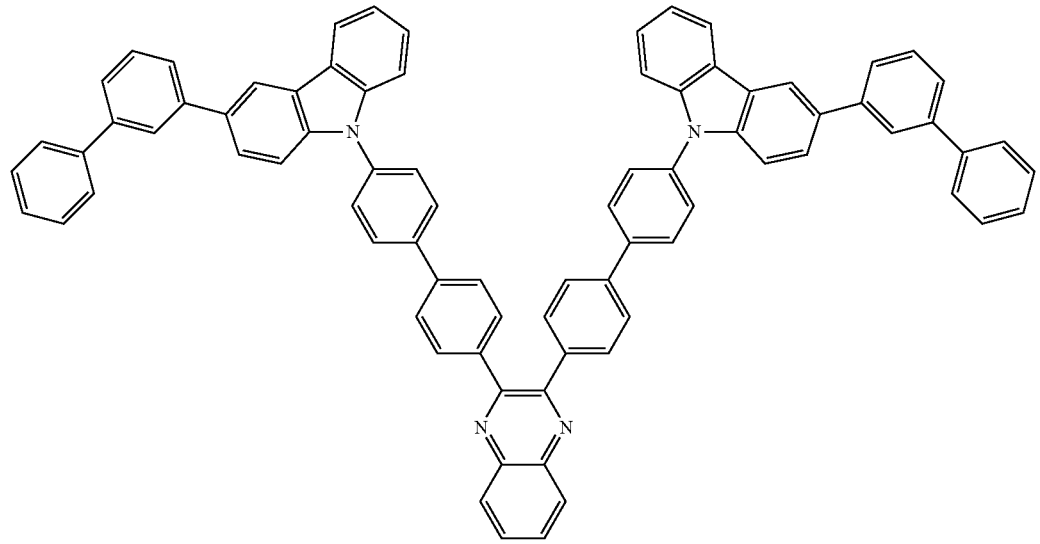
(107)
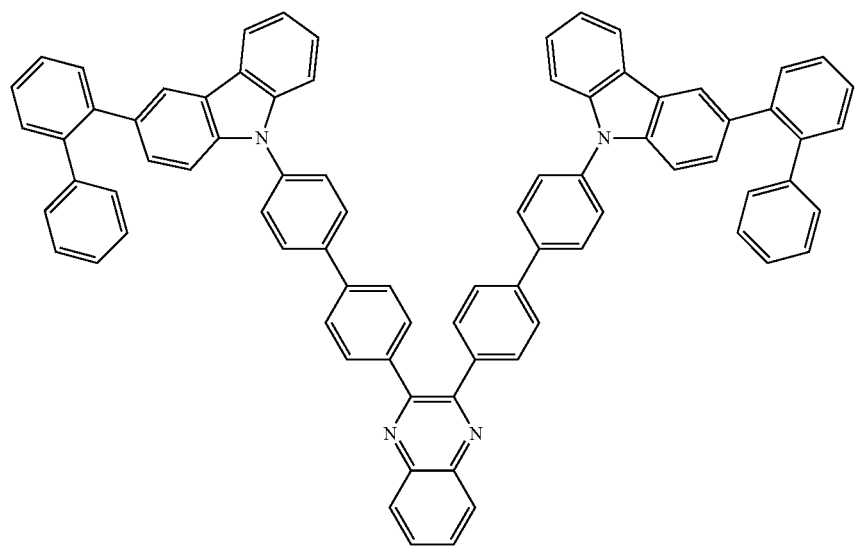
(108)
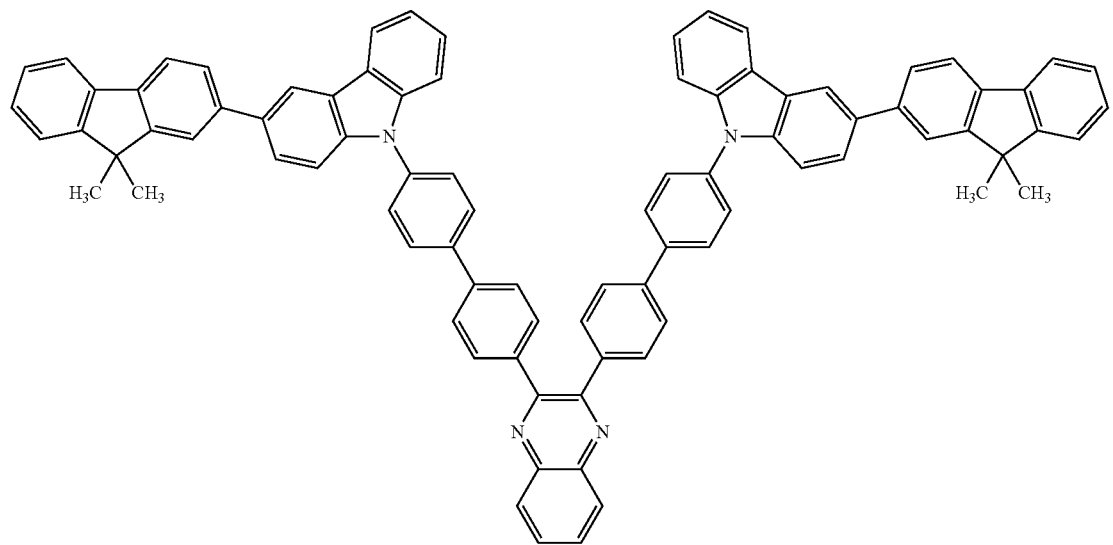

-continued
(109)
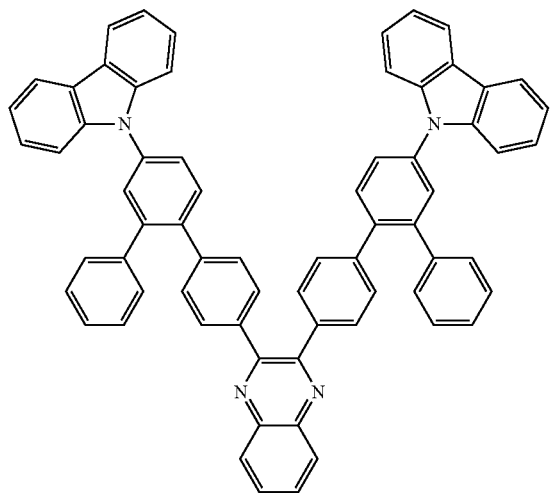
(110)
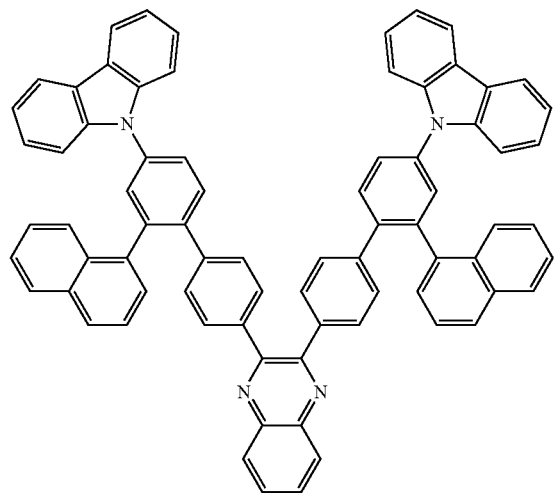
(111)
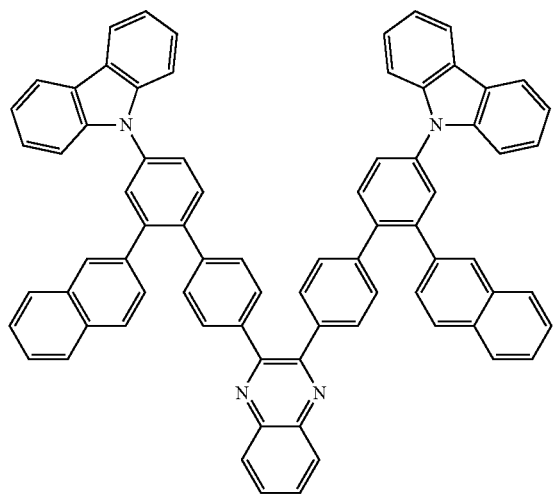
(112)
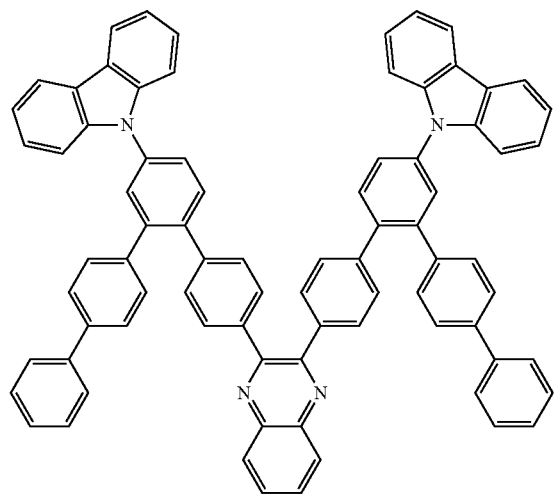
(113)
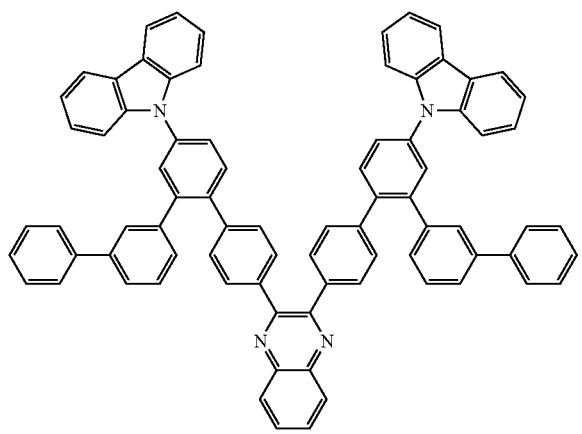
(114)
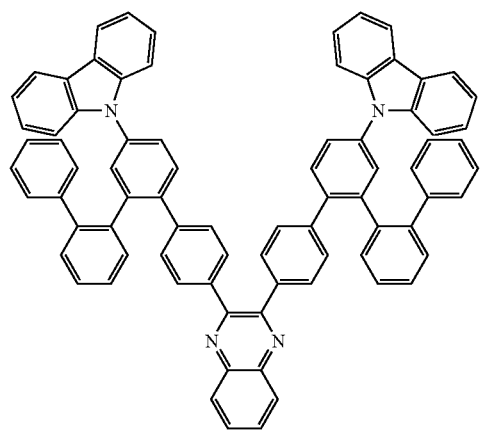

-continued

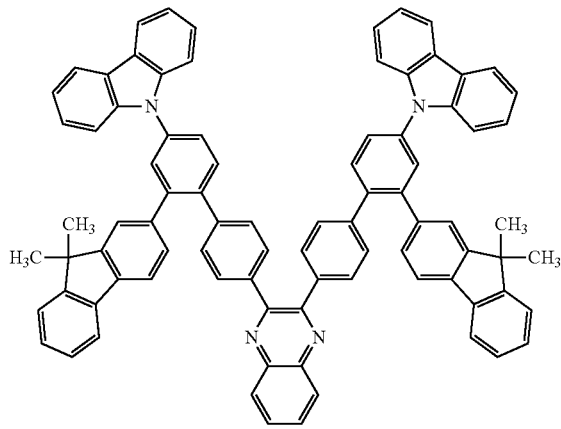
(115)

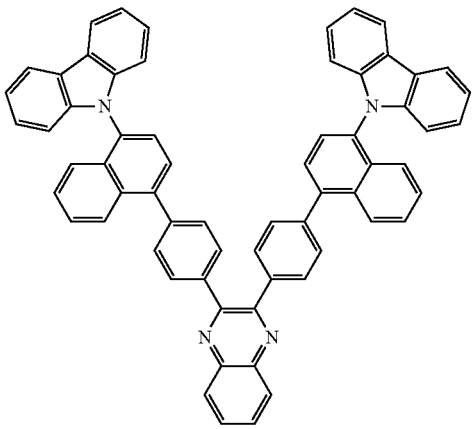
(116)

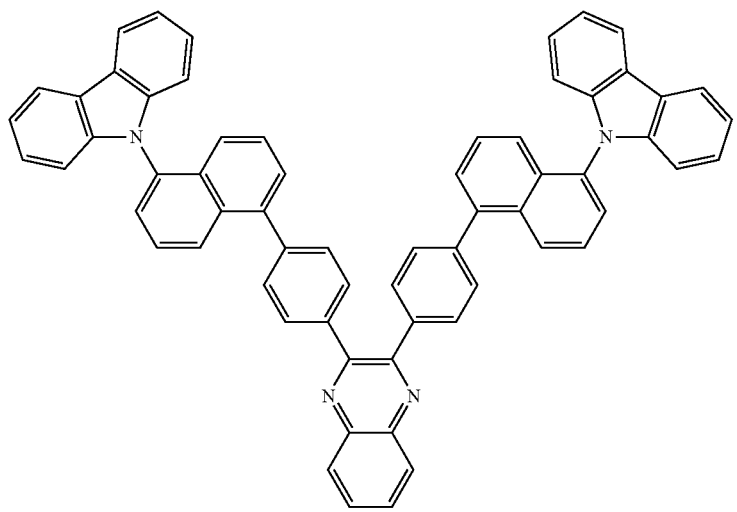
(117)

Various reactions can be applied as a synthesizing method of the quinoxaline derivative of the present invention. For example, the quinoxaline derivative can be made by a synthetic reaction shown in the synthetic schemes (A-1) to (A-4).

First, as shown in the synthetic scheme (A-1), a quinoxaline skeleton is formed by a condensation reaction between benzil substituted with halogen atoms $X^1$ and $X^2$ (a compound B) and a 1,2-diamino benzene derivative (a compound A). As examples of the halogen atom, bromine, iodine, and chlorine can be given. Considering ease in handling and reactivity, bromine or iodine is preferable.

(A-1)

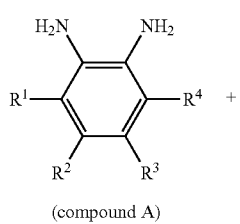
(compound A)

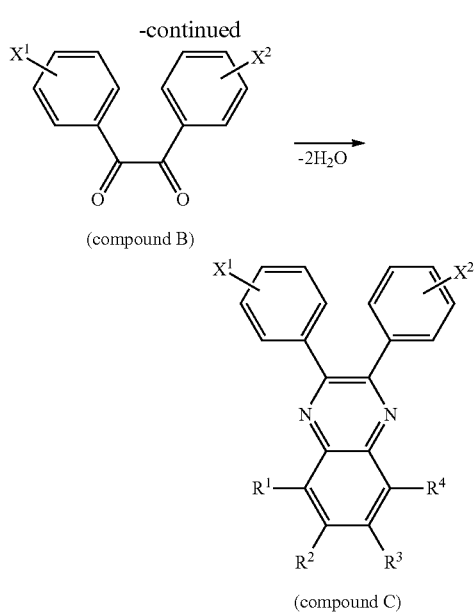

In the synthetic scheme (A-1), $X^1$ and $X^2$ may be the same or different and each represent a hydrogen atom. $R^1$ to $R^4$ may be the same or different and each represent any one of a hydrogen atom, an alkyl group of carbon number 1 to 4, and an aryl group of carbon number 6 to 25. $R^1$, $R^2$, and $R^3$ may bond to $R^2$, $R^3$, and $R^4$, respectively, to form a condensed ring.

Next, as shown in the synthetic scheme (A-2), organolithium is added to the halogen-substituted quinoxaline thus obtained (a compound C) to perform lithiation of the compound C and is reacted with a boron reagent such as trimethyl borate, triisopropyl borate, or the like, so that boronic acid of a quinoxaline derivative (a compound D) can be obtained.

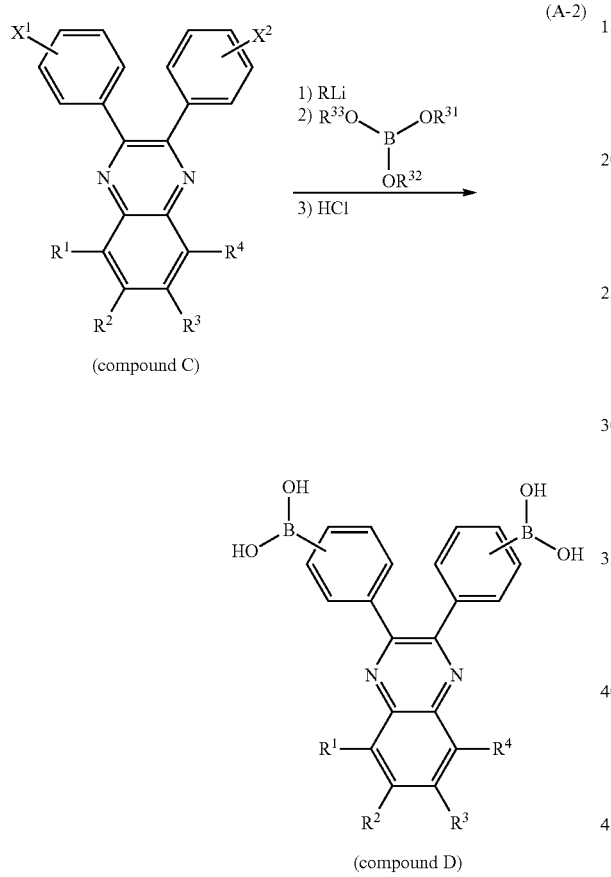

In the synthetic scheme (A-2), $X^1$ and $X^2$ may be the same or different and each represent a hydrogen atom. As examples of the halogen atom, bromine, iodine, and chlorine can be given. Considering ease in handling and reactivity, bromine or iodine is preferable. $R^1$ to $R^4$ may be the same or different and each represent any one of a hydrogen atom, an alkyl group of carbon number 1 to 4, and an aryl group of carbon number 6 to 25. $R^1$, $R^2$, and $R^3$ may bond to $R^2$, $R^3$, and $R^4$, respectively, to form a condensed ring. $R^{31}$ to $R^{33}$ may be the same or different and each represent any one of a hydrogen atom and an alkyl group of carbon number 1 to 10.

Next, as shown in the synthetic scheme (A-3), the quinoxaline derivative of the present invention can be synthesized by coupling the obtained boronic acid of a quinoxaline derivative (compound D) with a halogenated amine derivative (a compound E) by using a palladium catalyst or monovalent copper in the presence of a base. As the base, an inorganic base such as potassium carbonate or sodium carbonate, an organic base such as a metal alkoxide, or the like can be used. As the palladium catalyst, palladium acetate, palladium chloride, bis(dibenzylidineacetone)palladium, or the like can be used.

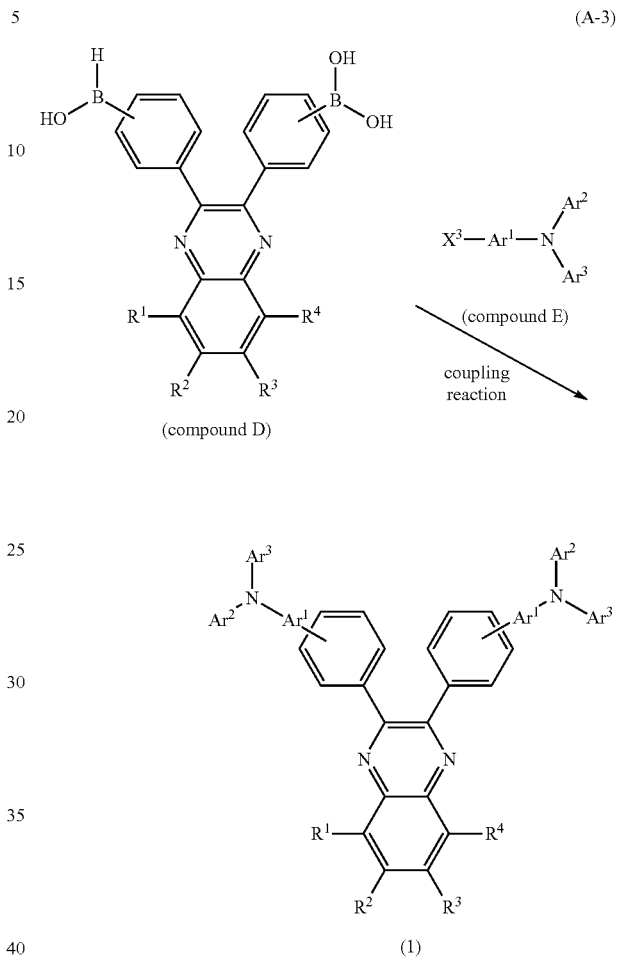

In the synthetic scheme (A-3), $R^1$ to $R^4$ may be the same or different and each represent any one of a hydrogen atom, an alkyl group of carbon number 1 to 4, and an aryl group of carbon number 6 to 25. $R^1$, $R^2$, and $R^3$ may bond to $R^2$, $R^3$, and $R^4$, respectively, to form a condensed ring. $Ar^1$ represents an arylene group of carbon number 6 to 25. $Ar^2$ and $Ar^4$ may be the same or different and each represent an arylene group of carbon number 6 to 25. $Ar^1$ and $Ar^2$ may bond to $Ar^2$ and $Ar^3$, respectively. $X^3$ represents a halogen atom. As examples of the halogen atom, bromine, iodine, and chlorine can be given. Considering ease in handling and reactivity, bromine or iodine is preferable.

Alternatively, as shown in the synthetic scheme (A-4), the quinoxaline derivative of the present invention can be synthesized by coupling the halogen-substituted quinoxaline (compound C) with boronic acid of an amine derivative or an organoboron compound of an amine derivative (a compound F) by using a palladium catalyst or monovalent copper in the presence of a base. As the base, an inorganic base such as potassium carbonate or sodium carbonate, an organic base such as a metal alkoxide, or the like can be used. As the palladium catalyst, palladium (II) acetate, tetrakis(triphenylphosphine)palladium (0), or the like can be used.

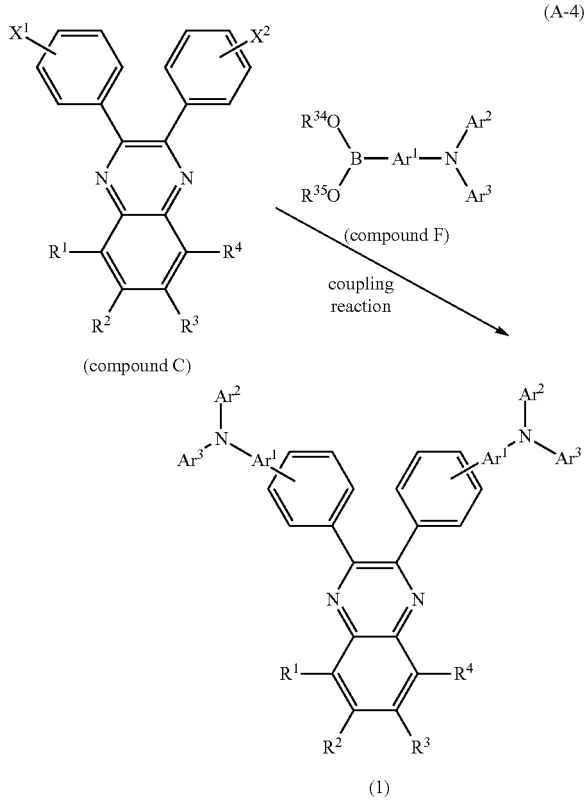

In the synthetic scheme (A-4), $R^1$ to $R^4$ may be the same or different and each represent any one of a hydrogen atom, an alkyl group of carbon number 1 to 4, and an aryl group of carbon number 6 to 25. $R^1$, $R^2$, and $R^3$ may bond to $R^2$, $R^3$, and $R^4$, respectively, to form a condensed ring. $Ar^1$ represents an arylene group of carbon number 6 to 25. $Ar^2$ and $Ar^3$ may be the same or different and each represent an arylene group of carbon number 6 to 25. $Ar^1$ and $Ar^2$ may bond to $Ar^2$ and $Ar^3$, respectively. $R^{34}$ and $R^{35}$ may be the same or different and each represent any one of a hydrogen atom and an alkyl group of carbon number 1 to 10. $R^{34}$ and $R^{35}$ may bond to each other to form a condensed ring. $X^1$ and $X^2$ may be the same or different and each represent a halogen atom. As examples of the halogen atom, bromine, iodine, and chlorine can be given. Considering ease in handling and reactivity, bromine or iodine is preferable.

The quinoxaline derivative of the present invention is bipolar and excellent in both electron transporting property and hole transporting property. Therefore, by using the quinoxaline derivative of the present invention for an electronic device, good electric characteristics can be obtained. Further, the quinoxaline derivative of the present invention has a high glass transition point and excellent heat resistance; therefore, by using the quinoxaline derivative of the present invention for an electronic device, an electronic device which has excellent heat resistance can be obtained. Furthermore, the quinoxaline derivative of the present invention is stable with respect to electrochemical oxidation or reduction; therefore, by using the quinoxaline derivative of the present invention for an electronic device, a long-life electronic device can be obtained.

(Embodiment Mode 2)

In this embodiment mode, one mode of a light emitting element using the quinoxaline derivative of the present invention, with reference to FIGS. 1A to 1C and 2 is described.

A light emitting element of the present invention includes a plurality of layers interposed between a pair of electrodes. The plurality of layers are stacked in which layers each containing a material having a high carrier injecting property or a material having a high carrier transporting property are combined so that a light emitting region is formed apart from the electrodes, that is, so that carriers are recombined at a portion away from the electrodes. In this specification, the plurality of layers formed between the pair of electrodes is hereinafter referred to as an EL layer.

In this embodiment mode, the light emitting element includes a first electrode 102; a first layer 103, a second layer 104, a third layer 105, and a fourth layer 106 which are stacked in this order over the first electrode 102; and a second electrode 107 provided over the fourth layer 106. In this embodiment mode, the following description is made assuming that the first electrode 102 functions as an anode and the second electrode 107 functions as a cathode.

A substrate 101 is used to support the light emitting element. As the substrate 101, for example, glass, plastic, or the like can be used. Any other material may also be used as long as the light emitting element can be supported during a manufacturing process.

As the first electrode 102, the following is preferably used: a metal, an alloy, a conductive compound, or a mixture thereof, having a high work function (specifically, 4.0 eV or higher). Specifically, for example, the following can be given: indium tin oxide (ITO); indium tin oxide containing silicon or silicon oxide; indium zinc oxide (IZO); indium oxide containing tungsten oxide and zinc oxide (IWZO); and the like. Although such a conductive metal oxide film is generally formed by sputtering, it may also be formed by a sol-gel method or the like. For example, indium zinc oxide (IZO) can be formed by sputtering using a target in which zinc oxide is mixed at 1 wt % to 20 wt % in indium oxide; and indium oxide containing tungsten oxide and zinc oxide (IWZO) can be formed by sputtering using a target in which tungsten oxide at 0.5 wt % to 5 wt % and zinc oxide at 0.1 wt % to 1 wt % are contained in indium oxide. Further, the following can be used: gold (Au), platinum (Pt), nickel (Ni), tungsten (W), chromium (Cr), molybdenum (Mo), iron (Fe), cobalt (Co), copper (Cu), palladium (Pd), a nitride of a metal material (e.g., titanium nitride), or the like.

The first layer 103 contains a material having a high hole injecting property. Molybdenum oxide, vanadium oxide, ruthenium oxide, tungsten oxide, manganese oxide, or the like can be used. Further, the first layer 103 can also be formed of a phthalocyanine-based compound such as phthalocyanine (abbrev.: $H_2Pc$) or copper phthalocyanine (abbrev.: CuPc); an aromatic amine compound such as 4,4'-bis[N-(4-diphenylaminophenyl)-N-phenylamino]biphenyl (abbrev.: DPAB) or 4,4'-bis(N-{4-[N-(3-methylphenyl)-N-phenylamino]phenyl}-N-phenylamino)biphenyl (abbrev.: DNTPD); a high molecule such as poly(ethylene dioxythiophene)/poly(styrenesulfonic acid) (abbrev.: PEDOT/PSS); or the like.

Alternatively, a composite material including an organic compound and an inorganic compound can be used as the first layer 103. In particular, a composite material including an organic compound and an inorganic compound showing an electron-accepting property with respect to the organic compound is excellent in hole injecting property and hole transporting property since electrons are transferred between the organic compound and the inorganic compound and carrier density is increased.

Further, in the case of using a composite material including an organic compound and an inorganic compound as the first layer 103, the first layer 103 can form an ohmic contact with the first electrode 102; therefore, a material of the first electrode can be selected, regardless of work function.

As the inorganic compound used for the composite material, an oxide of a transition metal is preferably used. In addition, an oxide of a metal in Groups 4 to 8 of the Periodic Table of the Elements can be used as well. Specifically, the following are preferable because the electron-accepting property is high: vanadium oxide, niobium oxide, tantalum oxide, chromium oxide, molybdenum oxide, tungsten oxide, manganese oxide, and rhenium oxide. Of these, molybdenum oxide is particularly preferable because it is stable in the atmosphere, low in hygroscopicity, and is easy to handle.

As the organic compound used for the composite material, various compounds can be used, such as an aromatic amine compound, a carbazole derivative, aromatic amine hydrocarbon, a high molecular weight compound (e.g., an oligomer, a dendrimer, or a polymer). Note that, as the organic compound used for the composite material, it is preferable that it is an organic compound having a high hole transporting property. Specifically, it is preferable that it is a material having a hole mobility of $10^{-6}$ cm$^2$/Vs or more. Further, other materials than these may also be used as long as they are materials in which a hole transporting property is higher than an electron transporting property. Examples of the organic compound which can be used for the composite material are specifically listed below.

For example, as examples of the aromatic amine compound, the following can be given: N,N'-di(p-tolyl)-N,N'-diphenyl-p-phenylenediamine (abbrev.: DTDPPA); 4,4'-bis[N-(4-diphenylaminophenyl)-N-phenylamino]biphenyl (abbrev.: DPAB); 4,4'-bis(N-{4-[N-(3-methylphenyl)-N-phenylamino]phenyl}-N-phenylamino)biphenyl (abbrev.: DNTPD); 1,3,5-tris[N-(4-diphenylaminophenyl)-N-phenylamino]benzene (abbrev.: DPA3B); and the like.

As examples of the carbazole derivative which can be used for the composite material, the following can be given: 3-[N-(9-phenylcarbazol-3-yl)-N-phenylamino]-9-phenylcarbazole (abbrev.: PCzPCA1); 3,6-bis[N-(9-phenylcarbazol-3-yl)-N-phenylamino]-9-phenylcarbazole (abbrev.: PCzPCA2); 3-[N-(1-naphthyl)-N-(9-phenylcarbazol-3-yl)amino]-9-phenylcarbazole (abbrev.: PCzPCN1); and the like.

Further, the following can also be used: 4,4'-di(N-carbazolyl)biphenyl (abbrev.: CBP); 1,3,5-tris[4-(N-carbazolyl)phenyl]benzene (abbrev.: TCPB); 9-[4-(N-carbazolyl)]phenyl-10-phenylanthracene (abbrev.: CzPA); 1,4-bis[4-(N-carbazolyl)phenyl]-2,3,5,6-tetraphenylbenzene; or the like.

Further, as examples of the aromatic hydrocarbon which can be used for the composite material, the following can be given: 2-tert-butyl-9,10-di(2-naphthyl)anthracene (abbrev.: t-BuDNA); 2-tert-butyl-9,10-di(1-naphthyl)anthracene; 9,10-bis(3,5-diphenylphenyl)anthracene (abbrev.: DPPA); 2-tert-butyl-9,10-bis(4-phenylphenyl)anthracene (abbrev.: t-BuDBA); 9,10-di(2-naphthyl)anthracene (abbrev.: DNA); 9,10-diphenylanthracene (abbrev.: DPAnth); 2-tert-butylanthracene (abbrev.: t-BuAnth); 9,10-bis(4-methyl-1-naphthyl)anthracene (abbrev.: DMNA); 2-tert-butyl-9,10-bis[2-(1-naphthyl)phenyl]anthracene; 9,10-bis[2-(1-naphthyl)phenyl]anthracene; 2,3,6,7-tetramethyl-9,10-di(1-naphthyl)anthracene; 2,3,6,7-tetramethyl-9,10-di(2-naphthyl)anthracene; 9,9'-bianthryl; 10,10'-diphenyl-9,9'-bianthryl; 10,10'-bis(2-phenylphenyl)-9,9'-bianthryl; 10,10'-bis[(2,3,4,5,6-pentaphenyl)phenyl]-9,9'-bianthryl; anthracene; tetracene; rubrene; perylene; 2,5,8,11-tetra(tert-butyl)perylene; and the like. Besides the above, pentacene, coronene, or the like can also be used. As described above, an aromatic hydrocarbon which has a hole mobility of $1\times10^{-6}$ cm$^2$/Vs or more and of which the carbon number is 14 to 42 is more preferable.

Note that the aromatic hydrocarbon which can be used for the composite material may have a vinyl skeleton. As examples of the aromatic hydrocarbon having a vinyl group, 4,4'-bis(2,2-diphenylvinyl)biphenyl (abbrev.: DPVBi), 9,10-bis[4-(2,2-diphenylvinyl)phenyl]anthracene (abbrev.: DPVPA), and the like can be given, for example.

Further, a high molecular weight compound such as poly(N-vinylcarbazole) (abbrev.: PVK) or poly(4-vinyltriphenylamine) (abbrev.: PVTPA) can also be used.

As a material for forming the second layer 104, a material having a high hole transporting property, specifically, an aromatic amine compound (that is; a compound having a benzene ring-nitrogen bond) is preferable. As examples of the material which are widely used, the following can be given: 4,4'-bis[N-(3-methylphenyl)-N-phenylamino]biphenyl; a derivative thereof such as 4,4'-bis[N-(1-napthyl)-N-phenylamino]biphenyl (hereinafter referred to as NPB); and a starburst aromatic amine compound such as 4,4',4''-tris(N,N-diphenyl-amino)triphenylamine and 4,4',4''-tris[N-(3-methylphenyl)-N-phenylamino]triphenylamine. These materials described here are mainly materials each having a hole mobility of $10^{-6}$ cm$^2$/Vs or more. Further, other materials than these may also be used as long as they are materials in which a hole transporting property is higher than an electron transporting property. The second layer 104 is not limited to being a single layer and may be a mixed layer of any of the aforementioned materials or a stacked layer which includes two or more layers each containing the aforementioned material.

The third layer 105 is a layer containing a light emitting material. In this embodiment mode, the third layer 105 contains the quinoxaline derivative of the present invention described in Embodiment Mode 1. The quinoxaline derivative of the present invention, which emits light in blue to blue-green color region, can favorably be applied to a light emitting element as a light emitting material.

As the fourth layer 106, a material having a high electron transporting property can be used. For example, a layer containing a metal complex or the like including a quinoline or benzoquinoline skeleton, such as tris(8-quinolinolato)aluminum (abbrev.: Alq), tris(4-methyl-8-quinolinolato)aluminum (abbrev.: Almq$_3$), bis(10-hydroxybenzo[h]quinolinato)beryllium (abbrev.: BeBq$_2$), or bis(2-methyl-8-quinolinolato)(4-phenylphenolato)aluminum (abbrev.: BAlq) can be used. Alternatively, a metal complex or the like including an oxazole-based or thiazole-based ligand, such as bis[2-(2-hydroxyphenyl)benzoxazolato]zinc (abbrev.: Zn(BOX)$_2$) or bis[2-(2-hydroxyphenyl)-benzothiazolato]zinc (abbrev.: Zn(BTZ)$_2$) can be used. Besides the above metal complexes, the following can be used: 2-(4-biphenylyl)-5-(4-tert-butylphenyl)-1,3,4-oxadiazole (abbrev.: PBD); 1,3-bis[5-(p-tert-butylphenyl)-1,3,4-oxadiazol-2-yl]benzene (abbrev.: OXD-7); 3-(4-biphenylyl)-4-phenyl-5-(4-tert-butylphenyl)-1,2,4-triazole (abbrev.: TAZ), bathophenanthroline (abbrev.: BPhen); bathocuproine (abbrev.: BCP); or the like. These materials described here are mainly materials each having an electron mobility of $10^{-6}$ cm$^2$/Vs or more. Further, other materials than these may also be used as the electron transporting layer as long as they are materials in which an electron transporting property is higher than a hole transporting property. The electron transporting layer is not limited to being a single layer and may be a stacked layer which includes two or more layers each containing the aforementioned material.

As the second electrode 107, the following can be used: a metal, an alloy, a conductive compound, or a mixture thereof, having a low work function (specifically, 3.8 eV or lower). As specific examples of such a cathode material, the following can be given: an element in Group 1 or 2 of the Periodic Table of the Elements, that is, an alkali metal such as lithium (Li) or cesium (Cs), an alkaline earth metal such as magnesium (Mg), calcium (Ca), or strontium (Sr), and an alloy containing these metals (e.g., MgAg or AlLi). In addition, a rare earth metal such as europium (Eu) or ytterbium (Yb), an alloy containing these rare earth metals, and the like can be given. However, by providing a layer having a function to promote electron injection between the second electrode 107 and the fourth layer 106 so as to be stacked on the second electrode 107, various conductive materials such as Al, Ag, ITO, or ITO containing silicon or silicon oxide can be used as the second electrode 107, regardless of the value of the work function.

As the layer having a function of promoting electron injection, an alkali metal, an alkaline earth metal, or a compound thereof such as lithium fluoride (LiF), cesium fluoride (CsF), or calcium fluoride ($CaF_2$) can be used. For example, a layer made of a material having an electron transporting property, which contains an alkali metal, an alkaline earth metal, or a compound thereof (e.g., a layer of Alq containing magnesium (Mg)) can be used. It is preferable to use such a layer as the electron injection layer since electron injection from the second electrode 107 is efficiently performed.

Various methods can be used for forming the first layer 103, the second layer 104, the third layer 105, and the fourth layer 106. For example, an evaporation method, an ink-jet method, a spin coating method, or the like can be used. Furthermore, each electrode or each layer may be formed by a different film formation method.

In the light emitting element of the present invention having the structure as set forth above, current flows due to potential difference between the first electrode 102 and the second electrode 107 and holes and electrons are recombined in the third layer 105 containing the material having a high light emitting property, whereby light emission is performed. That is, a light emitting region is formed in the third layer 105.

Figure 1B:
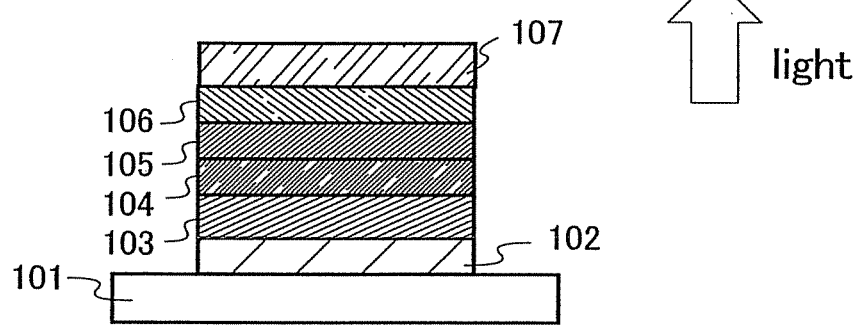
Figure 1C:
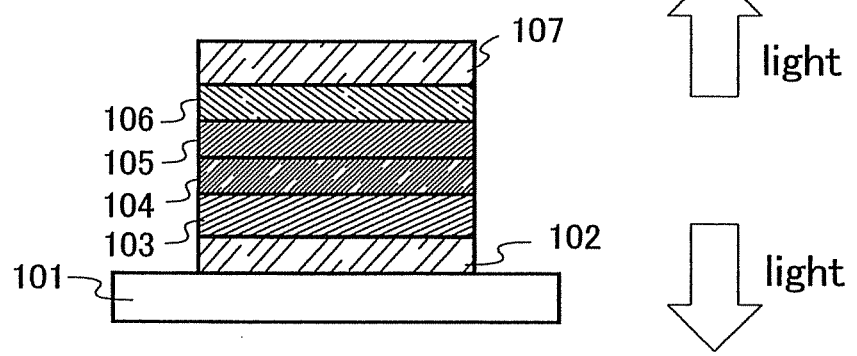

Light emission is extracted outside through either one or both of the first electrode 102 and the second electrode 107. Therefore, either one or both of the first electrode 102 and the second electrode 107 is/are formed using an electrode having a light transmitting property. In the case where only the first electrode 102 has a light transmitting property, light emission is extracted from a substrate side through the first electrode 102 as shown in FIG. 1A. In the case where only the second electrode 107 is formed using an electrode having a light transmitting property, light emission is extracted from the side opposite to the substrate side through the second electrode 107 as shown in FIG. 1B. In the case where both of the first electrode 102 and the second electrode 107 are each an electrode having a light transmitting property, light emission is extracted from both the substrate side and the side opposite to the substrate side through the first electrode 102 and the second electrode 107, as shown in FIG. 1C.

A layer structure provided between the first electrode 102 and the second electrode 107 is not limited to the above-described one. Any layer structure can be employed as long as a light emitting region, in which holes and electrons are recombined, is provided away from the first electrode 102 and the second electrode 107, so as to prevent a quenching phenomenon caused by the light emitting region and a metal being located close to each other.

That is, a stacked-layer structure of the layers is not particularly limited, and layers formed of a material having a high electron transporting property, a material having a high hole transporting property, a material having a high electron injecting property, a material having a high hole injecting property, a bipolar material (a material having a high electron transporting property and a high hole transporting property), a hole blocking material, or the like may be freely combined with the quinoxaline derivative of the present invention.

Figure 2:
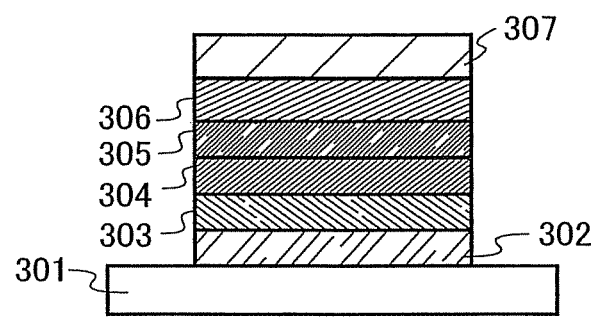
FIG. 2 is a diagram showing a light emitting element of the present invention.

A light emitting element shown in FIG. 2 has a structure in which a first electrode 302 functioning as a cathode, a first layer 303 formed of a material having a high electron transporting property, a second layer 304 containing a light emitting material, a third layer 305 formed of a material having a high hole transporting property, a fourth layer 306 formed of a material having a high hole injecting property, and a second electrode 307 functioning as an anode are sequentially stacked over a substrate 301.

In this embodiment mode, a light emitting element is manufactured over a substrate made of glass, plastic, or the like. By manufacturing a plurality of the light emitting elements described above over one substrate, a passive matrix light emitting device can be manufactured. Alternatively, for example, a thin film transistor (TFT) may be formed over a substrate made of glass, plastic, or the like, and a light emitting element electrically connected to the TFT may be manufactured. Accordingly, an active matrix light emitting device in which driving of the light emitting element is controlled by the TFT can be manufactured. The structure of the TFT is not particularly limited, and a staggered TFT or an inverted staggered may be employed. Crystallinity of a semiconductor used for the TFT is also not particularly limited, and an amorphous semiconductor or a crystalline semiconductor may be used. Further, a driving circuit formed over a TFT substrate may include an N-channel TFT and a P-channel TFT or may include either an N-channel TFT or a P-channel TFT.

As shown in this embodiment mode, the quinoxaline derivative of the present invention can be used for a light emitting layer without including any other light emitting material since the quinoxaline derivative is bipolar and has a light emitting property.

Further, since the quinoxaline derivative of the present invention is bipolar, a light emitting element in which a light emitting region is rarely located at an interface of stacked films and which shows favorable characteristics with few changes in the light emission spectrum and little decrease in light emission efficiency due to an interaction such as an exciplex can be manufactured.

Further, an amorphous film can be obtained, in which the amount of microcrystalline components included during film formation is very small and that included in the film formed is small. That is, the film quality is good; therefore, a light emitting element with few element defects such as dielectric breakdown due to electric field concentration can be manufactured.

Further, by using the quinoxaline derivative of the present invention, which is a material which is bipolar and excellent in carrier transporting property (electron transporting property and hole transporting property), for a light emitting element, a driving voltage of the light emitting element can be reduced and thus the power consumption can be reduced.

Further, by using the quinoxaline derivative of the present invention, which has a high glass transition point, a light emitting element having high heat resistance can be obtained.

Further, the quinoxaline derivative of the present invention is stable even when an oxidation reaction and a reduction reaction are repeated alternatingly. That is, the quinoxaline derivative is electrochemically stable. Therefore, by using the quinoxaline derivative of the present invention, a long-life light emitting element can be obtained.

(Embodiment Mode 3)

In this embodiment mode, a light emitting element having a different structure from Embodiment Mode 2 is described.

By applying a structure in which the quinoxaline derivative of the present invention is dispersed in another material to the third layer 105 described in Embodiment Mode 2, light emission from the quinoxaline derivative of the present invention can be obtained. A light emitting element which emits light in blue to blue-green color region can be obtained since the quinoxaline derivative of the present invention emits light in blue to blue-green color region.

Here, various materials can be used as the material in which the quinoxaline derivative of the present invention is dispersed. In addition to the materials having a high hole transporting property and the materials having a high electron transporting property, which are described in Embodiment Mode 2, the following can be given: 4,4'-di(N-carbazolyl)-biphenyl (abbrev.: CBP); 2,2',2"-(1,3,5-benzenetri-yl)-tris[1-phenyl-1H-benzimidazole] (abbrev.: TPBI); 9,10-di(2-naphthyl)anthracene (abbrev.: DNA); 2-tert-butyl-9,10-di(2-naphthyl)anthracene (abbrev.: t-BuDNA); and the like.

By using the quinoxaline derivative of the present invention, which is a material which is bipolar and excellent in carrier transporting property (electron transporting property and hole transporting property), for a light emitting element, a driving voltage of the light emitting element can be reduced and thus the power consumption can be reduced.

Further, by using the quinoxaline derivative of the present invention, which has a high glass transition point, a light emitting element having high heat resistance can be obtained.

Further, the quinoxaline derivative of the present invention is stable even when an oxidation reaction and a reduction reaction are repeated alternatingly. That is, the quinoxaline derivative is electrochemically stable. Therefore, by using the quinoxaline derivative of the present invention, a long-life light emitting element can be obtained.

It is to be noted that the structure described in Embodiment Mode 2 can be used as appropriate for layers other than the third layer 105.

(Embodiment Mode 4)

In this embodiment mode, a light emitting element having a different structure from Embodiment Modes 2 and 3 is described.

By applying a structure in which a light emitting material is dispersed in the quinoxaline derivative of the present invention to the third layer 105 described in Embodiment Mode 2, light emission from the light emitting material can be obtained.

The quinoxaline derivative of the present invention, which is bipolar and has favorable film quality since the amount of microcrystalline components contained during film formation is very small, can be preferably used as the material in which another light emitting material is dispersed.

In the case where the quinoxaline derivative of the present invention is used as the material in which another light emitting material is dispersed, a light emission color depending on the light emitting material can be obtained. Further, a mixed color of a light emission color depending on the quinoxaline derivative of the present invention and a light emission color depending on the light emitting material dispersed in the quinoxaline derivative can also be obtained.

Here, various materials can be used as the light emitting material dispersed in the quinoxaline derivative of the present invention. Specifically, a fluorescent material can be used such as 4-(dicyanomethylene)-2-methyl-6-(p-dimethylaminostyryl)-4H-pyran (abbrev.: DCM1), 4-(dicyanomethylene)-2-methyl-6-(julolidine-4-yl-vinyl)-4H-pyran (abbrev.: DCM2), N,N-dimethylquinacridone (abbrev.: DMQd), 9,10-diphenylanthracene (abbrev.: DPA), 5,12-diphenyltetracene (abbrev.: DPT), coumarin 6, perylene, or rubrene. Further, a phosphorescent material can also be used such as bis(2-phenylbenzothiazolato-N,$C^{2'}$]iridium (III) acetylacetonato (abbrev.: Ir(bt)$_2$(acac)), tris(2-phenylquinolinolato-N,$C^{2'}$]iridium (III) (abbrev.: Ir(pq)$_3$), bis(2-phenylquinolinolato-N,$C^{2'}$]iridium (III) acetylacetonato (abbrev.: Ir(pq)$_2$(acac)), bis[2-(2'-benzo[4,5-α]thienyl)pyridinato-N,$C^{3'}$]iridium (III) acetylacetonato (abbrev.: Ir(btp)$_2$(acac)), bis(1-phenylisoquinolinolato-N,$C^{2'}$]iridium (III) acetylacetonato (abbrev.: Ir(piq)$_2$(acac)), (acetylacetonato)bis[2,3-bis(4-fluorophenyl)quinoxalinato]iridium (III) (abbrev.: Ir(Fdpq)$_2$(acac)), or 2,3,7,8,12,13,17,18-octaethyl-21H,23H-porphyrinplatinum (II) (abbrev.: PtOEP).

Note that in the case of using the phosphorescent material as the light emitting material dispersed in the quinoxaline derivative of the present invention, it is preferable that a light emission spectrum of the phosphorescent material have a peak at 560 ran to 700 nm (both inclusive). In the case of using the fluorescent material as the light emitting material dispersed in the quinoxaline derivative of the present invention, it is preferable that a light emission spectrum of the fluorescent material have a peak at 500 nm to 700 nm (both inclusive), and more preferably a peak at 500 nm to 600 nm (both inclusive).

By using the quinoxaline derivative of the present invention, which is a material which is bipolar and excellent in carrier transporting property (electron transporting property and hole transporting property), for a light emitting element, a driving voltage of the light emitting element can be reduced.

Further, by using the quinoxaline derivative of the present invention, which has a high glass transition point, a light emitting element having high heat resistance can be obtained.

Further, the quinoxaline derivative of the present invention is stable even when an oxidation reaction and a reduction reaction are repeated alternatingly. That is, the quinoxaline derivative is electrochemically stable. Therefore, by using the quinoxaline derivative of the present invention, a long-life light emitting element can be obtained.

It is to be noted that the structure described in Embodiment Mode 2 can be used as appropriate for layers other than the third layer 105.

(Embodiment Mode 5)

In this embodiment mode, a light emitting element in which a plurality of light emitting units according to the present invention is stacked (hereinafter, referred to as a stacked element) is described with reference to FIG. 3. This light emitting element is a light emitting element that includes a plurality of light emitting units between a first electrode and a second electrode.

Figure 3:
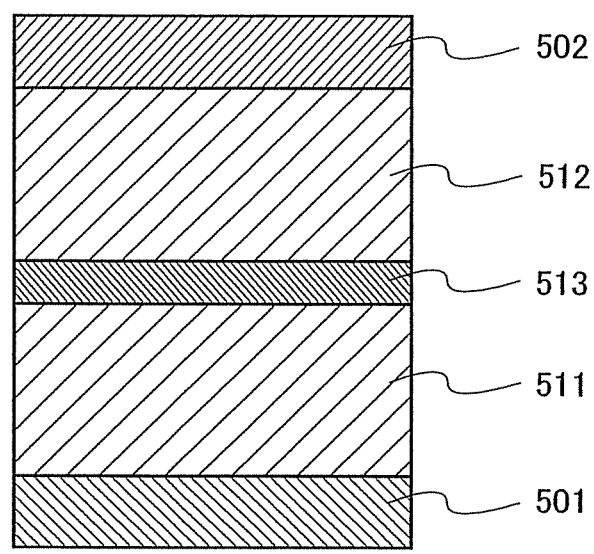
FIG. 3 is a diagram showing a light emitting element of the present invention.

In FIG. 3, a first light emitting unit 511 and a second light emitting unit 512 are stacked between a first electrode 501 and a second electrode 502. Electrodes similar to those described in Embodiment Mode 2 can be applied to the first electrode 501 and the second electrode 502. The first light emitting unit 511 and the second light emitting unit 512 may have the same structure or different structures, and a structure similar to any of those described in Embodiment Modes 2 to 4 can be applied.

A charge generation layer 513 contains a composite material of an organic compound and a metal oxide. The composite material of an organic compound and a metal oxide is described in Embodiment Mode 2, and contains an organic compound and a metal oxide such as $V_2O_5$, $MoO_3$, or $WO_3$. As the organic compound, various compounds such as an aromatic amine compound, a carbazole derivative, an aromatic hydrocarbon, and a high molecular compound (e.g., an oligomer, a dendrimer, or a polymer) can be used. Note that it is preferable that an organic compound having a hole mobility of $10^{-6}$ cm$^2$/Vs or more be applied as the hole-transporting organic compound. Further, other materials than these may also be used as long as they are materials in which a hole transporting property is higher than an electron transporting property. The composite material of an organic compound and a metal oxide is excellent in carrier injecting property and carrier transporting property, and accordingly, low-voltage driving and low-current driving can be realized.

It is to be noted that the charge generation layer 513 may also be formed of a combination of a composite material of an organic compound and a metal oxide and another material. For example, the charge generation layer 513 may be formed of a combination of a layer containing the composite material of an organic compound and a metal oxide and a layer containing a compound selected from electron donating materials and a compound having a high electron transporting property. Further, the charge generation layer 513 may also be formed of a combination of a layer containing the composite material of an organic compound and a metal oxide and a transparent conductive film.

In any case, it is necessary that the charge generation layer 513 interposed between the first light emitting unit 511 and the second light emitting unit 512 inject electrons to one light emitting unit and inject holes to the other light emitting unit when a voltage is applied between the first electrode 501 and the second electrode 502.

In this embodiment mode, the light emitting element having two light emitting units is explained; however, the present invention can also be applied to a light emitting element in which three or more light emitting units are stacked together. By disposing a plurality of light emitting units between a pair of electrodes in such a manner that the plurality of light emitting units is partitioned with a charge generation layer as is in the light emitting element according to this embodiment mode, a long-life light emitting element by which high luminance emission can be realized at a low current density can be realized. Further, when the present invention is applied to lighting, voltage drop due to resistance of an electrode material can be reduced, and therefore, uniform light emission in a large area can be realized. In addition, a light emitting device capable of low-voltage driving and with low power consumption can be realized.

This embodiment mode can be combined as appropriate with another embodiment mode.
(Embodiment Mode 6)

In this embodiment mode, a light emitting device manufactured using the quinoxaline derivative of the present invention is described with reference to FIGS. 4A and 4B.

Figure 4A:
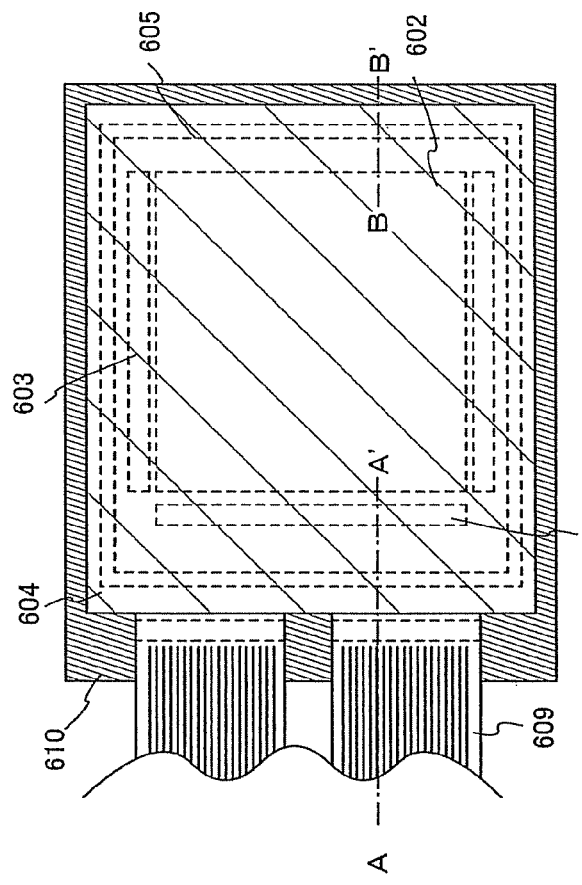
FIGS. 4A and 4B are diagrams showing a light emitting device of the present invention.
Figure 4B:
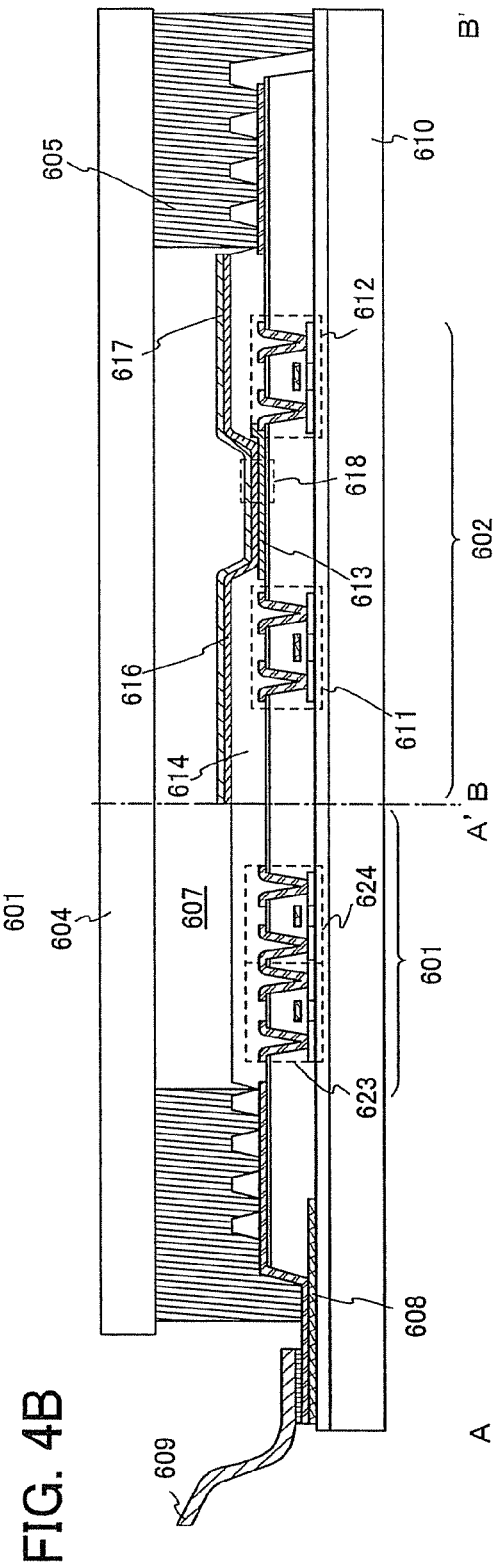

FIG. 4A is a top-view diagram showing the light emitting device, and FIG. 4B is a cross-sectional diagram of FIG. 4A taken along lines A-A' and B-B'. A driver circuit portion (a source side driver circuit), a pixel portion, and a driver circuit portion (a gate side driver circuit) are denoted by reference numerals 601, 602, and 603, respectively, and are indicated by using a dotted line. Also, a sealing substrate and a sealing material are denoted by reference numerals 604 and 605, respectively, and a portion enclosed by the sealing material 605 corresponds to a space 607.

Note that a leading wiring 608 is a wiring for transmitting signals to be input to the source side driver circuit 601 and the gate side driver circuit 603, and this wiring 608 receives a video signal, a clock signal, a start signal, a reset signal, and the like from an FPC (flexible printed circuit) 609 that is an external input terminal. It is to be noted that Only the FPC is shown here; however, the FPC may be provided with a printed wiring board (PWB). The light emitting device in this specification includes not only a main body of a light emitting device but also a light emitting device provided with an FPC or a PWB.

Next, a cross-sectional structure thereof is described with reference to FIG. 4B. The driver circuit portions and the pixel portion are formed over an element substrate 610. Here, the source side driver circuit 601, which is one driver circuit portion, and one pixel in the pixel portion 602 are shown.

A CMOS circuit, which is a combination of an N-channel TFT 623 and a P-channel TFT 624, is formed as the source side driver circuit 601. The driver circuit may be formed of any of various CMOS circuits, PMOS circuits, and NMOS circuits. Although a driver-integration type device, in which a driver circuit is formed over a substrate, is described in this embodiment mode, a driver circuit is not necessarily formed over a substrate and can be formed externally as well. Further, the crystallinity of a semiconductor used for the TFT is not particularly limited, and either an amorphous semiconductor or a crystalline semiconductor may be used.

Further, the pixel portion 602 includes a plurality of pixels each including a switching TFT 611, a current controlling TFT 612, and a first electrode 613 which is electrically connected to a drain of the current controlling TFT 612. Note that an insulator 614 is formed so as to cover an edge portion of the first electrode 613. Here, a positive photosensitive acrylic resin film is used for the insulator 614.

The insulator 614 is formed so as to have a curved surface having curvature at an upper end portion or a lower end portion thereof in order to obtain favorable coverage. For example, in the case of using a positive photosensitive acrylic resin as a material for the insulator 614, the insulator 614 is preferably formed so as to have a curved surface with a curvature radius (0.2-3 μm) only at the upper end portion thereof. Either a negative type resin which becomes insoluble in an etchant by light irradiation or a positive type resin which becomes soluble in an etchant by light irradiation can be used for the insulator 614.

An EL layer 616 and a second electrode 617 are formed over the first electrode 613. Here, a material having a large work function is preferably used as a material for the first electrode 613 functioning as an anode. For example, the first electrode 613 can be formed of, as well as a single-layer film such as an ITO film, an indium tin oxide film containing silicon, an indium oxide film containing zinc oxide at 2 wt % to 20 wt %, a titanium nitride film, a chromium film, a tungsten film, a Zn film, or a Pt film; a stacked layer of a titanium nitride film and a film containing aluminum as its main component; a three-layer film of a titanium nitride film, a film containing aluminum as its main component, and a titanium nitride film; or the like. Note that when a stacked-layer structure is employed for the first electrode 613, the first electrode 613 is low in resistance as a wring and forms a good ohmic contact, and further, can serve as an anode.

Further, the EL layer 616 is formed by various methods such as an evaporation method using an evaporation mask, an ink-jet method, and a spin coating method. The EL layer 616 contains the quinoxaline derivative of the present invention described in Embodiment Mode 1. Further, as another material forming the EL layer 616, a low molecular weight compound or a high molecular weight compound (e.g., an oligomer or a dendrimer) may be used.

Further, as a material used for the second electrode 617, which is formed over the EL layer 616 and serves as a cathode, a material having a small work function (e.g., Al, Mg, Li, Ca, or an alloy or a compound thereof such as MgAg, MgIn, AlLi, LiF, or $CaF_2$) is preferably used. In the case where light generated in the EL layer 616 is transmitted through the second electrode 617, a stacked layer of a metal thin film and a transparent conductive film (which is made of ITO, indium oxide containing zinc oxide at 2 wt % to 20 wt %, indium oxide-tin oxide containing silicon or silicon oxide, zinc oxide (ZnO), or the like) is preferably used as the second electrode 617.

By attachment of the sealing substrate 604 to the element substrate 610 with the sealing material 605, a light emitting element 618 is provided in the space 607 enclosed by the element substrate 610, the sealing substrate 604, and the sealing material 605. Note that the space 607 is filled with a filling material; alternatively, it may be filled with an inert gas (e.g., nitrogen or argon) or may be filled with the sealing material 605.

Note that an epoxy-based resin is preferably used as the sealing material 605. Further, it is preferable that the material transmit as little moisture and oxygen as possible. As the sealing substrate 604, a plastic substrate made of FRP (Fiber-glass-Reinforced Plastics), PVF (polyvinyl fluoride), polyester, an acrylic resin, or the like can be used as well as a glass substrate or a quartz substrate.

Through the above-described process, a light emitting device manufactured using the quinoxaline derivative of the present invention can be obtained.

Since the quinoxaline derivative described in Embodiment Mode 1 is employed for the light emitting device of the present invention, a light emitting device having good characteristics can be obtained. Specifically, a light emitting device having high heat resistance can be obtained.

Further, since the quinoxaline derivative of the present invention is electrochemically stabile, a long-life light emitting device can be obtained.

In addition, since the quinoxaline derivative of the present invention is bipolar and is superior in carrier transporting property (electron transporting property and hole transporting property), a driving voltage of a light emitting element and power consumption of a light emitting device can be reduced by use of the quinoxaline derivative of the present invention. In particular, when a phosphorescent material is used as a light emitting material, a light emitting device with high light emission efficiency and further reduced power consumption can be obtained.

Figure 5A:
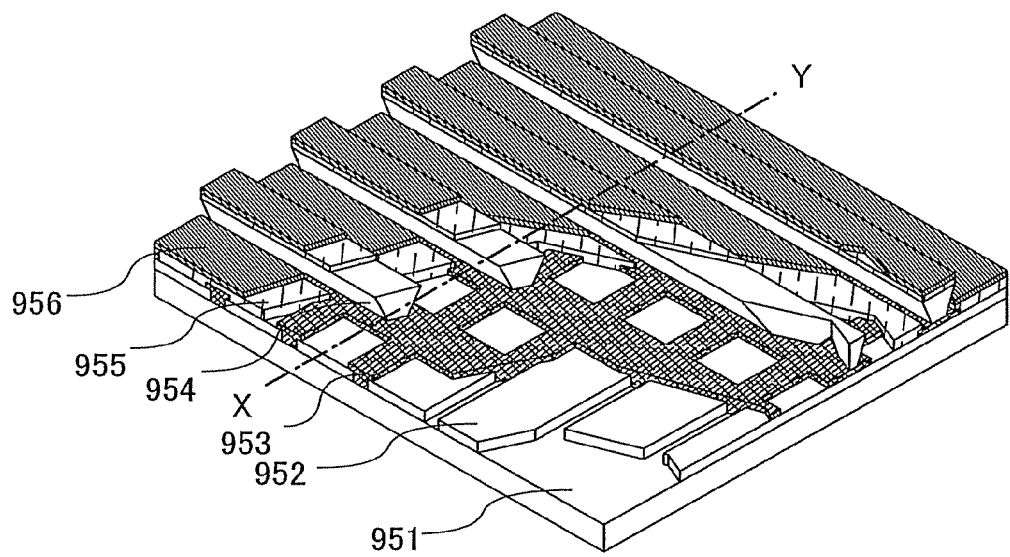
FIGS. 5A and 5B are diagrams showing a light emitting device of the present invention.
Figure 5B:
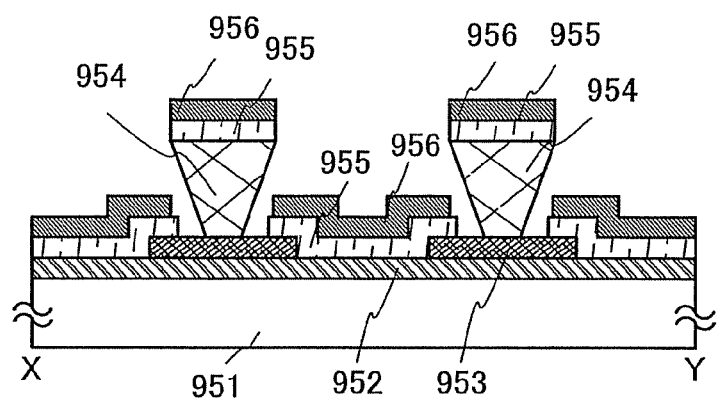

As described above, an active matrix light emitting device in which driving of a light emitting element is controlled by a transistor is described in this embodiment mode. Alternatively, a passive matrix light emitting device may be manufactured. FIGS. 5A and 5B are perspective diagrams of a passive matrix light emitting device which is manufactured by applying the present invention. In FIGS. 5A and 5B, an EL layer 955 is provided between electrodes 952 and 956 over a substrate 951. An edge of the electrode 952 is covered with an insulating layer 953. Then, a partition layer 954 is provided over the insulating layer 953. A side wall of the partition layer 954 slopes so that a distance between one side wall and the other side wall is narrower toward a substrate surface. In other words, a cross section of the partition layer 954 in the direction of a short side is trapezoidal, and a base (a side extending in a similar direction as a plane direction of the insulating layer 953 and in contact with the insulating layer 953) is shorter than an upper side (a side extending in a similar direction as the plane direction of the insulating layer 953 and not in contact with the insulating layer 953). By thus providing the partition layer 954, a defect of a light emitting element caused by static electricity or the like can be prevented. Further, also in a passive matrix light emitting device, low power consumption driving can be realized by containing the light emitting element of the present invention, which is operated at low driving voltage.

(Embodiment Mode 7)

In this embodiment mode, an electronic device of the present invention, including the light emitting device described in Embodiment Mode 6 is described. The electronic device of the present invention contains the quinoxaline derivative described in Embodiment Mode 1 and has a display portion that has high heat resistance. Further, a long-life display portion is provided. Further, a display portion with reduced power consumption is provided.

As examples of an electronic device including a light emitting element manufactured using the quinoxaline derivative of the present invention, a camera such as a video camera or a digital camera, a goggle type display, a navigation system, an audio reproducing device (e.g., a car audio system or an audio component system), a computer, a game machine, a portable information terminal (e.g., a mobile computer, a mobile phone, a portable game machine, or an electronic book), an image reproducing device provided with a recording medium (specifically, a device capable of reproducing a recording medium such as a Digital Versatile Disc (DVD) and provided with a display device that can display the image), and the like are given. Specific examples of these electronic devices are shown in FIGS. 6A to 6D.

Figure 6A:
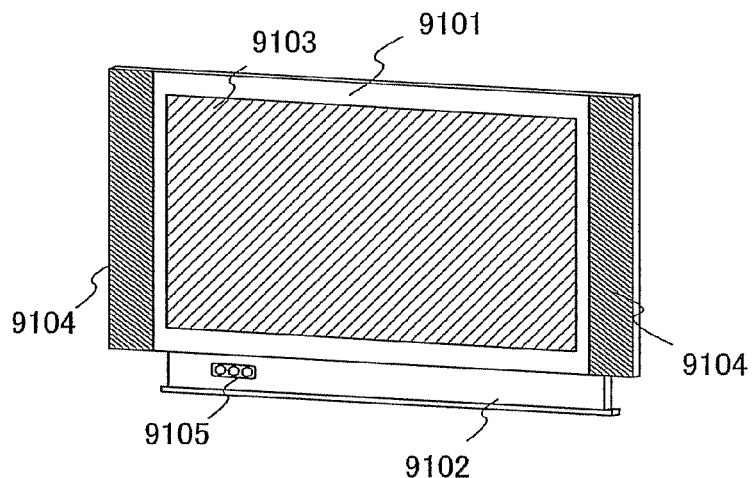
FIGS. 6A to 6D are diagrams each showing an electronic device of the present invention.

FIG. 6A shows a television device according to the present invention, which includes a housing 9101, a supporting base 9102, a display portion 9103, a speaker portion 9104, a video input terminal 9105, and the like. In the television device, the display portion 9103 includes light emitting elements similar to any of those described in Embodiment Modes 2 to 5, arranged in matrix. The light emitting element has features in that low voltage driving can be performed and the life is long. Further, there is also a feature in that the heat resistance is high. The display portion 9103 including the light emitting elements has similar features. Therefore, in the television device, image degradation is suppressed and low power consumption is achieved. Due to such features, a deterioration compensation function and a power supply circuit can be significantly reduced or downsized in the television device, which enables reduction in size and weight of the housing 9101 and the supporting base 9102. In the television device according to the present invention, low power consumption, high image quality, and small size and lightweight are achieved; therefore, a product which is suitable for living environment can be provided.

Figure 6B:
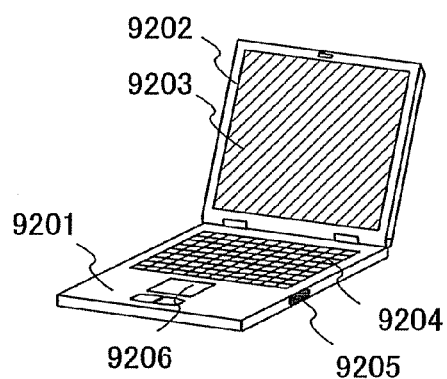

FIG. 6B shows a computer according to the present invention, which includes a main body 9201, a housing 9202, a display portion 9203, a keyboard 9204, an external connection port 9205, a pointing device 9206, and the like. In the computer, the display portion 9203 includes light emitting elements similar to any of those described in Embodiment Modes 2 to 5, arranged in matrix. The light emitting element has features in that low voltage driving can be performed and the life is long. Further, there is also a feature in that the heat resistance is high. The display portion 9203 including the light emitting elements has similar features. Therefore, in the computer, image degradation is suppressed and low power consumption is achieved. Due to such features, a deterioration compensation function and a power supply circuit can be significantly reduced or downsized in the computer, which enables reduction in size and weight of the main body 9201 and the housing 9202. In the computer according to the present invention, low power consumption, high image quality, and small size and lightweight are achieved; therefore, a product which is suitable for environment can be provided.

Figure 6C:
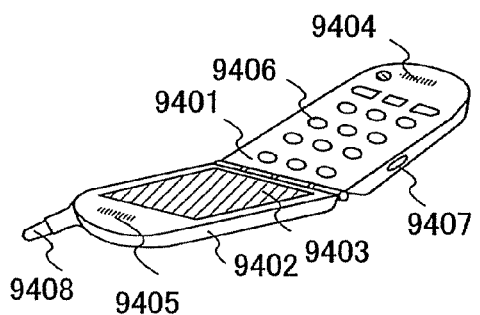

FIG. 6C shows a mobile phone according to the present invention, which includes a main body 9401, a housing 9402, a display portion 9403, an audio input portion 9404, an audio output portion 9405, an operation key 9406, an external connection port 9407, an antenna 9408, and the like. In the mobile phone, the display portion 9403 includes light emitting elements similar to any of those described in Embodiment Modes 2 to 5, arranged in matrix. The light emitting element has features in that low voltage driving can be performed and the life is long. Further, there is also a feature in that the heat resistance is high. The display portion 9403 including the light emitting elements has similar features. Therefore, in the mobile phone, image degradation is suppressed and low power consumption is achieved. Due to such features, a deterioration compensation function and a power supply circuit can be significantly reduced or downsized in the mobile phone, which enables reduction in size and weight of the main body 9401 and the housing 9402. In the mobile phone according to the present invention, low power consumption, high image quality, and small size and lightweight are achieved; therefore, a product which is suitable for mobile use can be provided.

Figure 6D:
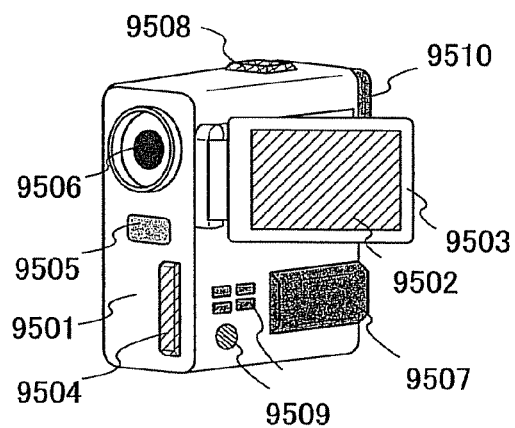

FIG. 6D shows a camera according to the present invention, which includes a main body 9501, a display portion 9502, a housing 9503, an external connection port 9504, a remote control receiving portion 9505, an image receiving portion 9506, a battery 9507, an audio input portion 9508, operation keys 9509, an eye piece portion 9510, and the like. In the camera, the display portion 9502 includes light emitting elements similar to any of those described in Embodiment Modes 2 to 5, arranged in matrix. The light emitting element has features in that low voltage driving can be performed and the life is long. Further, there is also a feature in that the heat resistance is high. The display portion 9502 including the light emitting elements has similar features. Therefore, in the camera, image degradation is suppressed and low power consumption is achieved. Due to such features, a deterioration compensation function and a power supply circuit can be significantly reduced or downsized in the camera, which enables reduction in size and weight of the main body 9501. In the camera according to the present invention, low power consumption, high image quality, and small size and lightweight are achieved; therefore, a product which is suitable for mobile use can be provided.

As described above, the applicable range of the light emitting device of the present invention is so wide that the light emitting device can be applied to electronic devices in various fields. By using the quinoxaline derivative of the present invention, an electronic device which has a display portion with low power consumption, a long life, and high heat resistance can be provided.

Further, the light-emitting device of the present invention can also be used as a lighting device. One mode where the light emitting element of the present invention is used as a lighting device is described with reference to FIG. 7.

Figure 7:
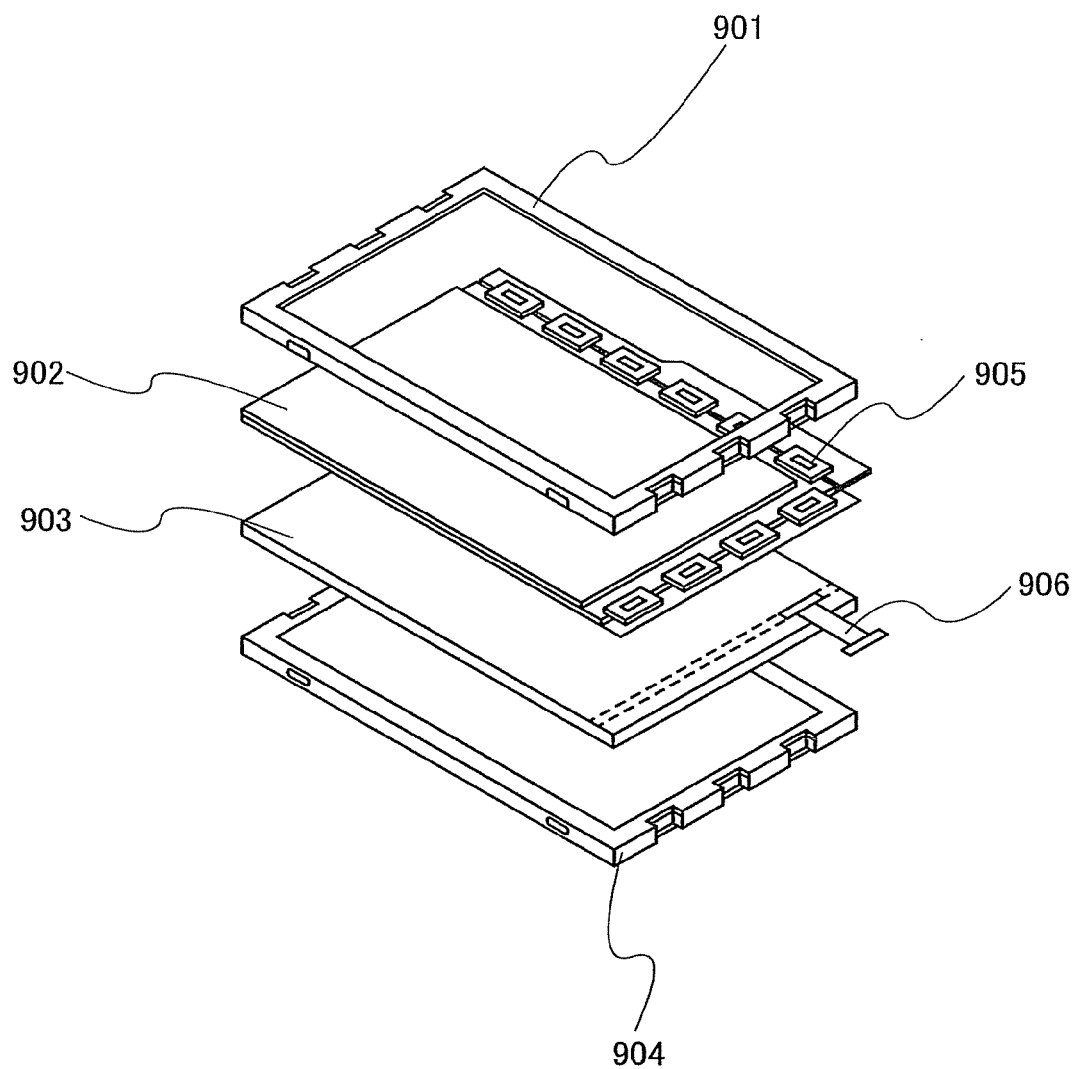
FIG. 7 is a diagram showing an electronic device of the present invention.

FIG. 7 shows an example of a liquid crystal display device using the light emitting device of the present invention as a backlight. The liquid crystal display device shown in FIG. 7 includes a housing 901, a liquid crystal layer 902, a backlight 903, and a housing 904, and the liquid crystal layer 902 is connected to a driver IC 905. The light emitting device of the present invention is used for the backlight 903, and current is supplied through a terminal 906.

By using the light emitting device of the present invention as a backlight of a liquid crystal display device, the backlight with reduced power consumption can be obtained. Further, since the light emitting device of the present invention is a lighting device with plane light emission and can have a large area, the backlight can have a large area, and a liquid crystal display device having a large area can be obtained. Furthermore, since the light emitting device of the present invention is thin and the power consumption is low, reduction in thickness and power consumption of a display device can also be achieved. Further, since the light emitting device of the present invention has a long life and high heat resistance, a liquid crystal display device using the light emitting device of the present invention also has a long life and high heat resistance.

Figure 8:
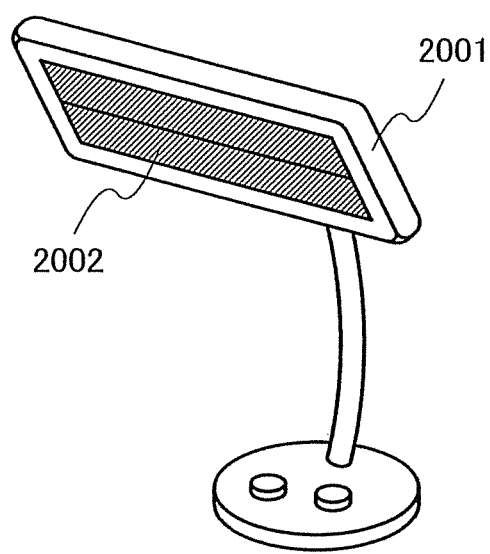
FIG. 8 is a diagram showing a lighting device of the present invention.

FIG. 8 shows an example where the light emitting device to which the present invention is applied is used as a table lamp that is a lighting device. A table lamp shown in FIG. 8 includes a housing 2001 and a light source 2002, and the light emitting device of the present invention is used as the light source 2002. Since the light emitting device of the present invention has high light emission efficiency and a long life, the table lamp also has high light emission efficiency and a long life.

Figure 9:
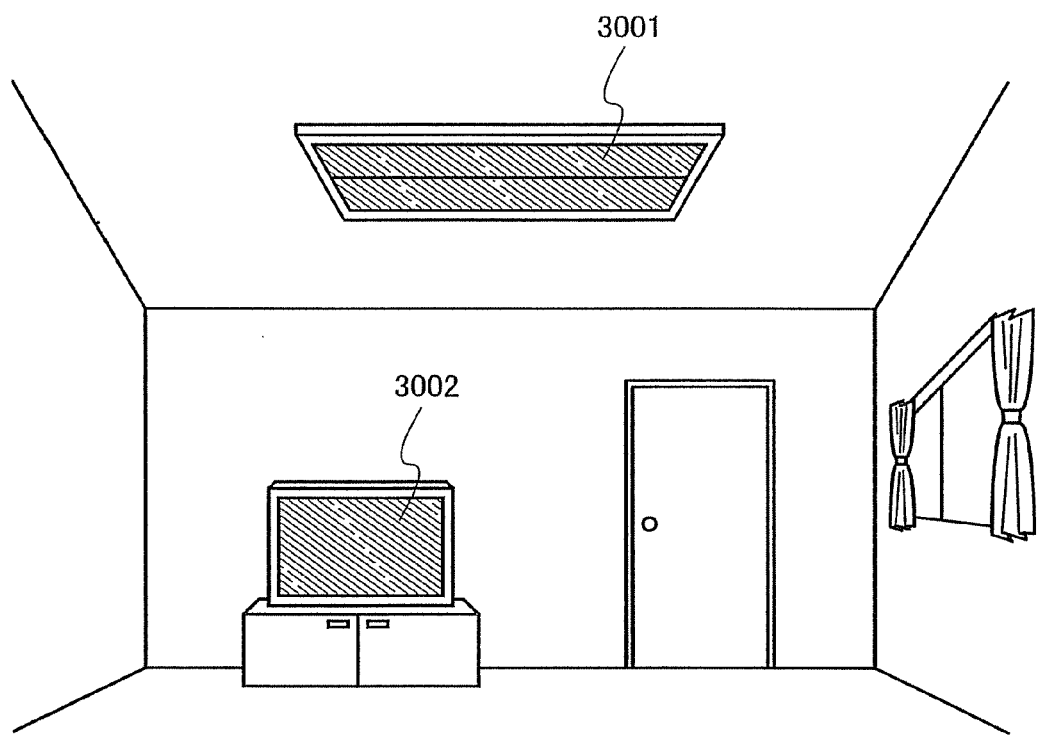
FIG. 9 is a diagram showing a lighting device of the present invention.

FIG. 9 shows an example where a light emitting device to which the present invention is applied is used as an indoor lighting device 3001. The light emitting device of the present invention which can also have a large area can be used as a lighting device having a large area. Further, the light emitting device of the present invention which is thin and of which power consumption is low can be used as a lighting device which is thin and of which power consumption is low. A television device 3002 according to the present invention, like that shown in FIG. 6A, is placed in a room where the light emitting device to which the present invention is applied is used as the indoor lighting device 3001, and public broadcasting and movies can be enjoyed. In such a case, since power consumption of both devices is small, dynamic images can be enjoyed in a bright room without any concern about an electricity bill.

(Embodiment Mode 8)

In this embodiment mode, an example of a mode where the quinoxaline derivative of the present invention is used for an active layer of a vertical transistor (SIT: Static Induction Transistor) which is one kind of an organic semiconductor element is described.

Figure 10:
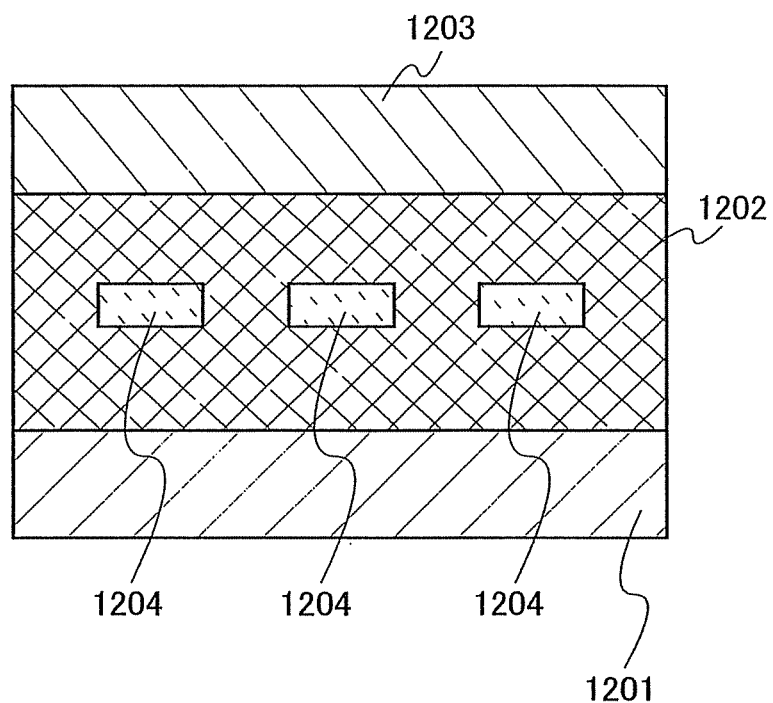
FIG. 10 is a cross-sectional diagram of an organic semiconductor element of the present invention.

The element has a structure in which a thin-film active layer 1202 containing the quinoxaline derivative of the present invention is interposed between a source electrode 1201 and a drain electrode 1203, and a gate electrode 1204 is embedded in the active layer 1202, as shown in FIG. 10. The gate electrode 1204 is electrically connected to a means for applying a gate voltage, and the source electrode 1201 and the drain electrode 1203 are electrically connected to a means for controlling the source-drain voltage.

In such an element structure, when a voltage is applied between source and drain under the condition where a gate voltage is not applied, a current flows (the state is an ON state). When a gate voltage is applied in this state, a depletion layer is generated in the periphery of the gate electrode 1204, whereby a current does not flow (the state is an OFF state). With the aforementioned mechanism, the element operates as a transistor.

In a vertical transistor, similarly to a light emitting element, a material which has both a carrier transporting property and an excellent film quality is required for an active layer. The quinoxaline derivative of the present invention is useful since it sufficiently meets this requirement.

(Embodiment 1)

In this embodiment, an example of a synthetic example of 2,3-bis[4-(4-diphenylaminophenyl)phenyl]quinoxaline (abbrev.: TPAPQ) is described in detail, which is the quinoxaline derivative of the present invention represented by the structural formula (11).

(11)

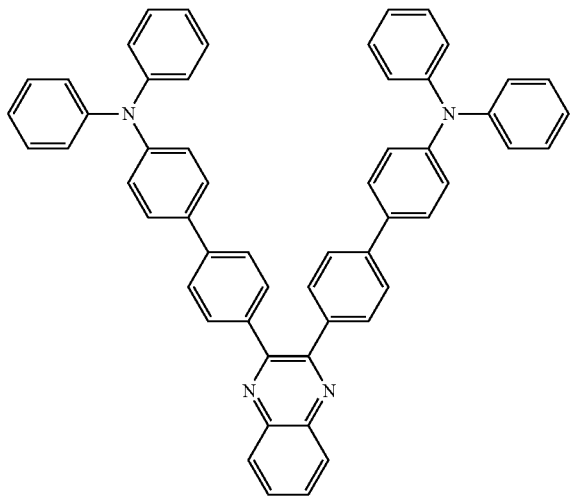

[Step 1] Synthesis of 2,3-bis(4-bromophenyl)quinoxaline

A synthesis method of 2,3-bis(4-bromophenyl)quinoxaline is described. A synthesis scheme of 2,3-bis(4-bromophenyl)quinoxaline is shown in (B-1).

(B-1)

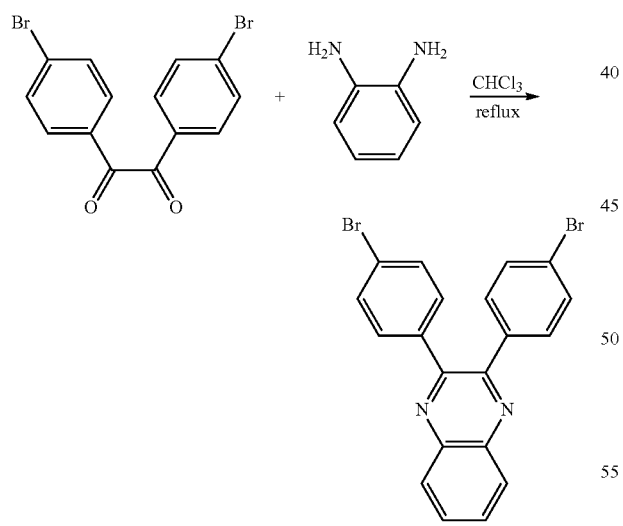

Under a stream of nitrogen, 30.2 g (82.0 mmol) of 4,4'-dibromobenzil, 9.31 g (86.1 mmol) of 1,2-phenylenediamine, and 300 mL of chloroform were put into a 500-mL three-neck flask and a reflux thereof was performed at 80° C. for 5 hours. After the reaction, the reaction solution was cooled to room temperature and washed with water. An aqueous layer was extracted with chloroform and dried with magnesium sulfate together with an organic layer. After the drying, the mixture was suctioned and filtrated, and the filtrate was enriched. The obtained solid was dissolved in toluene, and the resulting solution was subjected to suction filtration with florisil, celite, and alumina. The filtrate was enriched, whereby 30.0 g of a white powder solid of 2,3-bis(4-bromophenyl)quinoxaline that was a subject matter was obtained at a yield of 99%.

[Step 2] Synthesis of 4,4'-(quinoxaline-2,3-diyl)diphenylboronic acid

A synthesis method of 4,4'-(quinoxaline-2,3-diyl)diphenylboronic acid is described. A synthesis scheme of 4,4'-(quinoxaline-2,3-diyl)diphenylboronic acid is shown in (B-2).

(B-2)

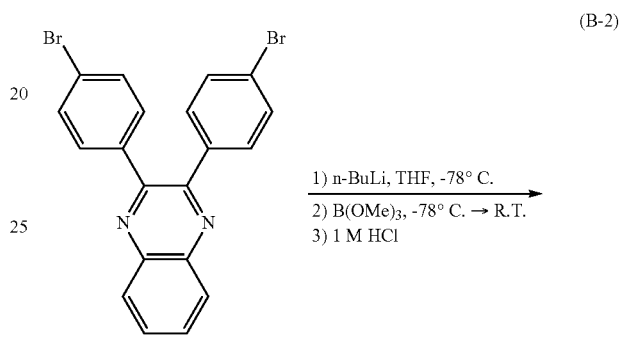

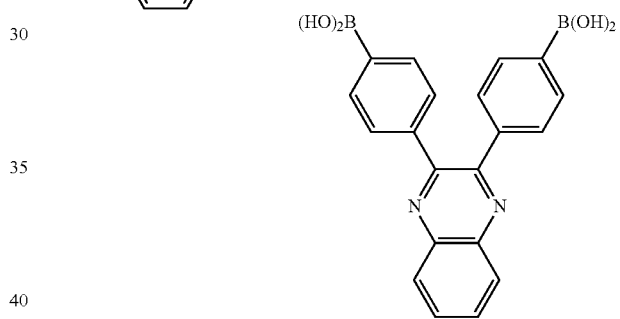

20.0 g (54.1 mmol) of 2,3-bis(4-bromophenyl)quinoxaline was put into a 500-mL three-neck flask, and nitrogen substitution was performed thereon. 150 mL of tetrahydrofuran (abbrev.: THF) was added to the flask. Then, after this solution was cooled to −78° C., 75.8 mL (119 mmol) of n-butyllithium (a 1.57 mol/L hexane solution) was dripped thereinto, and the solution was stirred at the same temperature for 2 hours. After that, 22.5 g (216 mmol) of trimethyl borate was added thereto, and the solution was stirred for 24 hours while being returned to room temperature. After the reaction, 200 mL of 1.0 mol/L hydrochloric acid was added to the reaction solution, and the solution was stirred for 1 hour at room temperature. A precipitate in the reaction mixture was recovered by suction filtration, and the resulting residue was recrystallized with a mixed solvent of chloroform and hexane, whereby 14.6 g of a white powder solid of 4,4'-(quinoxaline-2,3-diyl)diphenylboronic acid that was a subject matter was obtained at a yield of 73%.

[Step 3] Synthesis of 4-bromotriphenylamine

A synthesis method of 4-bromotriphenylamine is described. A synthesis scheme of 4-bromotriphenylamine is shown in (B-3).

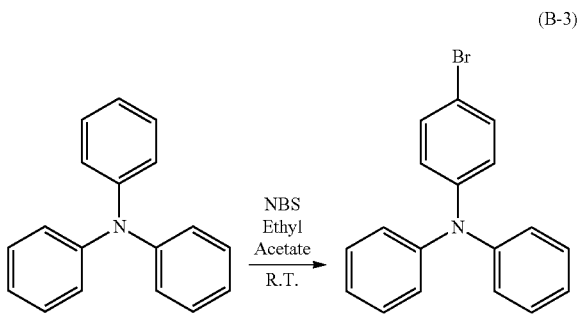 [SMILES: c1ccc(N(c2ccccc2)c2ccccc2)cc1 ; Brc1ccc(N(c2ccccc2)c2ccccc2)cc1]

(B-3)

In a 1-L Erlenmeyer flask, 25 g (100 mmol) of triphenylamine, 18 g (100 mmol) of N-bromosuccinimide, and 400 mL of ethyl acetate were put and stirred at room temperature in air for 24 hours. After the reaction, the reaction solution was washed twice with a saturated aqueous solution of sodium carbonate to separate into an aqueous layer and an organic layer. The aqueous layer was extracted twice with ethyl acetate and washed with saturated saline together with the organic layer. After the organic layer was dried with magnesium sulfate, natural filtration and enrichment was performed, and the resulting white solid was recrystallized with ethyl acetate and hexane, whereby 22 g of a white powder solid of 4-bromotriphenylamine was obtained at a yield of 66%.

[Step 4] Synthesis of TPAPQ

A synthesis method of 2,3-bis[4-(4-diphenylaminophenyl)phenyl]quinoxaline (abbrev.: TPAPQ) is described. A synthesis scheme of TPAPQ is shown in (B-4).

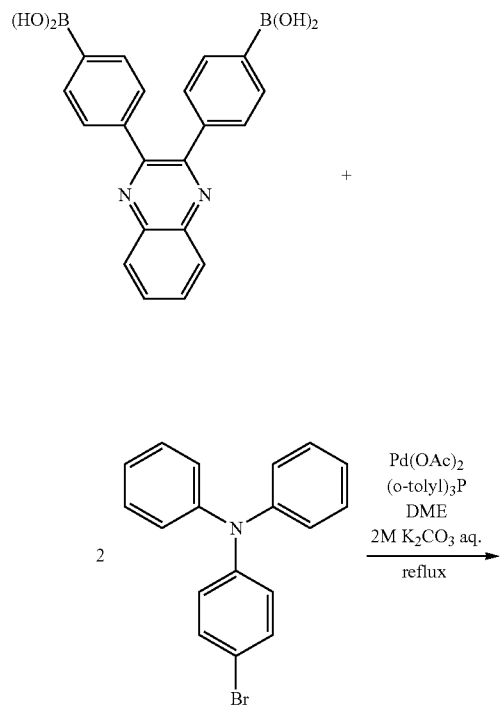

(B-4)

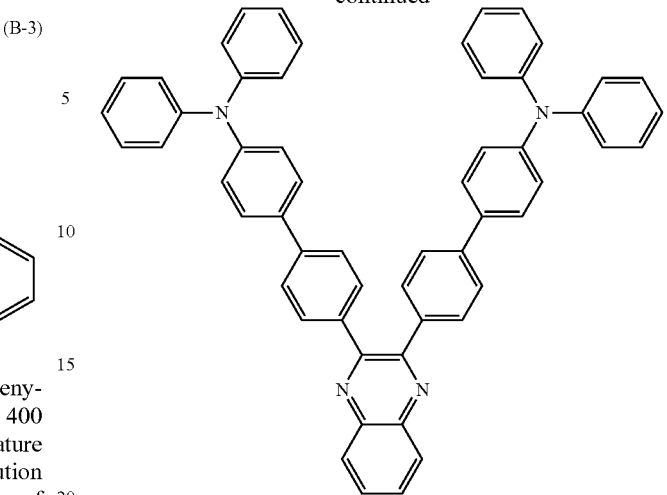

5.0 g (14 mmol) of 4,4'-(quinoxaline-2,3-diyl)diphenylboronic acid, 9.7 g (30 mmol) of 4-bromotriphenylamine, 0.067 g (0.30 mmol) of palladium (II) acetate, and 0.63 g (2.1 mmol) of tri(ortho-tolyl)phosphine were put into a 300-mL three-neck flask, and nitrogen substitution was performed thereon. 70 mL of ethylene glycol dimethyl ether (abbrev.: DME) and 45 mL (90 mmol) of a potassium carbonate solution (2.0 mol/L) were added to the mixture. A reflux of this mixture was performed for 7 hours at 80° C. After the reaction, the reaction solution was washed with water, an aqueous layer was extracted with ethyl acetate, and the extracted solution was dried with magnesium sulfate together with an organic layer. After the drying, suction filtration and enrichment of the mixture was performed. The resulting residue was refined with silica gel column chromatography (a developing solvent: toluene), and the resulting solution was enriched. The resulting solid was recrystallized with a mixed solvent of chloroform and hexane, whereby 3.6 g of a yellow powder solid that was a subject matter was obtained at a yield of 35%. By the nuclear magnetic resonance method (NMR), it was confirmed that this compound was 2,3-bis[4-(4-diphenylaminophenyl)phenyl]quinoxaline (abbrev.: TPAPQ).

On 3.58 g of the obtained 2,3-bis[4-(4-diphenylaminophenyl)phenyl]quinoxaline (abbrev.: TPAPQ), sublimation refining was performed by heating at 320° C. under the conditions in that the pressure was 7.8 Pa and the argon flow was 3.0 mL/min, whereby 3.05 g of 2,3-bis[4-(4-diphenylaminophenyl)phenyl]quinoxaline (abbrev.: TPAPQ) was recovered, and the recovery rate was 85%.

Figure 11A:
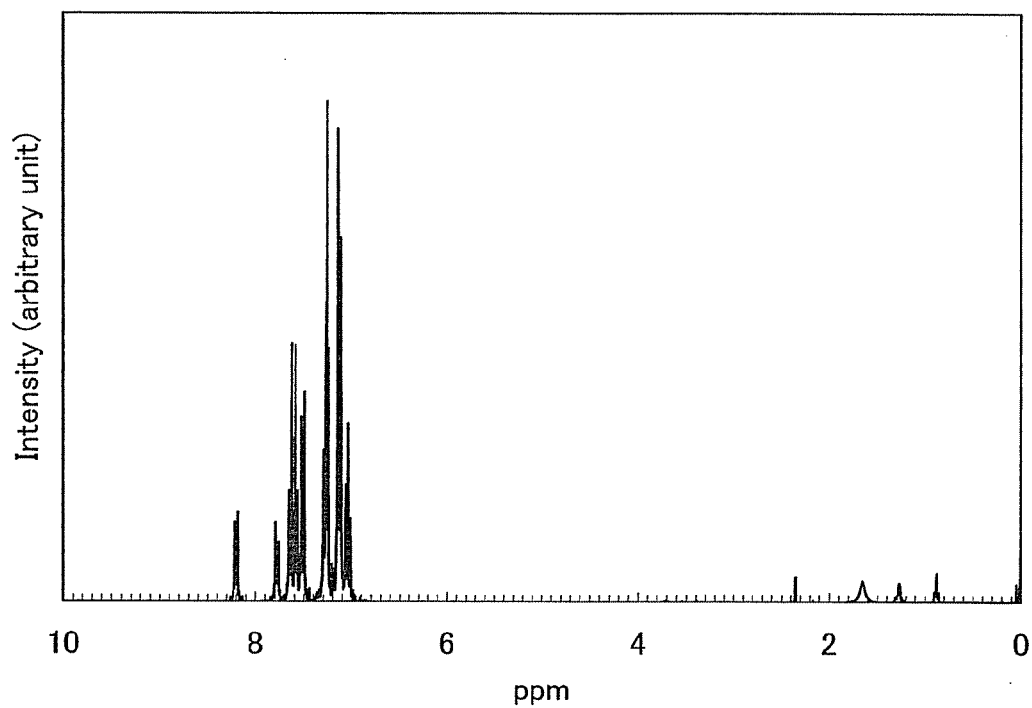
FIGS. 11A and 11B are $^1$H NMR charts of 2,3-bis[4-(4-diphenylaminophenyl)phenyl]quinoxaline (abbrev.: TPAPQ), which is a quinoxaline derivative of the present invention.
Figure 11B:
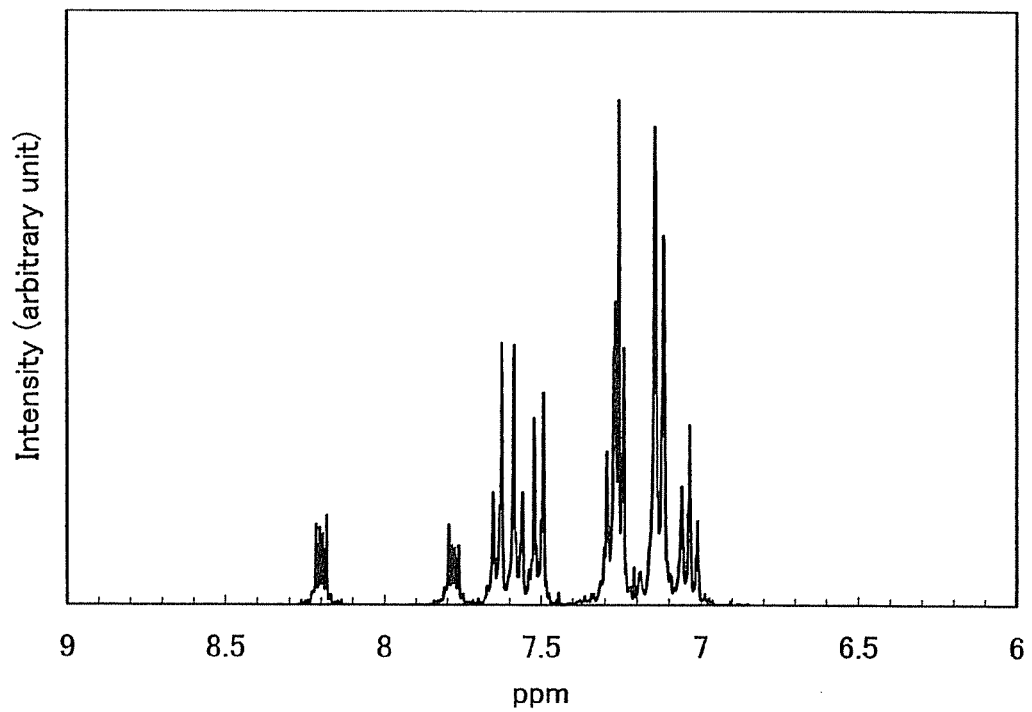

A result of proton nuclear magnetic resonance spectrometry method ($^1$H NMR) analysis of TPAPQ is as follows: $^1$H NMR (300 MHz, CDCl$_3$): δ=7.01-7.65 (m, 36H), 7.76-7.80 (m, 2H), and 8.18-8.22 (m, 2H). An $^1$H NMR chart is shown in FIGS. 11A and 11B. FIG. 11B is an enlarged chart of FIG. 11A in the range of 6.0 ppm to 9.0 ppm.

TG-DTA (Thermogravimetry-Differential Thermal Analysis) of TPAPQ was performed. For the measurement, a Thermo-Gravimetric/Differential Thermal Analyzer (TG/-DTA-320, manufactured by SII NanoTechnology Inc.) was used, and thermophysical properties were evaluated under a nitrogen atmosphere with a rising temperature of 10° C./min. Consequently, from the gravity-temperature relationship (thermogravimetric measurement), the temperature at which the gravity was 95% or less of the gravity at the starting point of the measurement was, under normal pressure, 460° C. Thus, high heat resistance was exhibited.

Figure 12:
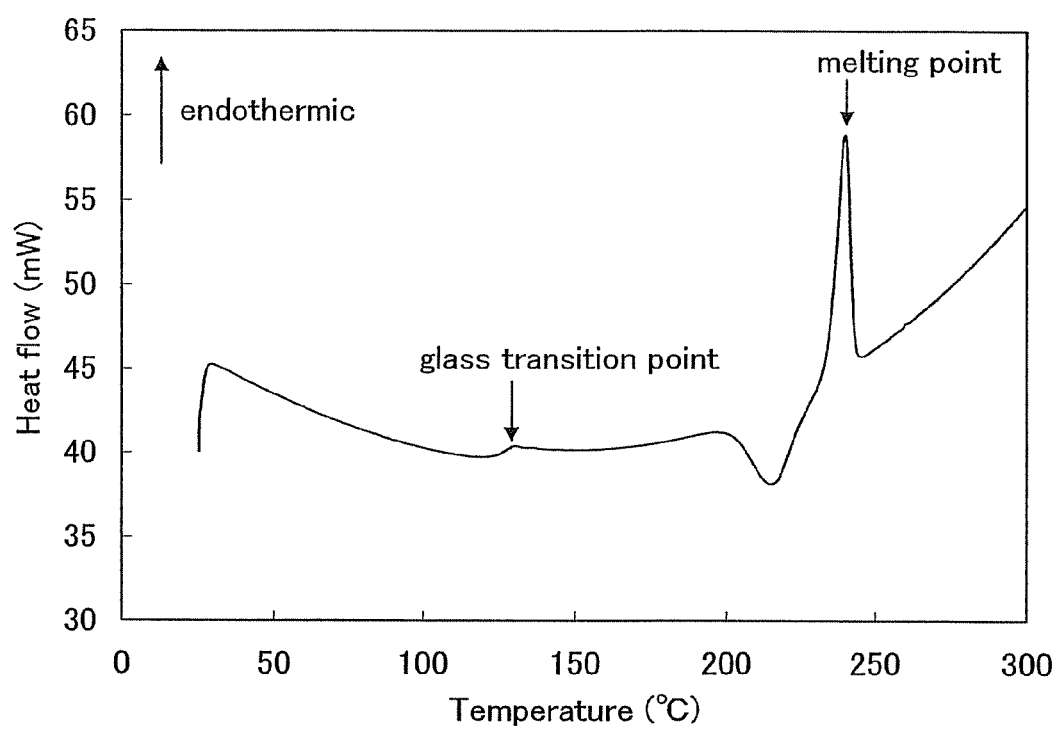
FIG. 12 is a DSC chart of 2,3-bis[4-(4-diphenylaminophenyl)phenyl]quinoxaline (abbrev.: TPAPQ), which is a quinoxaline derivative of the present invention.

Further, a glass transition point of TPAPQ was measured with a differential scanning calorimeter (DSC; Pyris 1, manufactured by Perkin Elmer Co., Ltd.). First, a sample thereof was heated to 300° C. at 40° C./min to dissolve the test sample and then cooled to room temperature at 40° C./min. After that, the temperature was increased to 300° C. at 10° C./min. In this manner, a DSC chart shown in FIG. 12 was obtained. From this chart, it was found that a glass transition point (Tg) and a melting point of TPAPQ were 121° C. and 235° C. respectively. Accordingly, it was found that TPAPQ has a high glass transition point.

Figure 13:
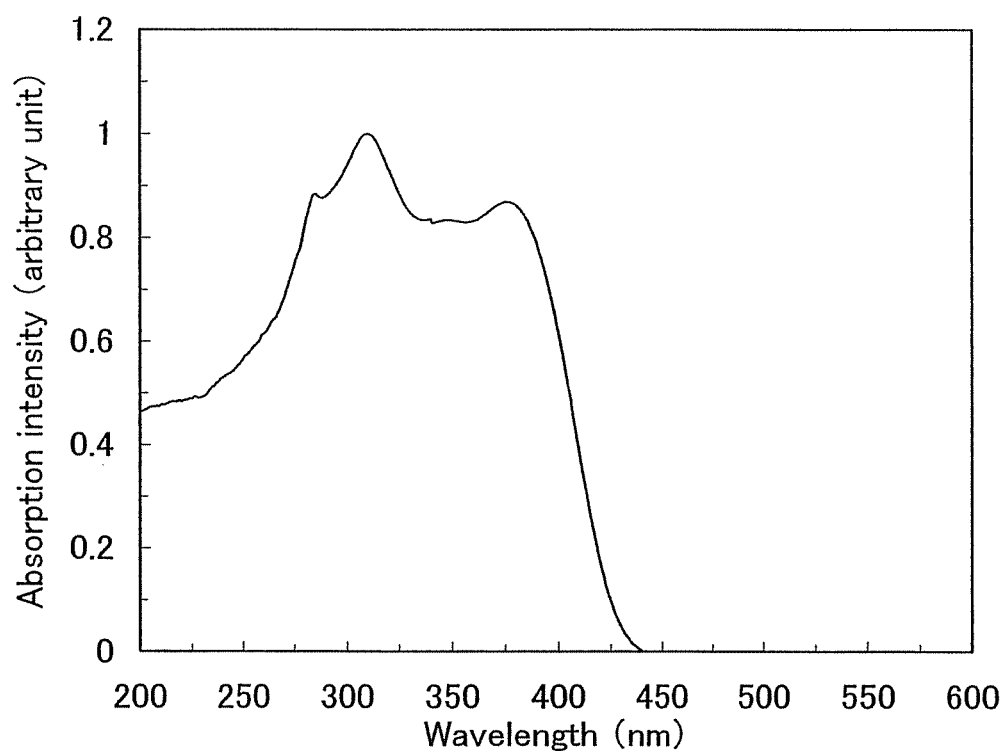
FIG. 13 is a graph showing an absorption spectrum of 2,3-bis[4-(4-diphenylaminophenyl)phenyl]quinoxaline (abbrev.: TPAPQ), which is the quinoxaline derivative of the present invention, in a toluene solution.
Figure 14:
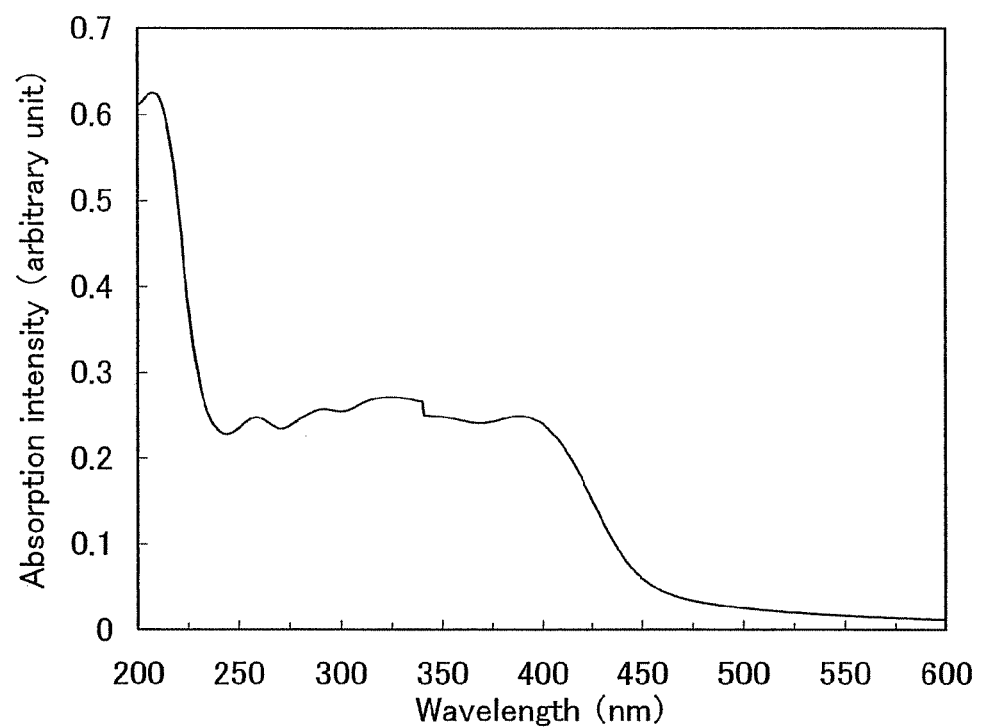
FIG. 14 is a graph showing an absorption spectrum of a thin film of 2,3-bis[4-(4-diphenylaminophenyl)phenyl]quinoxaline (abbrev.: TPAPQ), which is a quinoxaline derivative of the present invention.
Figure 15:
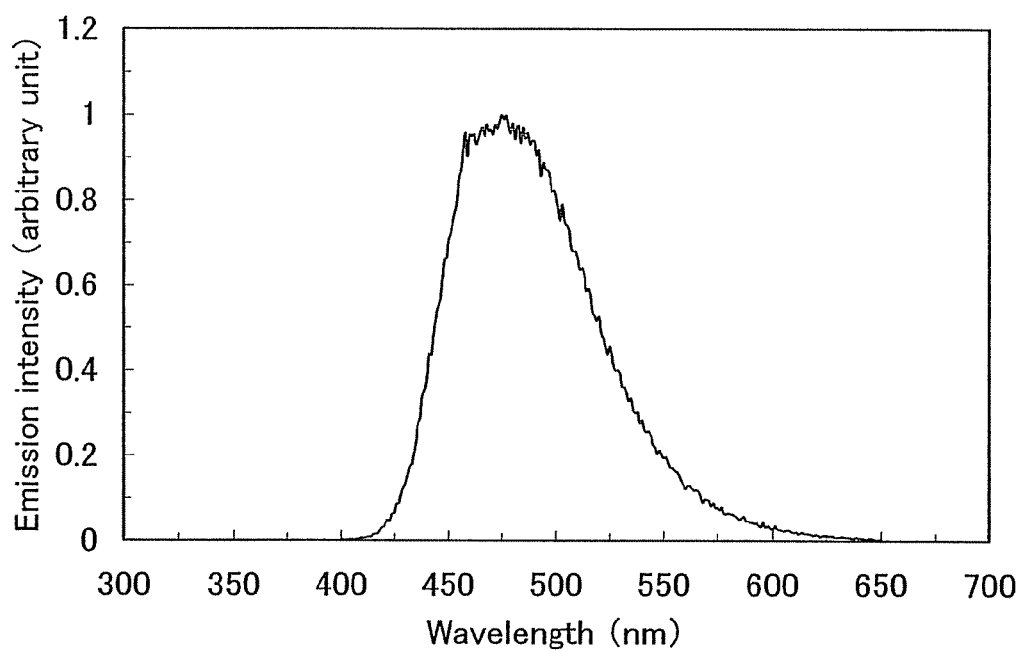
FIG. 15 is a graph showing a light emission spectrum of 2,3-bis[4-(4-diphenylaminophenyl)phenyl]quinoxaline (abbrev.: TPAPQ), which is a quinoxaline derivative of the present invention, in a toluene solution.

Further, an absorption spectrum of toluene solution of TPAPQ is shown in FIG. 13. Further, an absorption spectrum of thin film of TPAPQ is shown in FIG. 14. An ultraviolet-visible spectrophotometer (type V550, manufactured by Japan Spectroscopy Corporation) was used for the measurement. For making each sample, the solution was contained in a quartz cell, and the thin film was deposited over a quartz substrate. Each absorption spectrum of the solution and the thin film shown in FIGS. 13 and 14 was obtained by subtracting the spectrum of the quartz. In FIGS. 13 and 14, a horizontal axis indicates wavelength (nm) and a vertical axis indicates absorption intensity (unit is arbitrary). For the toluene solution, absorption was observed at around 376 nm, and for the thin film, absorption was observed at around 388 nm. Further, an emission spectrum of the toluene solution of TPAPQ (excitation wavelength: 375 nm) is shown in FIG. 15. In FIG. 15, a horizontal axis indicates wavelength (nm) and a vertical axis indicates emission intensity (unit is arbitrary). For the toluene solution, the maximum emission wavelength was 475 nm (excitation wavelength: 375 nm).

Further, an ionization potential of TPAPQ in the state of thin film, which was measured with a photoelectron spectroscopy device (AC-2, manufactured by Riken Keiki Co., Ltd.) in the atmosphere, was 5.44 eV. Accordingly, it was found that the HOMO level thereof was −5.44 eV. Further, using data from FIG. 14 on the absorption spectrum of thin film of TPAPQ, an absorption edge was found from a Tauc plot for direct transition assumed, and the absorption edge was estimated as an optical energy gap; the energy gap was 2.83 eV. The LUMO level which was found from the resulting energy gap value and the HOMO level was −2.61 eV.

Further, the electrochemical stability of TPAPQ was evaluated by cyclic voltammetry (CV). An electrochemical analyzer (ALS model 600A, manufactured by BAS, Inc.) was used as the measuring device. The solution for the CV measurement was prepared by using dehydrated dimethylformamide (DMF) as a solvent, dissolving tetra-n-butylammonium perchlorate (n-Bu$_4$NClO$_4$), which is a supporting electrolyte, to a concentration of 100 mM and dissolving TPAPQ, which is an object of the measurement, to a concentration of 1 mM. Further, a platinum electrode (PTE platinum electrode, manufactured by BAS, Inc.) was used as a working electrode, another platinum electrode (Pt counter electrode (5 cm) for VC-3, manufactured by BAS, Inc.) was used as an auxiliary electrode, and an Ag/Ag$^+$ electrode (RE5 non-aqueous solvent reference electrode, manufactured by BAS, Inc.) was used as a reference electrode. The scanning speed was set at 0.1 V/sec, and a 100-cycle CV measurement was conducted for each of an oxidation case and a reduction case.

Figure 16A:
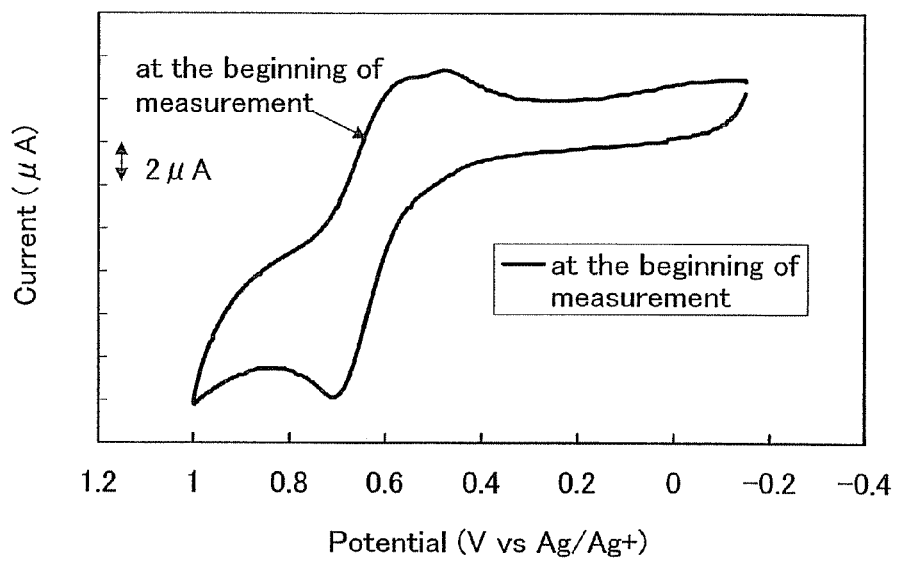
FIGS. 16A and 16B are graphs showing results of CV measurement, in the case of oxidation, of 2,3-bis[4-(4-diphenylaminophenyl)phenyl]quinoxaline (abbrev.: TPAPQ), which is a quinoxaline derivative of the present invention.
Figure 16B:
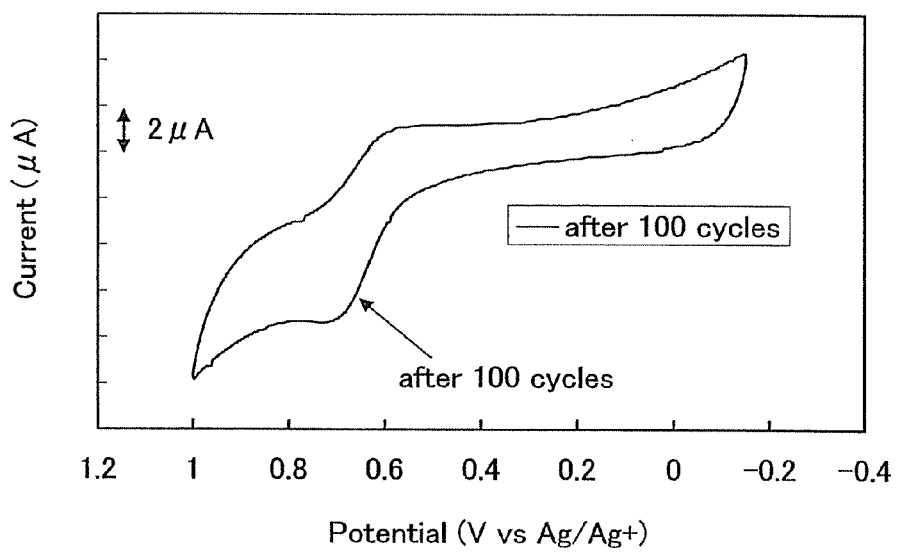
Figure 17A:
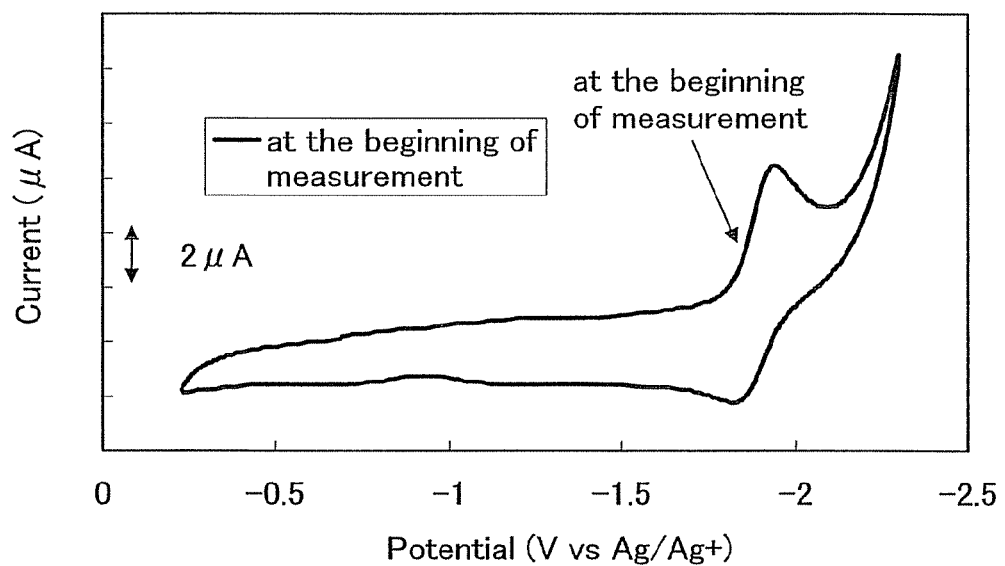
FIGS. 17A and 17B are graphs showing results of CV measurement, in the case of reduction, of 2,3-bis[4-(4-diphenylaminophenyl)phenyl]quinoxaline (abbrev.: TPAPQ), which is a quinoxaline derivative of the present invention.
Figure 17B:
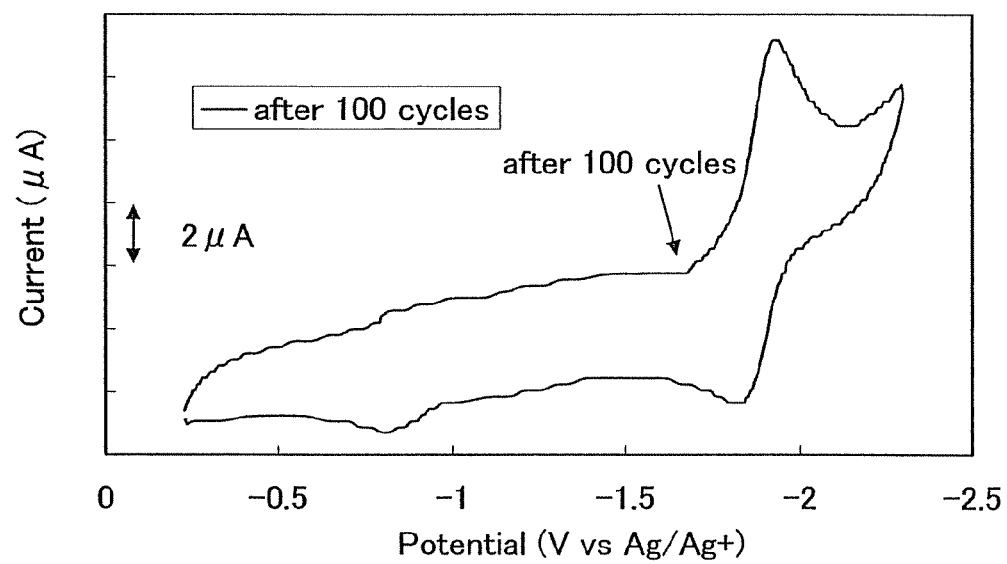

FIGS. 16A and 16B show the results of CV measurement in the oxidation case of TPAPQ, and FIGS. 17A and 17B show the results of CV measurement in the reduction case of TPAPQ. FIG. 16A shows the measurement result at the beginning of the measurement, whereas FIG. 16B shows the measurement result after 100 cycles. Similarly, FIG. 17A shows the measurement result at the beginning of the measurement, whereas FIG. 17B shows the measurement result after 100 cycles. It was found that a reversible peak is obtained in either of the oxidation case and the reduction case. In addition, even if oxidation or reduction is repeated 100 times, each peak position hardly changes. This means that TPAPQ is stable with respect to oxidation and reduction, that is, it is electrochemically stable.

(Embodiment 2)

In this embodiment, an example of a synthetic example of 2,3-bis[4-(9-phenylcarbazol-3-yl)phenyl]quinoxaline (abbrev.: PCPQ) which is the quinoxaline derivative of the present invention represented by the structural formula (12) is described.

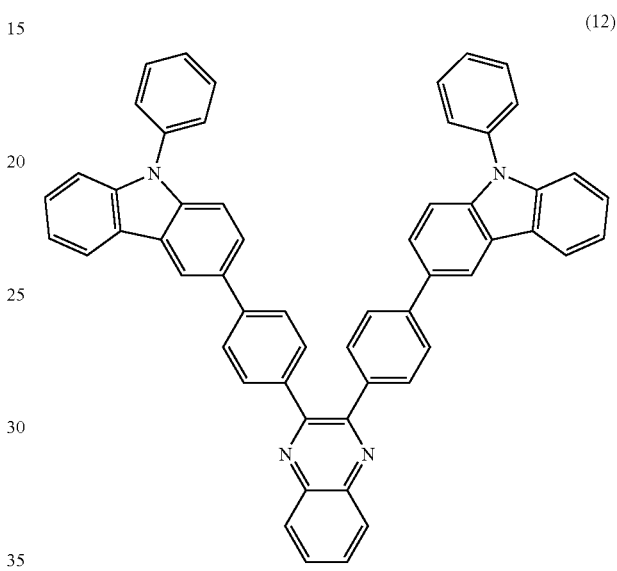

(12)

[Step 1] Synthesis of 3-bromo-9-phenylcarbazole

A synthesis method of 3-bromo-9-phenylcarbazole is described. A synthesis scheme of 3-bromo-9-phenylcarbazole is shown in (C-1).

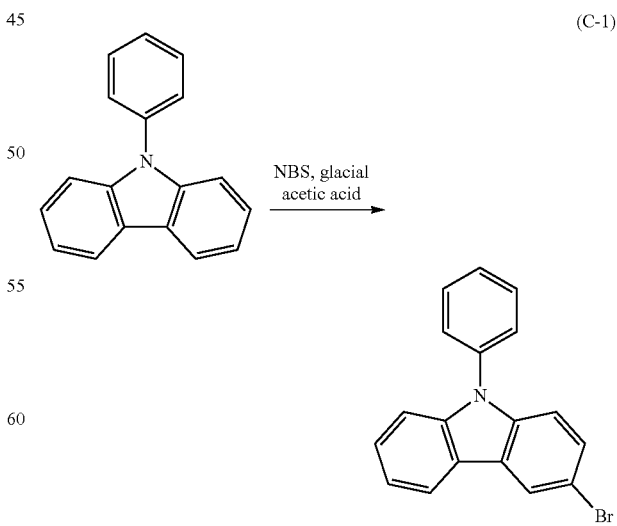

(C-1)

24.3 g (100 mmol) of 9-phenylcarbazole was put into a 2-L Erlenmeyer flask and dissolved by addition of 600 mL of glacial acetic acid. 17.8 g (100 mmol) of N-bromosuccinimide was slowly added into this solution and stirred for about 12 hours at room temperature. By dripping this reaction solution into 1 L of ice water while being stirred, a white solid was separated out. This separated white solid was recovered by suction filtration and washed three times with water. This solid was dissolved in 150 mL of diethyl ether and washed with a saturated sodium acid carbonate solution and water. This organic layer was dried with magnesium sulfate. Suction filtration of the mixture was performed, and the resulting filtrate was enriched. Recrystallization thereof was performed by addition of about 50 mL of methanol into this enriched solution and being left standing, whereby 28.4 g of a white powder solid of 3-bromo-9-phenylcarbazole was obtained at a yield of 88%.

[Step 2] Synthesis of PCPQ

A synthesis method of 2,3-bis[4-(9-phenylcarbazol-3-yl)phenyl]quinoxaline (abbrev.: PCPQ) is described. A synthesis scheme of PCPQ is shown in (C-2).

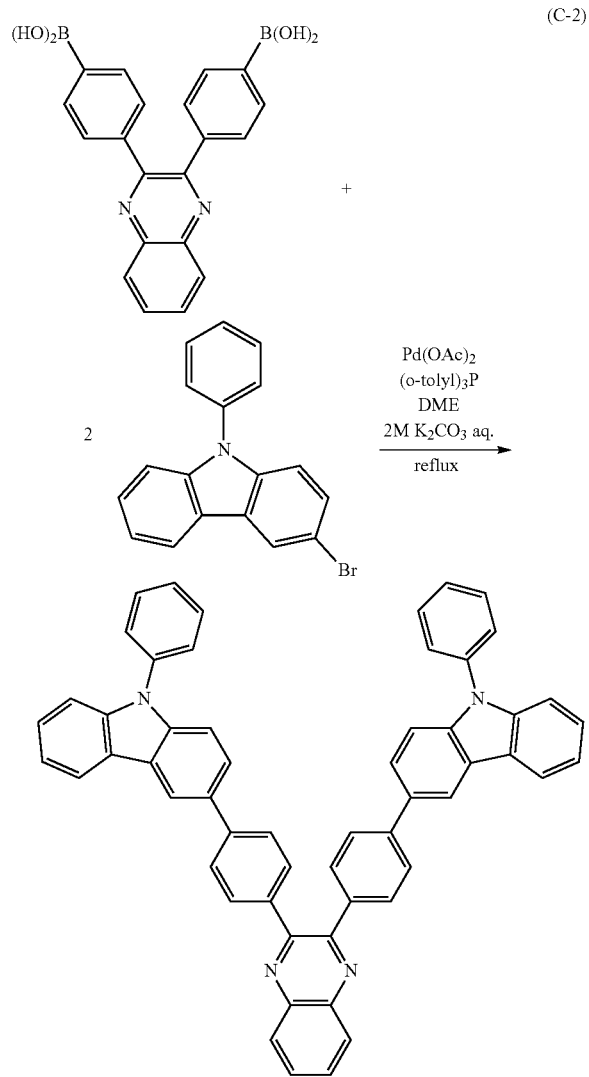

1.5 g (4.0 mmol) of the obtained 4,4'-(quinoxaline-2,3-diyl)diphenylboronic acid synthesized in Embodiment 1, 2.9 g (8.9 mmol) of 3-bromo-9-phenylcarbazole, 0.020 g (0.089 mmol) of palladium (II) acetate, and 0.19 g (0.61 mmol) of tri(ortho-tolyl)phosphine were put into a 100-mL three-neck flask, and nitrogen substitution was performed thereon. 20 mL of ethylene glycol dimethyl ether (abbrev.: DME) and 13 mL (27 mmol) of a potassium carbonate solution (2.0 mol/L) were added to the mixture. A reflux of this mixture was performed for 13 hours at 80° C. After the reaction, the reaction mixture was washed with water, and an aqueous layer was extracted with ethyl acetate and dried with magnesium sulfate together with an organic layer. After the drying, suction filtration and enrichment of the mixture was performed. The resulting residue was dissolved in toluene, and the resulting solution was subjected to suction filtration with florisil, celite, and alumina. The filtrate was enriched, and the resulting solid was recrystallized with a mixed solvent of ethyl acetate and methanol, whereby 2.2 g of a yellow powder solid that was a subject matter was obtained at a yield of 73%. By the nuclear magnetic resonance method (NMR), it was confirmed that this compound was 2,3-bis[4-(9-phenylcarbazol-3-yl)phenyl]quinoxaline (abbrev.: PCPQ).

On 2.2 g of the obtained 2,3-bis[4-(9-phenylcarbazol-3-yl)phenyl]quinoxaline (abbrev.: PCPQ), sublimation refining was performed by heating at 360° C. under the conditions in that the pressure was 7.8 Pa and the argon flow was 3.0 mL/min, whereby 0.93 g of 2,3-bis[4-(9-phenylcarbazol-3-yl)phenyl]quinoxaline (abbrev.: PCPQ) was recovered, and the recovery rate was 43%.

Figure 18A:
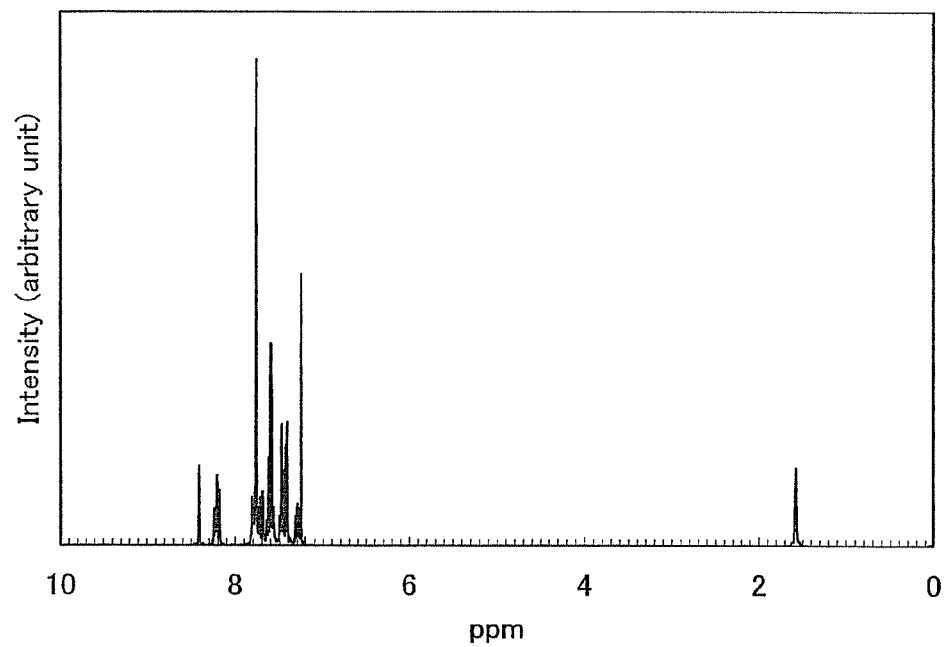
FIGS. 18A and 18B are $^1$H NMR charts of 2,3-bis[4-(9-phenylcarbazol-3-yl)phenyl]quinoxaline (abbrev.: PCPQ), which is a quinoxaline derivative of the present invention.
Figure 18B:
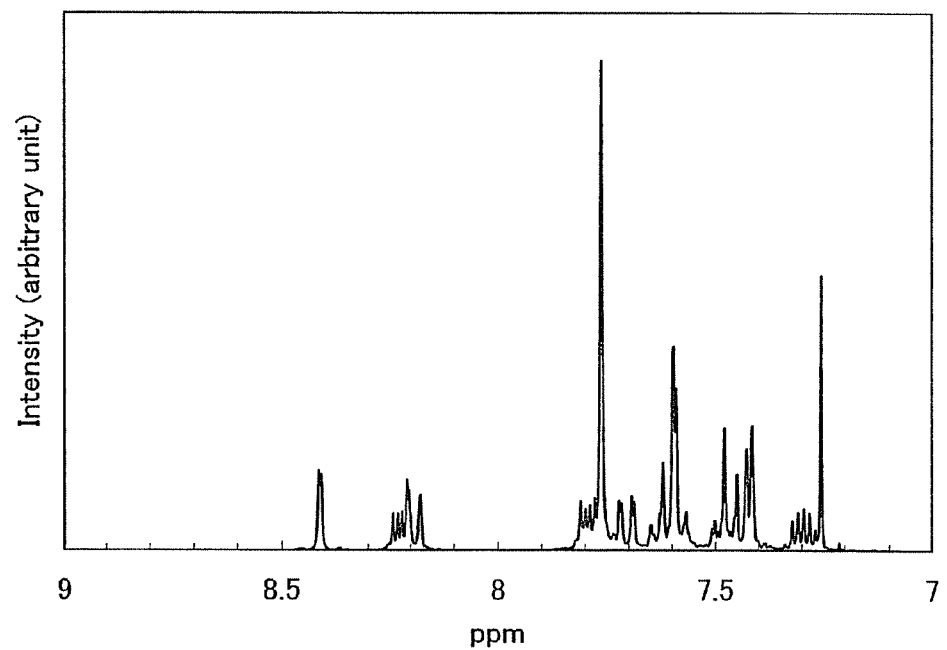

A result of proton nuclear magnetic resonance spectrometry method ($^1$H NMR) analysis of PCPQ is as follows: $^1$H NMR (300 MHz, CDCl$_3$): δ=7.28-7.32 (m, 2H), 7.41-7.48 (m, 8H), 7.57-7.63 (m, 8H), 7.69-7.81 (m, 12H), 8.18-8.24 (m, 4H), and 8.41-8.42 (m, 2H). An $^1$H NMR chart is shown in FIGS. 18A and 18B. FIG. 18B is an enlarged chart of FIG. 18A in the range of 7.0 ppm to 9.0 ppm.

TG-DTA (Thermogravimetry-Differential Thermal Analysis) of PCPQ was performed. For the measurement, a Thermo-Gravimetric/Differential Thermal Analyzer (TG/-DTA-320, manufactured by SII NanoTechnology Inc.) was used, and thermophysical properties were evaluated under a nitrogen atmosphere with a rising temperature of 10° C./min. Consequently, from the gravity-temperature relationship (thermogravimetric measurement), the temperature at which the gravity was 95% or less of the gravity at the starting point of the measurement was, under normal pressure, 425° C. Thus, high heat resistance was exhibited.

Figure 19:
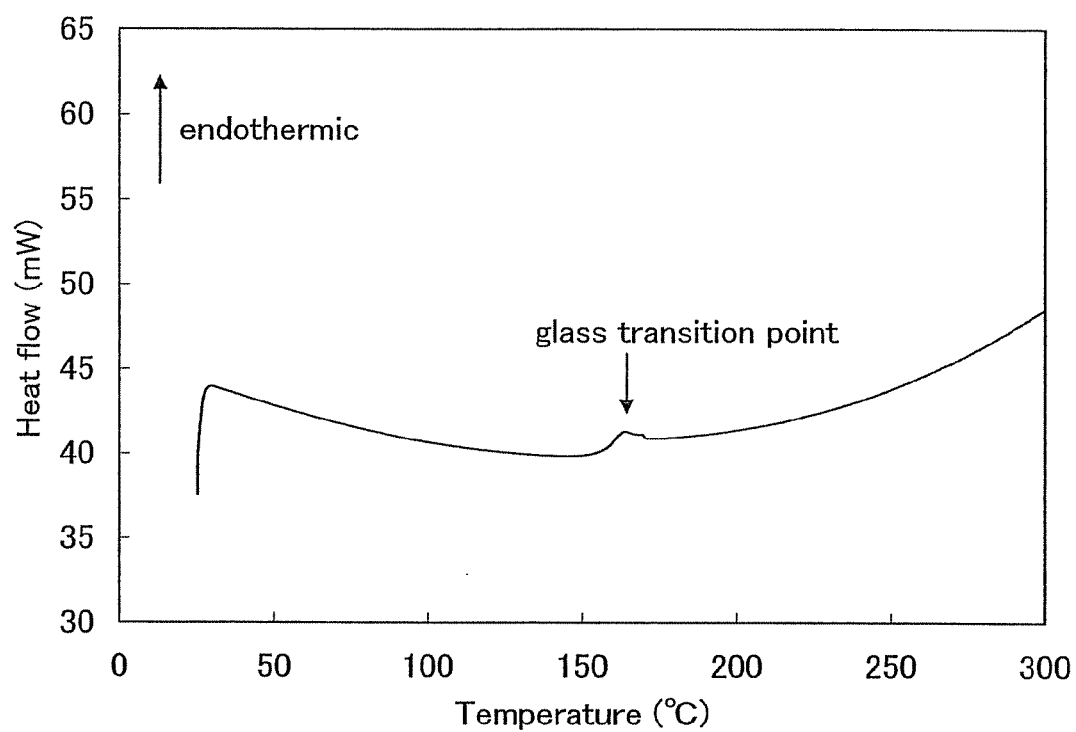
FIG. 19 is a DSC chart of 2,3-bis[4-(9-phenylcarbazol-3-yl)phenyl]quinoxaline (abbrev.: PCPQ), which is a quinoxaline derivative of the present invention.

Further, a glass transition point of PCPQ was measured with a differential scanning calorimeter (DSC; Pyris 1, manufactured by Perkin Elmer Co., Ltd.). First, a sample thereof was heated to 380° C. at 40° C./min and then cooled to room temperature at 40° C./min. After that, the temperature was increased to 380° C. at 10° C./min. In this manner, a DSC chart shown in FIG. 19 was obtained. From this chart, it was found that the glass transition point (Tg) was 154° C. Accordingly, it was found that PCPQ has a high glass transition point. Note that because of a high amorphous nature of PCPQ, a peak indicating a melting point was not observed.

Figure 20:
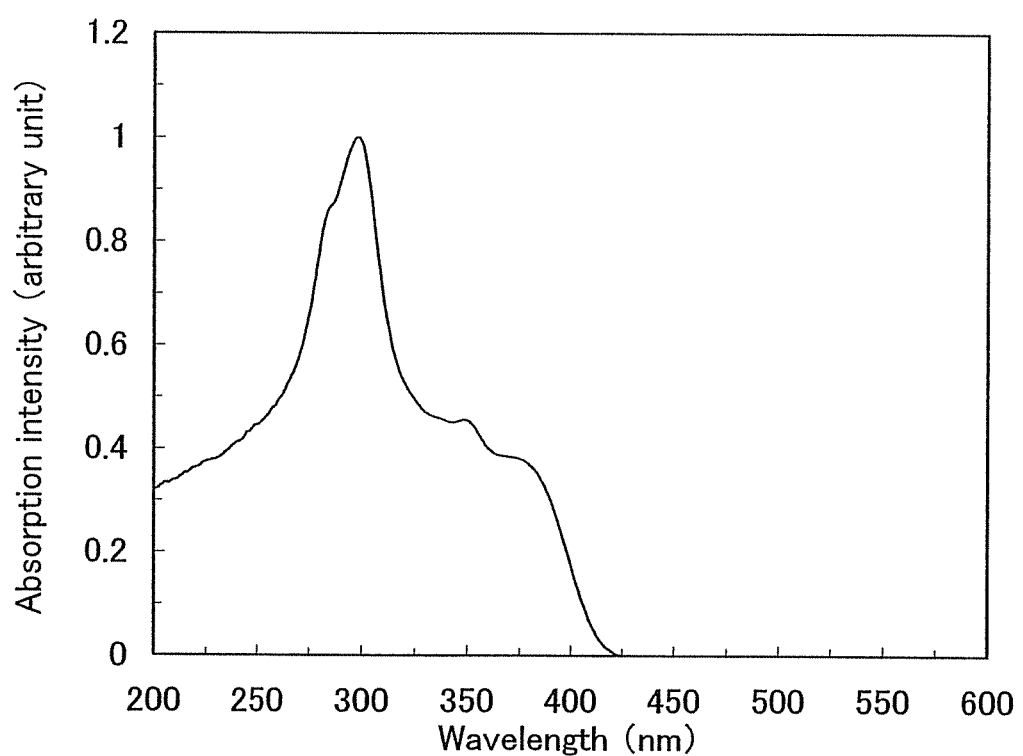
FIG. 20 is a graph showing an absorption spectrum of 2,3-bis[4-(9-phenylcarbazol-3-yl)phenyl]quinoxaline (abbrev.: PCPQ), which is a quinoxaline derivative of the present invention, in a toluene solution.
Figure 21:
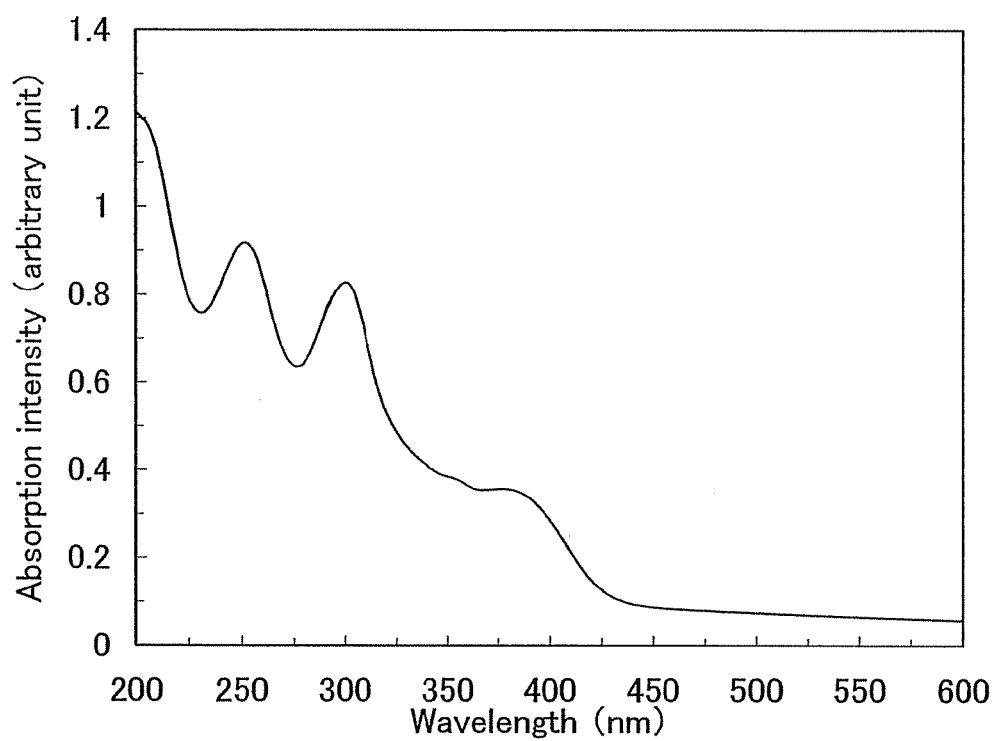
FIG. 21 is a graph showing an absorption spectrum of a thin film of 2,3-bis[4-(9-phenylcarbazol-3-yl)phenyl]quinoxaline (abbrev.: PCPQ), which is a quinoxaline derivative of the present invention.
Figure 22:
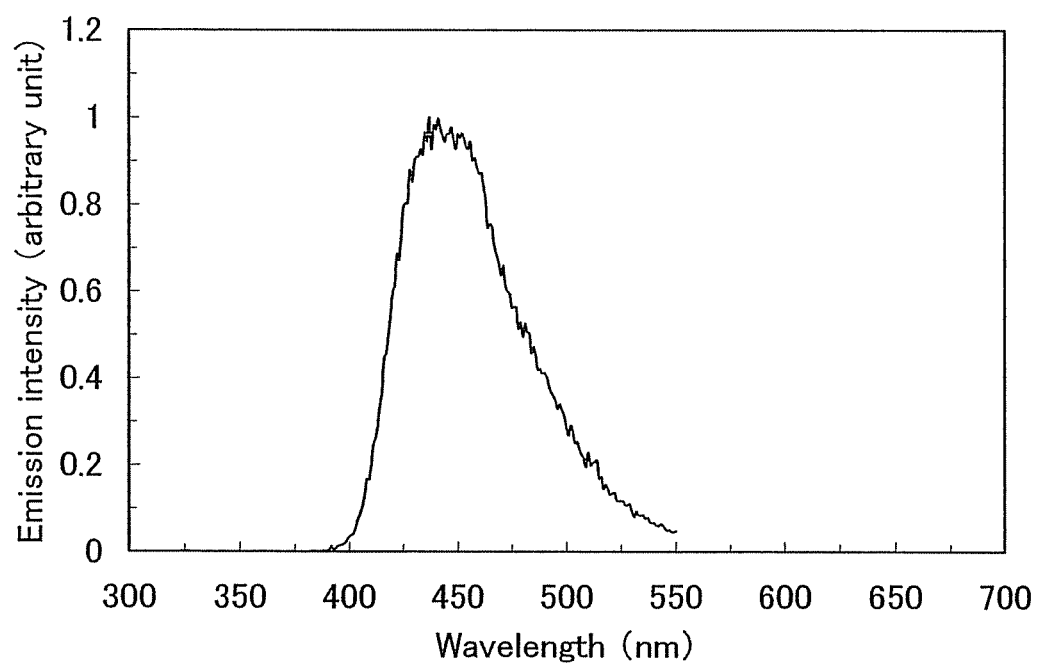
FIG. 22 is a graph showing a light emission spectrum of 2,3-bis[4-(9-phenylcarbazol-3-yl)phenyl]quinoxaline (abbrev.: PCPQ), which is a quinoxaline derivative of the present invention, in a toluene solution.
Figure 23:
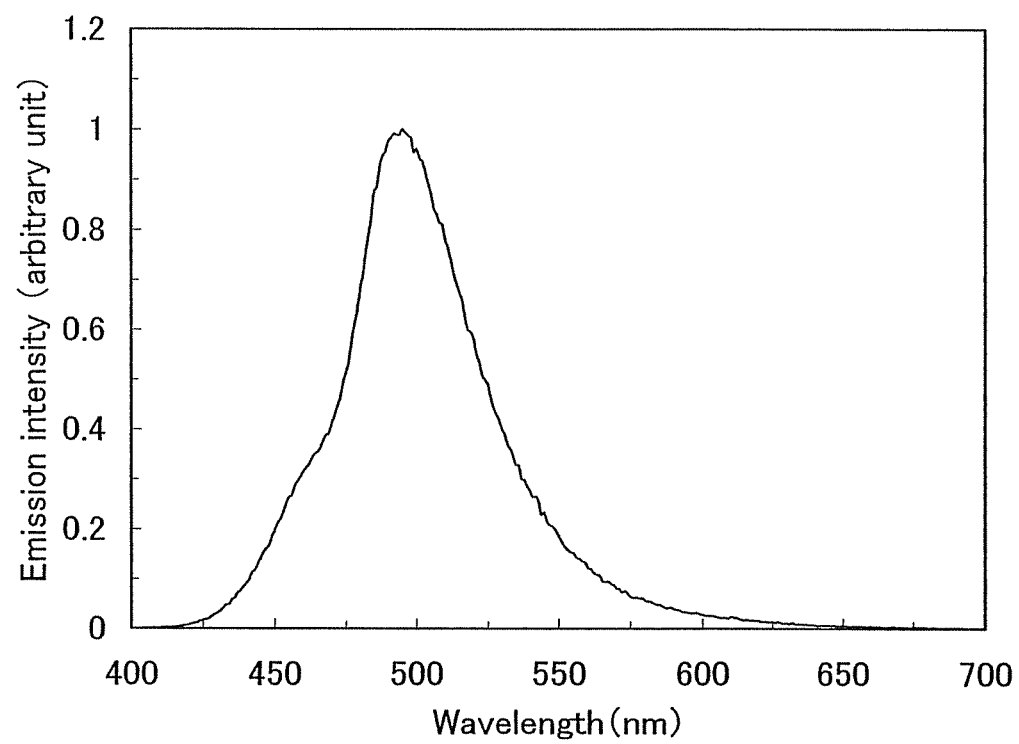
FIG. 23 is a graph showing a light emission spectrum of a thin film of 2,3-bis[4-(9-phenylcarbazol-3-yl)phenyl]quinoxaline (abbrev.: PCPQ), which is a quinoxaline derivative of the present invention.

Further, an absorption spectrum of toluene solution of PCPQ is shown in FIG. 20. Further, an absorption spectrum of thin film of PCPQ is shown in FIG. 21. An ultraviolet-visible spectrophotometer (type V550, manufactured by Japan Spectroscopy Corporation) was used for the measurement. For making each sample, the solution was contained in a quartz cell, and the thin film was deposited over a quartz substrate. Each absorption spectrum of the solution and the thin film shown in FIGS. 20 and 21 was obtained by subtracting the spectrum of the quartz. In FIGS. 20 and 21, a horizontal axis indicates wavelength (nm) and a vertical axis indicates absorption intensity (unit is arbitrary). For the toluene solution, absorption was observed at around 349 nm, and for the thin film, absorption was observed at around 377 nm. Further, an emission spectrum of the toluene solution of PCPQ (excitation wavelength: 298 nm) is shown in FIG. 22. Further, an emission spectrum of the thin film of PCPQ (excitation wavelength: 400 nm) is shown in FIG. 23. In FIGS. 22 and 23, a horizontal axis indicates wavelength (nm) and a vertical axis indicates emission intensity (unit is arbitrary). The maximum emission wavelength was 441 nm (excitation wavelength: 298 nm) for the toluene solution, and was 495 nm (excitation wavelength: 400 nm) for the thin film.

Further, an ionization potential of PCPQ in the state of thin film, which was measured with a photoelectron spectroscopy device (AC-2, manufactured by Riken Keiki Co., Ltd.) in the atmosphere, was 5.57 eV. Accordingly, it was found that the HOMO level thereof was −5.57 eV. Further, using data on the absorption spectrum of thin film of PCPQ, an absorption edge was found from a Tauc plot for direct transition assumed, and the absorption edge was estimated as an optical energy gap; the energy gap was 2.94 eV. The LUMO level which was found from the resulting energy gap value and the HOMO level was −2.63 eV.

Further, the electrochemical stability of PCPQ was evaluated by cyclic voltammetry (CV). An electrochemical analyzer (ALS model 600A, manufactured by BAS, Inc.) was used as the measuring device. The solution for the CV measurement was prepared by using dehydrated dimethylformamide (DMF) as a solvent, dissolving tetra-n-butylammonium perchlorate (n-Bu$_4$NClO$_4$), which is a supporting electrolyte, to a concentration of 100 mM and dissolving PCPQ, which is an object of the measurement, to a concentration of 1 mM. Further, a platinum electrode (PTE platinum electrode, manufactured by BAS, Inc.) was used as a working electrode, another platinum electrode (Pt counter electrode (5 cm) for VC-3, manufactured by BAS, Inc.) was used as an auxiliary electrode, and an Ag/Ag$^+$ electrode (RE5 non-aqueous solvent reference electrode, manufactured by BAS, Inc.) was used as a reference electrode. The scanning speed was set at 0.1 V/sec, and a 100-cycle CV measurement was conducted for each of an oxidation case and a reduction case.

Figure 24A:
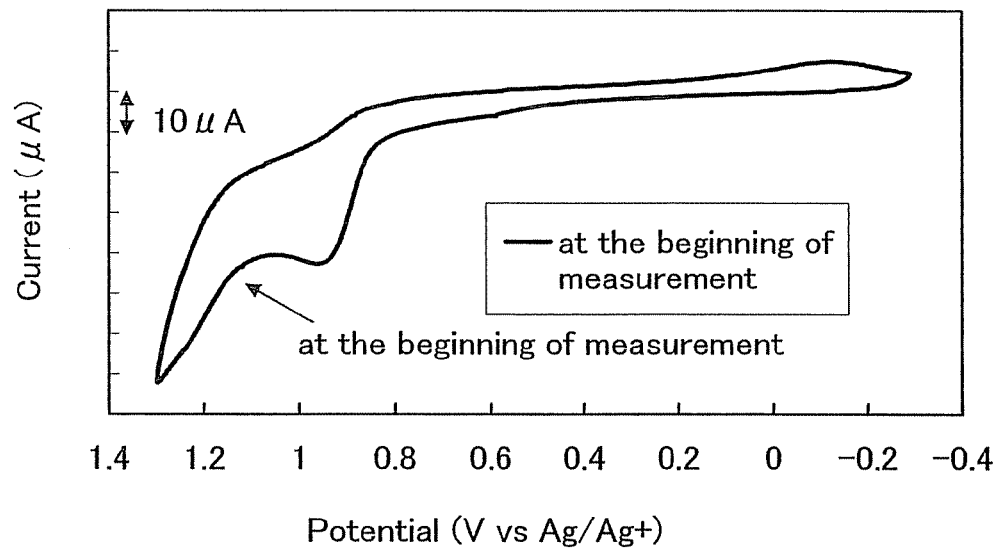
FIGS. 24A and 24B are graphs showing results of CV measurement, in the case of oxidation, of 2,3-bis[4-(9-phenylcarbazol-3-yl)phenyl]quinoxaline (abbrev.: PCPQ), which is a quinoxaline derivative of the present invention.
Figure 24B:
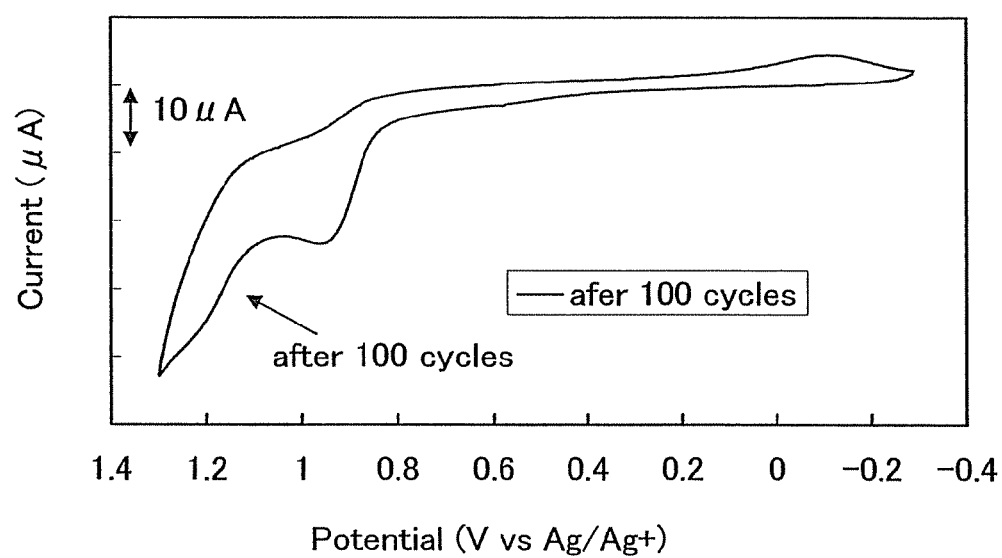
Figure 25A:
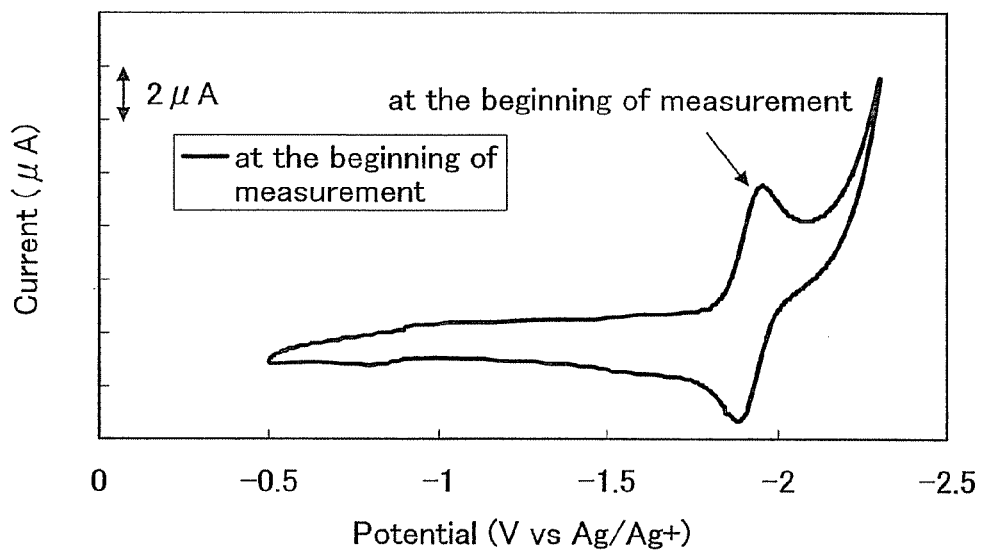
FIGS. 25A and 25B are graphs showing results of CV measurement, in the case of reduction, of 2,3-bis[4-(9-phenylcarbazol-3-yl)phenyl]quinoxaline (abbrev.: PCPQ), which is a quinoxaline derivative of the present invention.
Figure 25B:
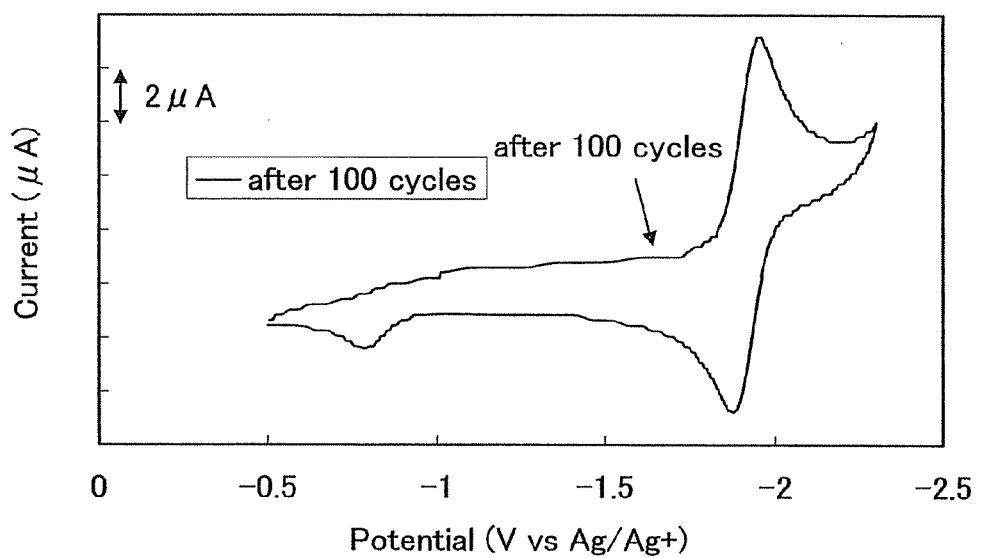

FIGS. 24A and 24B show the results of CV measurement in the oxidation case of PCPQ, and FIGS. 25A and 25B show the results of CV measurement in the reduction case of PCPQ. FIG. 24A shows the measurement result at the beginning of the measurement, whereas FIG. 24B shows the measurement result after 100 cycles. Similarly, FIG. 25A shows the measurement result at the beginning of the measurement, whereas FIG. 25B shows the measurement result after 100 cycles. It was found that a reversible peak is obtained in either of the oxidation case and the reduction case. In addition, even if oxidation or reduction is repeated 100 times, each peak position hardly changes. This means that PCPQ is stable with respect to oxidation and reduction, that is, it is electrochemically stable.

(Embodiment 3)

Figure 26:
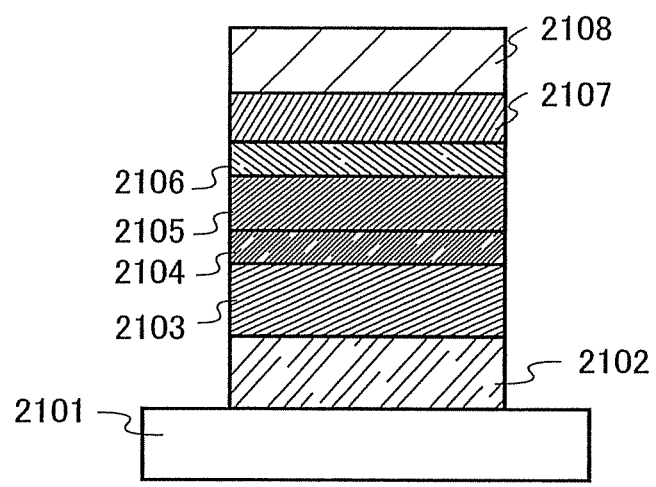
FIG. 26 is a diagram showing a light emitting element of an embodiment.

In this embodiment, the light emitting element of the present invention is described with reference to FIG. 26. The chemical formula of a material used in this embodiment is shown below.

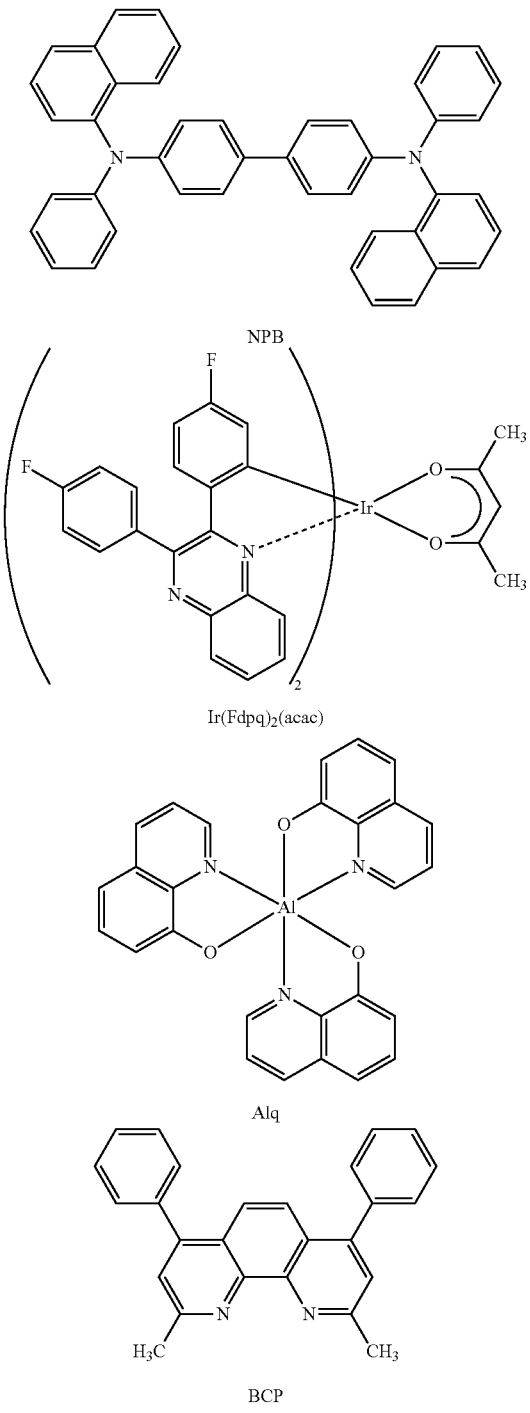

A method for manufacturing a light emitting element of this embodiment is described below.

(Light Emitting Element 1)

First, indium tin oxide containing silicon oxide (ITSO) was formed over a glass substrate 2101 by sputtering to form a first electrode 2102. A thickness thereof was set to 110 nm and an electrode area was set to 2 mm×2 mm.

Next, the substrate provided with the first electrode was fixed to a substrate holder provided in a vacuum evaporation system such that a surface provided with the first electrode was placed downward. Then, after the pressure was reduced to approximately 10$^{-4}$ Pa, 4,4'-bis[N-(1-napthyl)-N-phenylamino]biphenyl (abbrev.: NPB) and molybdenum (VI) oxide were co-evaporated, whereby a layer 2103 containing a composite material of an organic compound and an inorganic compound was formed. A thickness thereof was set to 50 nm and a weight ratio of NPB and molybdenum (VI) oxide was adjusted so as to be 4:1 (=NPB:molybdenum oxide). The co-evaporation method means an evaporation method by which evaporation is concurrently conducted from a plurality of evaporation sources in one treatment chamber.

Next, 4,4'-bis[N-(1-napthyl)-N-phenylamino]biphenyl (abbrev.: NPB) was deposited to have a film thickness of 10 nm by an evaporation method using resistance heating over the layer 2103 containing a composite material, whereby a hole transporting layer 2104 was formed.

Further, a light emitting layer 2105 having a thickness of 30 nm was formed over the hole transporting layer 2104 by co-evaporation of 2,3-bis[4-(4-diphenylaminophenyl)phenyl]quinoxaline (abbrev.: TPAPQ), which is the quinoxaline derivative of the present invention represented by the structural formula (11), and (acetylacetonato)bis[2,3-bis(4-fluorophenyl)quinoxalinato]iridium (III) (abbrev.: Ir(Fdpq)$_2$(acac)). Here, a weight ratio of TPAPQ and Ir(Fdpq)$_2$(acac) was adjusted so as to be 1:0.1 (=TPAPQ:Ir(Fdpq)$_2$(acac)).

After that, tris(8-quinolinolato)aluminum (abbrev.: Alq) was deposited to have a film thickness of 10 nm over the light emitting layer 2105 by an evaporation method using resistance heating, whereby an electron transporting layer 2106 was formed.

Further, an electron injecting layer 2107 having a thickness of 50 nm was formed over the electron transporting layer 2106 by co-evaporation of tris(8-quinolinolato)aluminum (abbrev.: Alq) and lithium. Here, a weight ratio of Alq and lithium was adjusted so as to be 1:0.01 (=Alq: lithium).

Lastly, aluminum was deposited to have a film thickness of 200 nm over the electron injecting layer 2107 by an evaporation method using resistance heating, whereby a second electrode 2108 was formed. Accordingly, Light Emitting Element 1 was manufactured.

(Comparative Light Emitting Element 1)

Comparative Light Emitting Element 1 was manufactured similarly to Light Emitting Element 1 except for a light emitting layer, and the light emitting layer was formed by co-evaporation of NPB and Ir(Fdpq)$_2$(acac). Here, a weight ratio of NPB and Ir(Fdpq)$_2$(acac) was adjusted so as to be 1:0.1 (=NPB:Ir(Fdpq)$_2$(acac)).

Figure 27:
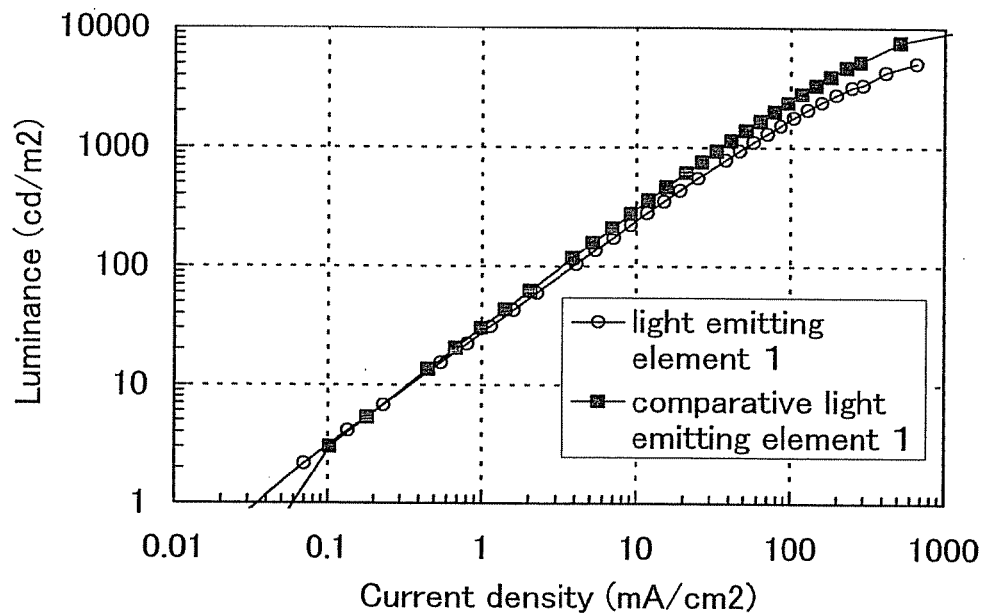
FIG. 27 is a graph showing current density versus luminance characteristics of a light emitting element manufactured in Embodiment 3.
Figure 28:
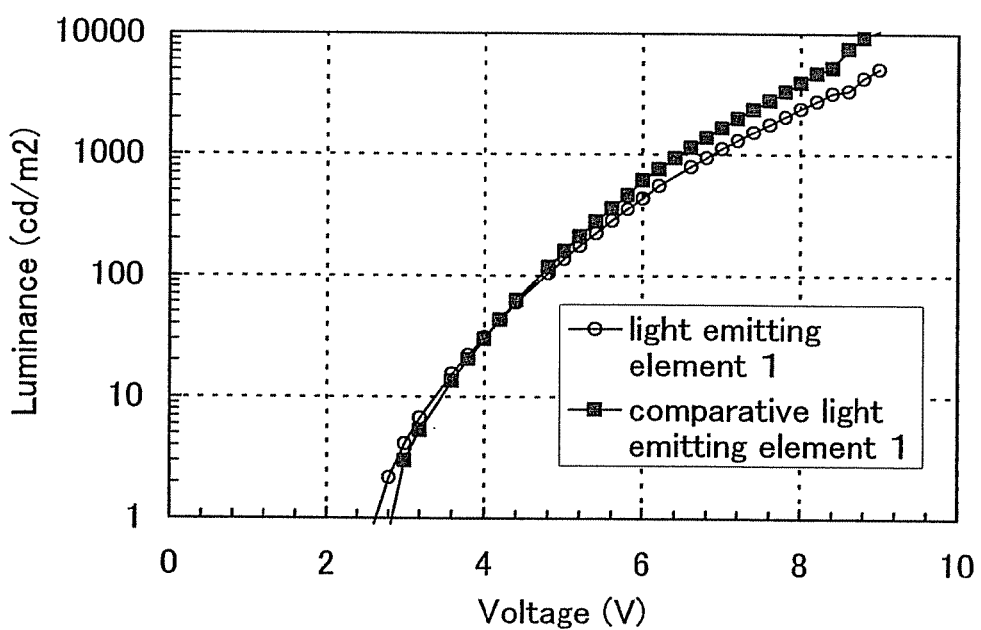
FIG. 28 is a graph showing voltage versus luminance characteristics of the light emitting element manufactured in Embodiment 3.
Figure 29:
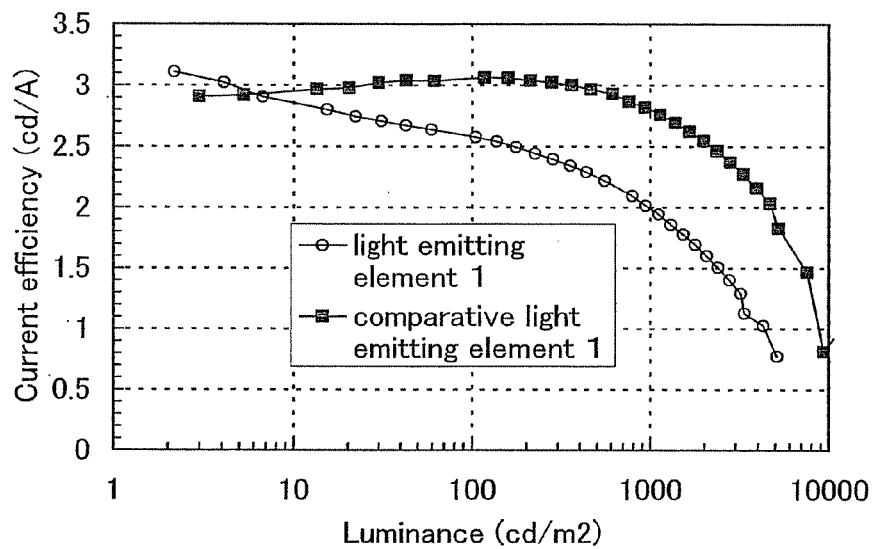
FIG. 29 is a graph showing luminance versus current efficiency characteristics of the light emitting element manufactured in Embodiment 3.
Figure 30:
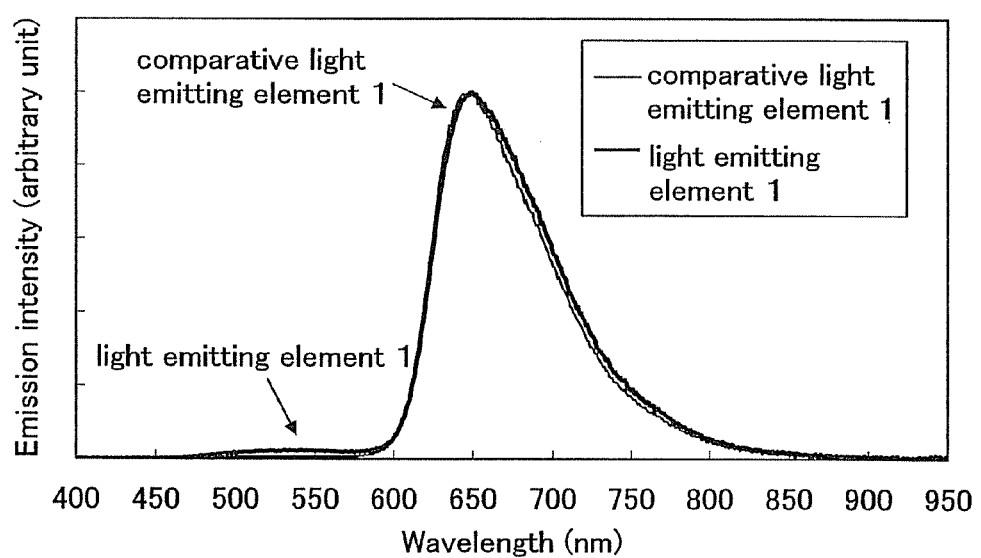
FIG. 30 is a graph showing a light emission spectrum of the light emitting element manufactured in Embodiment 3.

FIG. 27 shows current density versus luminance characteristics of Light Emitting Element 1 and Comparative Light Emitting Element 1. Further, FIG. 28 shows voltage versus luminance characteristics of the same. Further, FIG. 29 shows luminance versus current efficiency characteristics of the same. Further, FIG. 30 shows a light emission spectrum when a current of 1 mA is supplied.

A CIE chromaticity coordinate of Comparative Light emitting element at luminance of 940 cd/m$^2$ was (x=0.69, y=0.30), and light emission was red color. At the luminance of 940 cd/m$^2$, the current efficiency was 2.0 cd/A, the voltage was 6.8 V, the current density was 46.6 mA/cm$^2$, and the power efficiency was 0.931 m/W. Further, as shown in FIG. 30, the maximum emission wavelength when the current of 1 mA was supplied was 648 nm. On the other hand, a CIE chromaticity coordinate of Light Emitting Element 1 at luminance of 940 cd/m$^2$ was (x=0.67, y=0.32), and light emission was red color. At the luminance of 940 cd/m$^2$, the current efficiency was 2.8 cd/A, the voltage was 6.4 V, the current density was 33.1 mA/cm$^2$, and the power efficiency was 1.41 m/W. Further, as shown in FIG. 30, the maximum emission wavelength when the current of 1 mA was supplied was 649 nm.

As set forth above, by using the quinoxaline derivative of the present invention which is bipolar, a light emitting element in which a driving voltage is reduced can be obtained. Further, by using the quinoxaline derivative of the present invention, a light emitting element in which the light emission efficiency is high can be obtained. Further, by using the quinoxaline derivative of the present invention, a light emitting element in which the power efficiency is high, that is, the power consumption is low, can be obtained.

(Embodiment 4)

In this embodiment, the light emitting element of the present invention is described with reference to FIG. 26. A method for manufacturing a light emitting element of this embodiment is described below.

(Light Emitting Element 2)

First, indium tin oxide containing silicon oxide (ITSO) containing silicon oxide was formed over the glass substrate 2101 by sputtering to form the first electrode 2102. A thickness thereof was set to 110 nm and an electrode area was set to 2 mm×2 mm.

Next, the substrate provided with the first electrode was fixed to a substrate holder provided in a vacuum evaporation system such that a surface provided with the first electrode was placed downward. Then, after the pressure was reduced to approximately $10^{-4}$ Pa, 4,4'-bis[N-(1-napthyl)-N-phenylamino]biphenyl (abbrev.: NPB) and molybdenum (VI) oxide were co-evaporated, whereby the layer 2103 containing a composite material of an organic compound and an inorganic compound was formed. A thickness thereof was set to 50 nm and a weight ratio of NPB and molybdenum (VI) oxide was adjusted so as to be 4:1 (=NPB:molybdenum oxide). The co-evaporation method means an evaporation method by which evaporation is concurrently conducted from a plurality of evaporation sources in one treatment chamber.

Next, 4,4'-bis[N-(1-napthyl)-N-phenylamino]biphenyl (abbrev.: NPB) was deposited to have a film thickness of 10 nm by an evaporation method using resistance heating over the layer 2103 containing a composite material, whereby the hole transporting layer 2104 was formed.

Further, the light emitting layer 2105 having a thickness of 30 nm was formed over the hole transporting layer 2104 by co-evaporation of 2,3-bis[4-(9-phenylcarbazol-3-yl)phenyl] quinoxaline (abbrev.: PCPQ), which is the quinoxaline derivative of the present invention represented by the structural formula (12), and (acetylacetonato)bis[2,3-bis(4-fluorophenyl)quinoxalinato]iridium (III) (abbrev.: Ir(Fdpq)$_2$(acac)). Here, a weight ratio of PCPQ and Ir(Fdpq)$_2$(acac) was adjusted so as to be 1:0.08 (=PCPQ:Ir(Fdpq)$_2$(acac)).

After that, tris(8-quinolinolato)aluminum (abbrev.: Alq) was deposited to have a film thickness of 10 nm over the light emitting layer 2105 by an evaporation method using resistance heating, whereby the electron transporting layer 2106 was fowled.

Further, the electron injecting layer 2107 having a thickness of 50 nm was formed over the electron transporting layer 2106 by co-evaporation of tris(8-quinolinolato)aluminum (abbrev.: Alq) and lithium. Here, a weight ratio of Alq and lithium was adjusted so as to be 1:0.01 (=Alq: lithium).

Lastly, aluminum was deposited to have a film thickness of 200 nm over the electron injecting layer 2107 by an evaporation method using resistance heating, whereby the second electrode 2108 was formed. Accordingly, Light Emitting Element 2 was manufactured.

Figure 31:
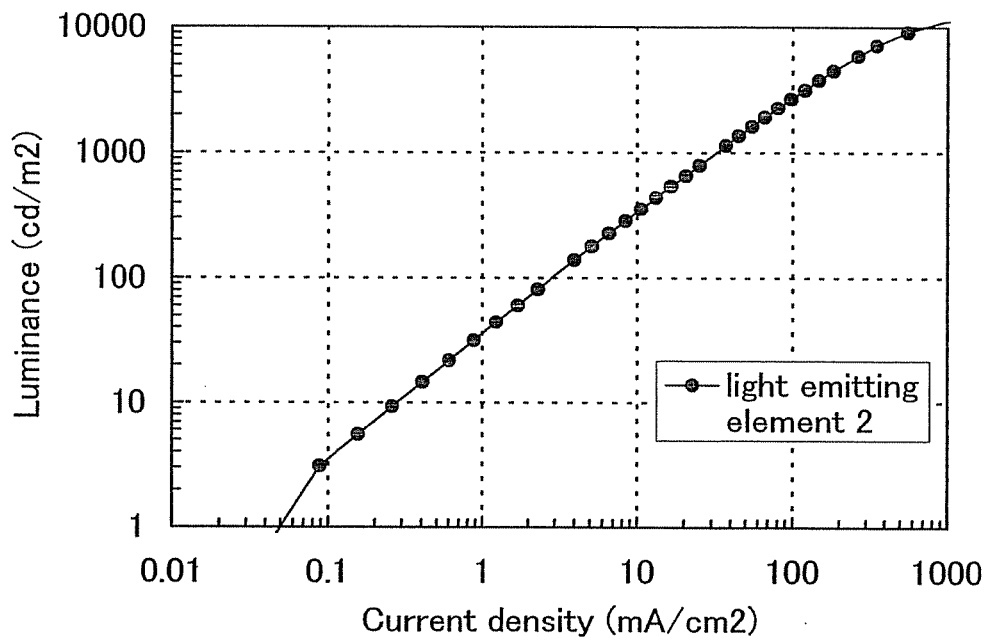
FIG. 31 is a graph showing current density versus luminance characteristics of a light emitting element manufactured in Embodiment 4.
Figure 32:
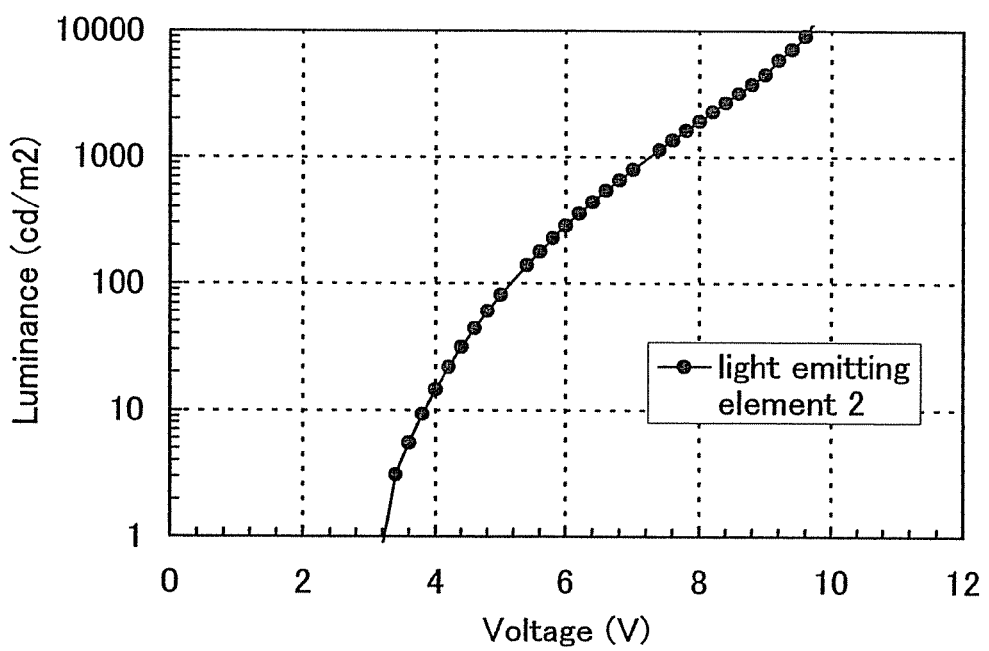
FIG. 32 is a graph showing voltage versus luminance characteristics of the light emitting element manufactured in Embodiment 4.
Figure 33:
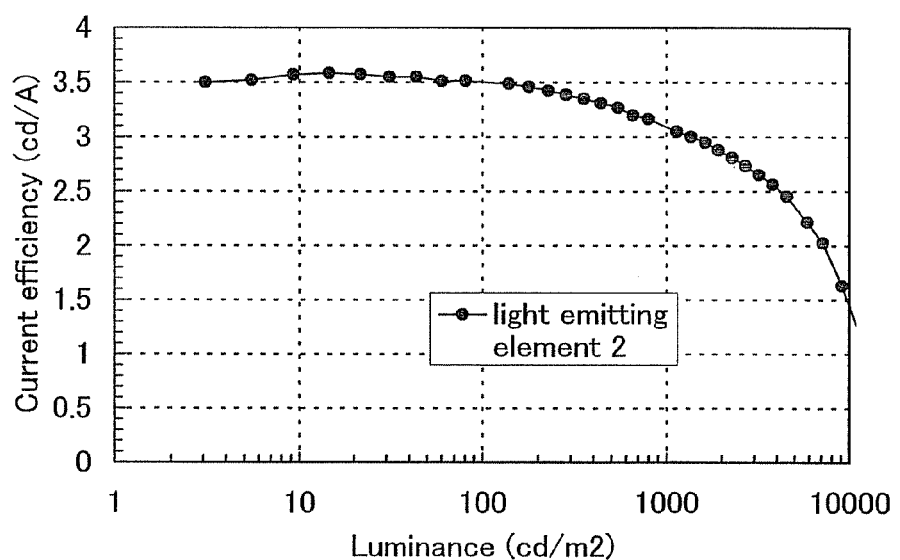
FIG. 33 is a graph showing luminance versus current efficiency characteristics of the light emitting element manufactured in Embodiment 4.
Figure 34:
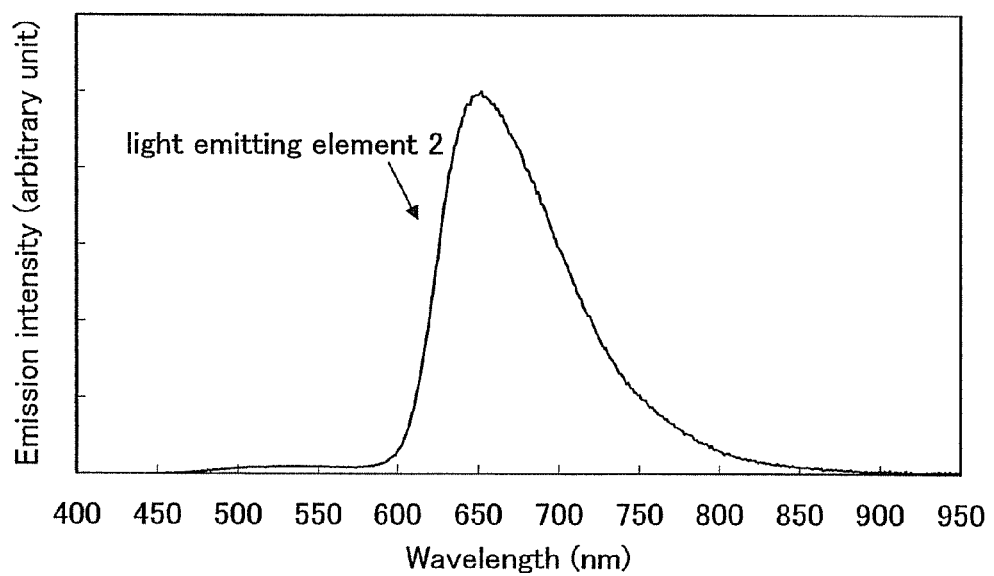
FIG. 34 is a graph showing a light emission spectrum of the light emitting element manufactured in Embodiment 4.

FIG. 31 shows current density versus luminance characteristics of Light Emitting Element 2. Further, FIG. 32 shows voltage versus luminance characteristics of the same. Further, FIG. 33 shows luminance versus current efficiency characteristics of the same. Further, FIG. 34 shows a light emission spectrum when a current of 1 mA is supplied.

A CIE chromaticity coordinate of Light Emitting Element 2 at luminance of 1100 cd/m² was (x=0.67, y=0.31), and light emission was red color. At the luminance of 1100 cd/m², the current efficiency was 3.1 cd/A, the voltage was 7.4 V, the current density was 37.2 mA/cm², and the power efficiency was 1.31 m/W. Further, the external quantum efficiency was 6.9%. Further, as shown in FIG. 34, the maximum emission wavelength when the current of 1 mA was supplied was 652 nm.

As set forth above, by using the quinoxaline derivative of the present invention which is bipolar, a light emitting element in which a driving voltage is reduced can be obtained. Further, by using the quinoxaline derivative of the present invention, a light emitting element in which the light emission efficiency is high can be obtained. Further, by using the quinoxaline derivative of the present invention, a light emitting element in which the external quantum efficiency is high can be obtained. Further, by using the quinoxaline derivative of the present invention, a light emitting element in which the power efficiency is high, that is, the power consumption is low, can be obtained.

(Embodiment 5)

In this embodiment, the light emitting element of the present invention is described with reference to FIG. 26. A method for manufacturing a light emitting element of this embodiment is described below.

(Light Emitting Element 3)

First, indium tin oxide containing silicon oxide (ITSO) containing silicon oxide was formed over the glass substrate 2101 by sputtering to form the first electrode 2102. A thickness thereof was set to 110 nm and an electrode area was set to 2 mm×2 mm.

Next, the substrate provided with the first electrode was fixed to a substrate holder provided in a vacuum evaporation system such that a surface provided with the first electrode was placed downward. Then, after the pressure was reduced to approximately 10⁻⁴ Pa, 4,4'-bis[N-(1-napthyl)-N-phenylamino]biphenyl (abbrev.: NPB) and molybdenum (VI) oxide were co-evaporated, whereby the layer 2103 containing a composite material of an organic compound and an inorganic compound was formed. A thickness thereof was set to 50 nm and a weight ratio of NPB and molybdenum (VI) oxide was adjusted so as to be 4:1 (=NPB:molybdenum oxide). The co-evaporation method means an evaporation method by which evaporation is concurrently conducted from a plurality of evaporation sources in one treatment chamber.

Next, 4,4'-bis[N-(1-napthyl)-N-phenylamino]biphenyl (abbrev.: NPB) was deposited to have a film thickness of 10 nm by an evaporation method using resistance heating over the layer 2103 containing a composite material, whereby the hole transporting layer 2104 was formed.

Further, the light emitting layer 2105 having a thickness of 30 nm was formed over the hole transporting layer 2104 by co-evaporation of 2,3-bis[4-(9-phenylcarbazol-3-yl)phenyl]quinoxaline (abbrev.: PCPQ), which is the quinoxaline derivative of the present invention represented by the structural formula (12), and (acetylacetonato)bis[2,3-bis(4-fluorophenyl)quinoxalinato]iridium (III) (abbrev.: Ir(Fdpq)₂(acac)). Here, a weight ratio of PCPQ and Ir(Fdpq)₂(acac) was adjusted so as to be 1:0.08 (=PCPQ:Ir(Fdpq)₂(acac)).

After that, 2,9-dimethyl-4,7-diphenyl-1,10-phenanthroline (bathocuproin, abbrev.: BCP) was deposited to have a film thickness of 10 nm over the light emitting layer 2105 by an evaporation method using resistance heating, whereby the electron transporting layer 2106 was formed.

Further, the electron injecting layer 2107 having a thickness of 50 nm was formed over the electron transporting layer 2106 by co-evaporation of tris(8-quinolinolato)aluminum (abbrev.: Alq) and lithium. Here, a weight ratio of Alq and lithium was adjusted so as to be 1:0.01 (=Alq: lithium).

Lastly, aluminum was deposited to have a film thickness of 200 nm over the electron injecting layer 2107 by an evaporation method using resistance heating, whereby the second electrode 2108 was formed. Accordingly, Light Emitting Element 3 was manufactured.

Figure 35:
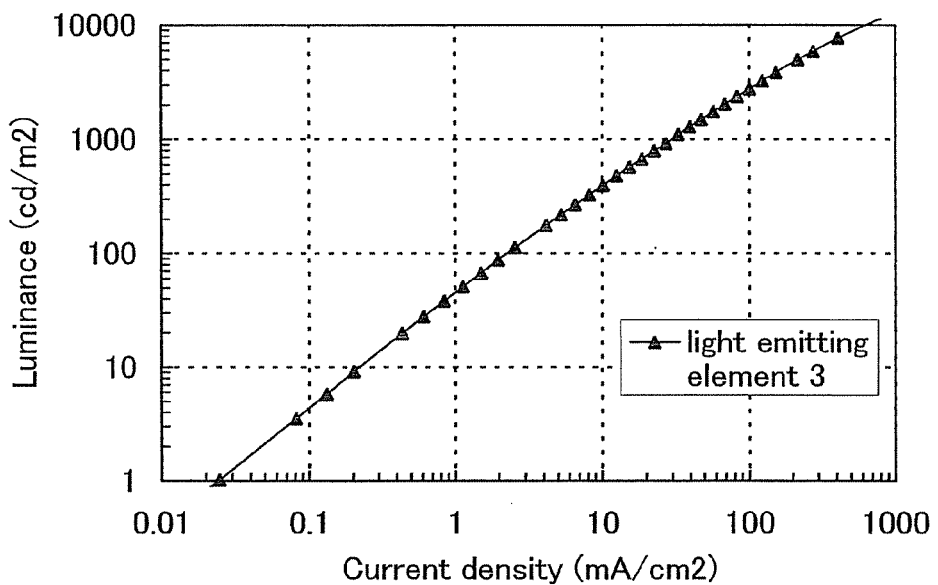
FIG. 35 is a graph showing current density versus luminance characteristics of a light emitting element manufactured in Embodiment 5.
Figure 36:
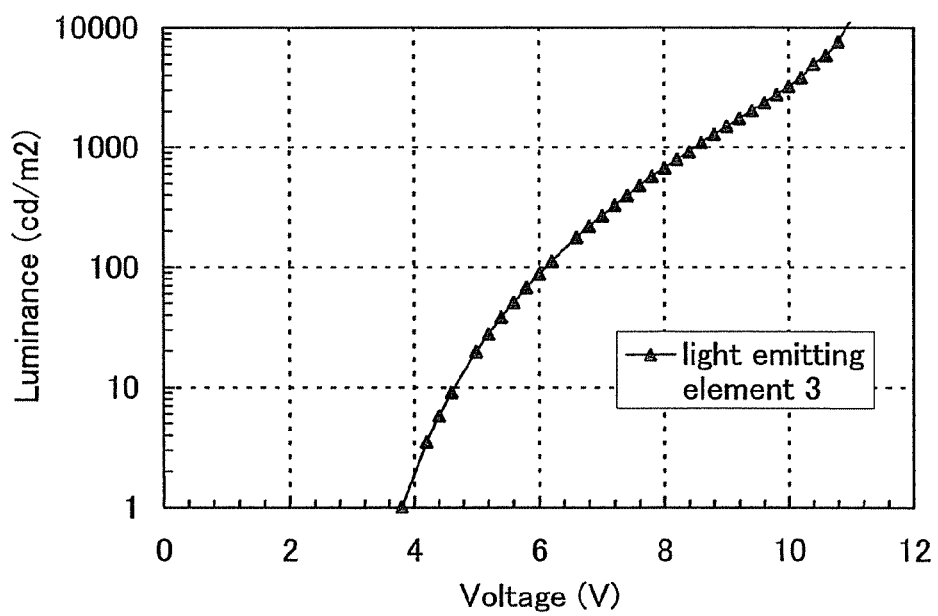
FIG. 36 is a graph showing voltage versus luminance characteristics of the light emitting element manufactured in Embodiment 5.
Figure 37:
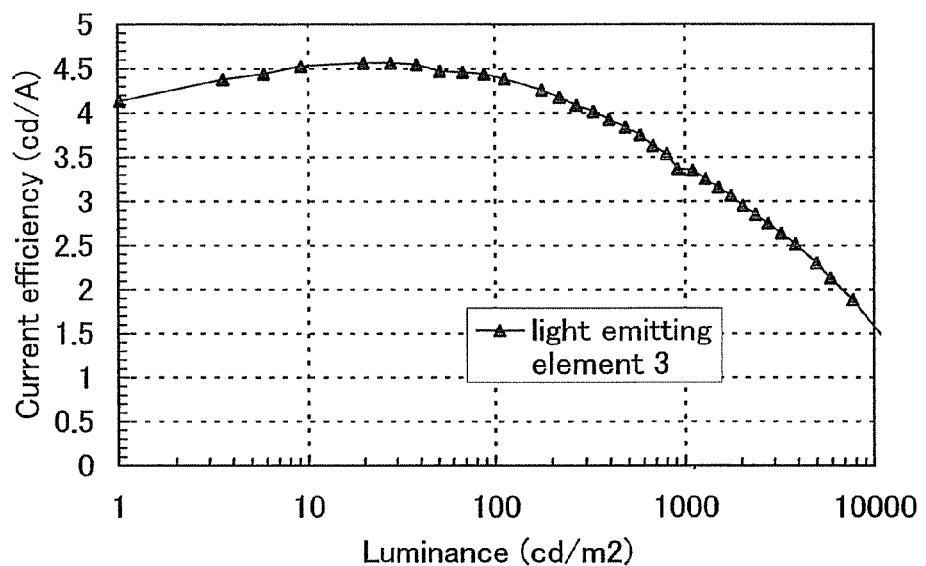
FIG. 37 is a graph showing luminance versus current efficiency characteristics of the light emitting element manufactured in Embodiment 5.
Figure 38:
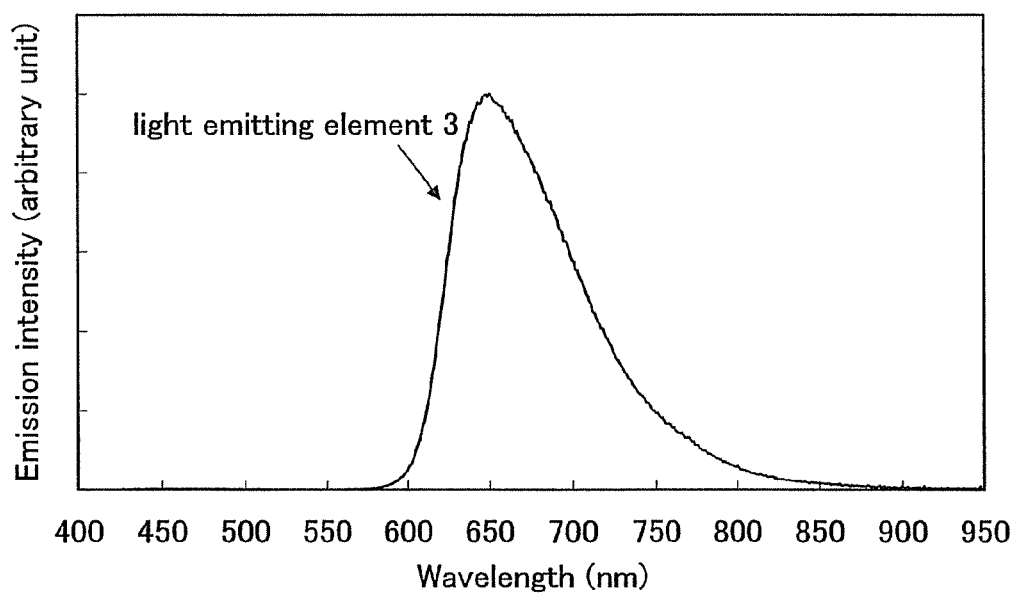
FIG. 38 is a graph showing a light emission spectrum of the light emitting element manufactured in Embodiment 5.

FIG. 35 shows current density versus luminance characteristics of Light Emitting Element 3. Further, FIG. 36 shows voltage versus luminance characteristics of the same. Further, FIG. 37 shows luminance versus current efficiency characteristics of the same. Further, FIG. 38 shows a light emission spectrum when a current of 1 mA is supplied.

A CIE chromaticity coordinate of Light Emitting Element 3 at luminance of 920 cd/m² was (x=0.71, y=0.29), and light emission was red color. At the luminance of 920 cd/m², the current efficiency was 3.4 cd/A, the voltage was 8.4 V, the current density was 27.2 mA/cm², and the power efficiency was 1.31 m/W. Further, the external quantum efficiency was 8.5%. Further, as shown in FIG. 38, the maximum emission wavelength when the current of 1 mA was supplied was 650 nm.

As set forth above, by using the quinoxaline derivative of the present invention which is bipolar and providing a hole blocking layer, a light emitting element in which the light emission efficiency is further increased can be obtained. Further, a light emitting element in which external quantum efficiency is high can be obtained. Further, a light emitting element in which the power efficiency is high, that is, the power consumption is low, can be obtained.

(Embodiment 6)

In this embodiment, an example of a synthetic example of 2,3-bis{4-[4-(carbazole-9-yl)phenyl]phenyl}quinoxaline (abbrev.: CzPPQ) which is the quinoxaline derivative of the present invention represented by the structural formula (13) is described in detail.

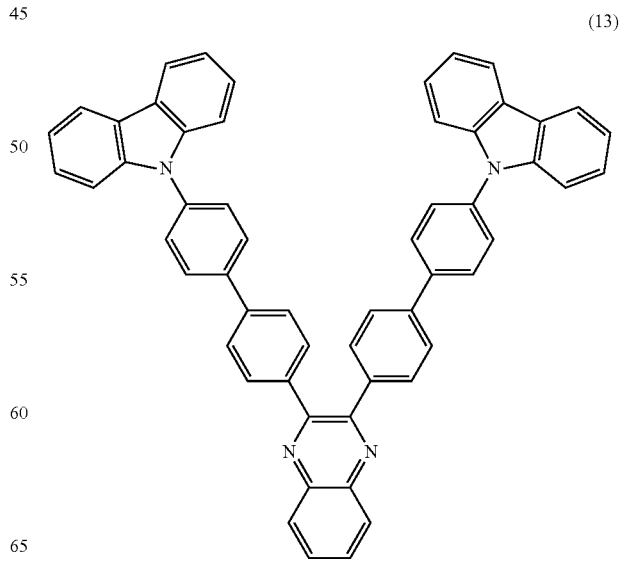

(13)

95

[Step 1] Synthesis of 2,3-bis{4-[4-(carbazole-9-yl)phenyl]phenyl}quinoxaline (abbrev.: CzPPQ)

A synthesis method of 2,3-bis-{4-[4-(carbazole-9-yl)phenyl]phenyl}quinoxaline (abbrev.: CzPPQ) is described. A synthesis scheme of 2,3-bis{4-[4-(carbazole-9-yl)phenyl]phenyl}quinoxaline (abbrev.: CzPPQ) is shown in (D-1).

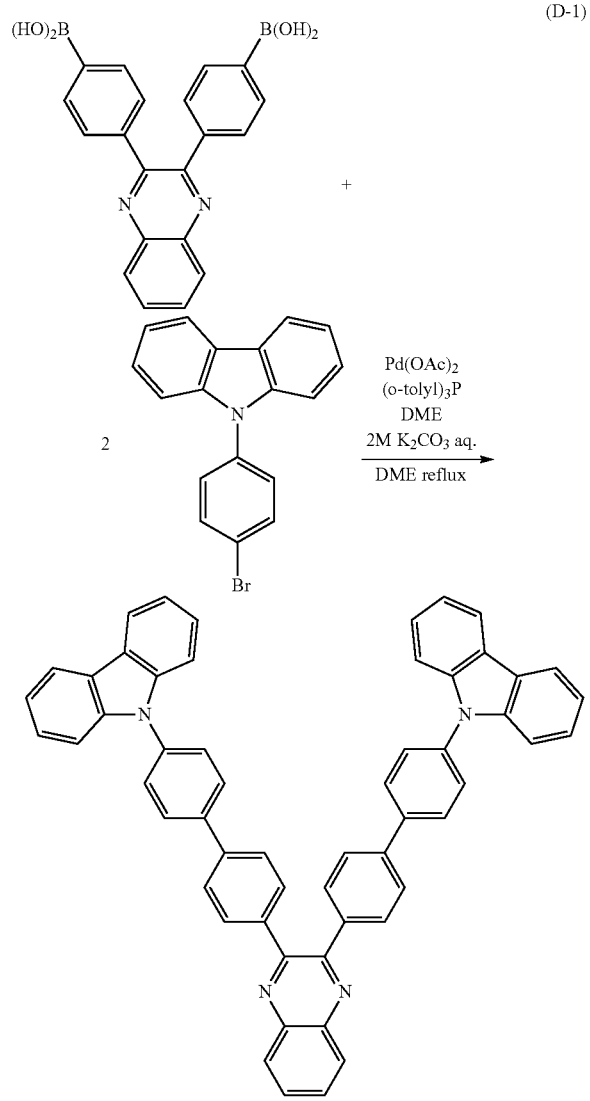

0.73 g (2.0 mmol) of the 4,4'-(quinoxaline-2,3-diyl)diphenylboronic acid synthesized in Embodiment 1, 1.28 g (4.0 mmol) of N-(4-bromophenyl)carbazole, 0.12 g (0.4 mmol) of tris(o-tolyl)phosphine, 15 mL of ethylene glycol dimethyl ether (abbrev.: DME), and 4.0 mL of 2.0 mol/L potassium carbonate solution were put into a 100-mL three-neck flask, and the flask is deaerated under reduced pressure. 0.018 g (0.08 mmol) of palladium (II) acetate was added to the mixture. A reflux of this mixture was performed for 3 hours at 80° C. in a stream of nitrogen. After the mixture was stirred and water was added thereto, a solid was deposited. The solid was recovered by suction filtration. The resulting solid was purified by sublimation purification, whereby 0.35 g of a white solid that was a subject matter was obtained at a yield of 23%. By the nuclear magnetic resonance method (NMR), it was confirmed that this compound was 2,3-bis{4-[4-(carbazole-9-yl)phenyl]phenyl}quinoxaline (abbrev.: CzPPQ).

Figure 39A:
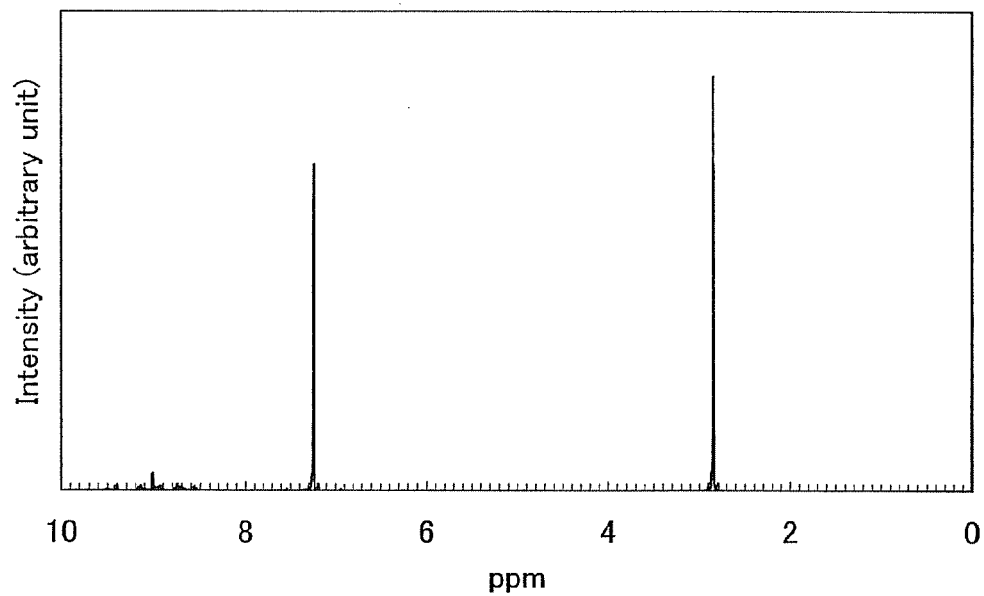
FIGS. 39A and 39B are $^1$H NMR charts of 2,3-bis{4-[4-(carbazole-9-yl)phenyl]phenyl}quinoxaline (abbrev.: CzPPQ), which is a quinoxaline derivative of the present invention.
Figure 39B:
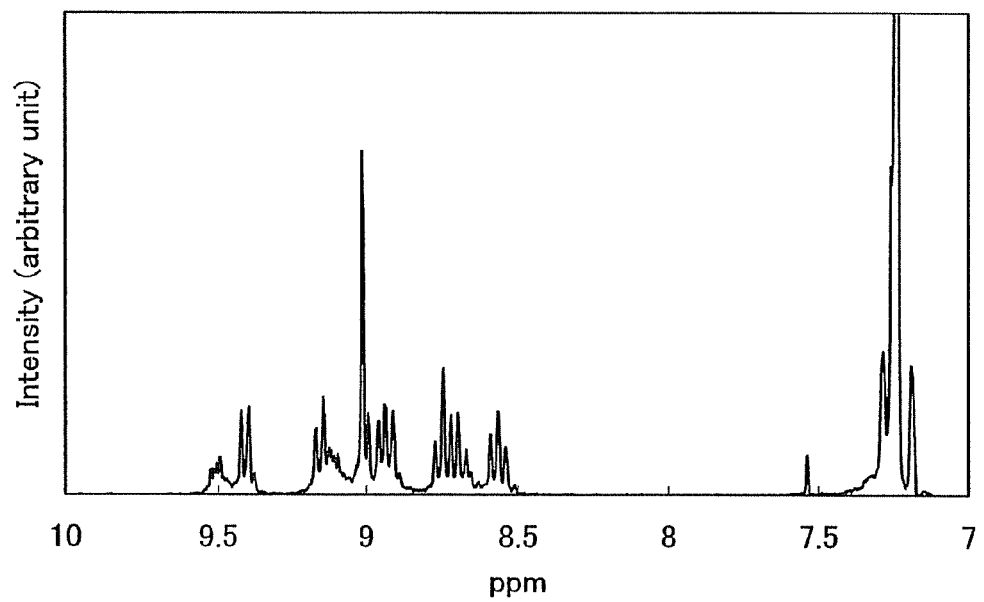

A result of proton nuclear magnetic resonance spectrometry method ($^1$H NMR) analysis of CzPPQ is as follows: $^1$H NMR (1,1,2,2-tetrachloroethane-d$_2$, 300 MHz): δ=9.52-9.49 (m, 2H), 9.42-9.38 (m, 4H), 9.17-9.15 (m, 4H), 9.13-9.10 (m, 2H), 9.01-8.89 (m, 12H), 8.78-8.66 (m, 8H), and 8.59-8.51 (m, 41-1). An $^1$H NMR chart is shown in FIGS. 39A and 39B. FIG. 39B is an enlarged chart of FIG. 39A in the range of 7.0 ppm to 10.0 ppm.

TG-DTA (Thermogravimetry-Differential Thermal Analysis) of CzPPQ was performed. For the measurement, a Thermo-Gravimetric/Differential Thermal Analyzer (TG/-DTA-320, manufactured by SII NanoTechnology Inc.) was used, and thermophysical properties were evaluated under a nitrogen atmosphere with a rising temperature of 10° C./min. Consequently, from the gravity-temperature relationship (thermogravimetric measurement), the temperature at which the gravity was 95% or less of the gravity at the starting point of the measurement was, under normal pressure, 500° C. or higher. Thus, high heat resistance was exhibited.

Figure 40:
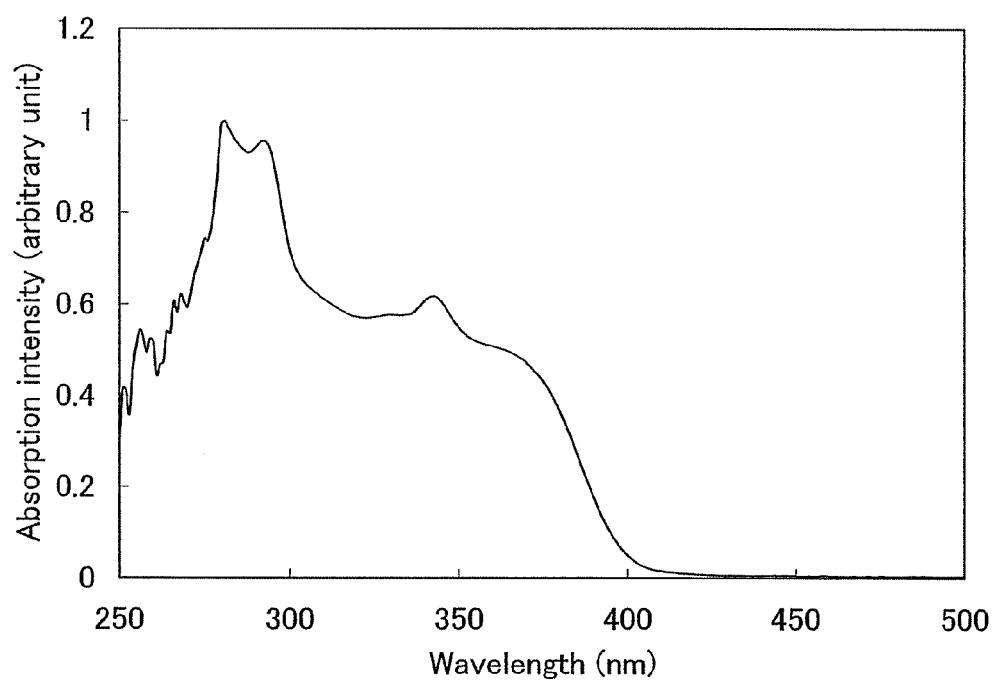
FIG. 40 is a graph showing an absorption spectrum of 2,3-bis{4-[4-(carbazole-9-yl)phenyl]phenyl}quinoxaline (abbrev.: CzPPQ), which is a quinoxaline derivative of the present invention, in a toluene solution.
Figure 41:
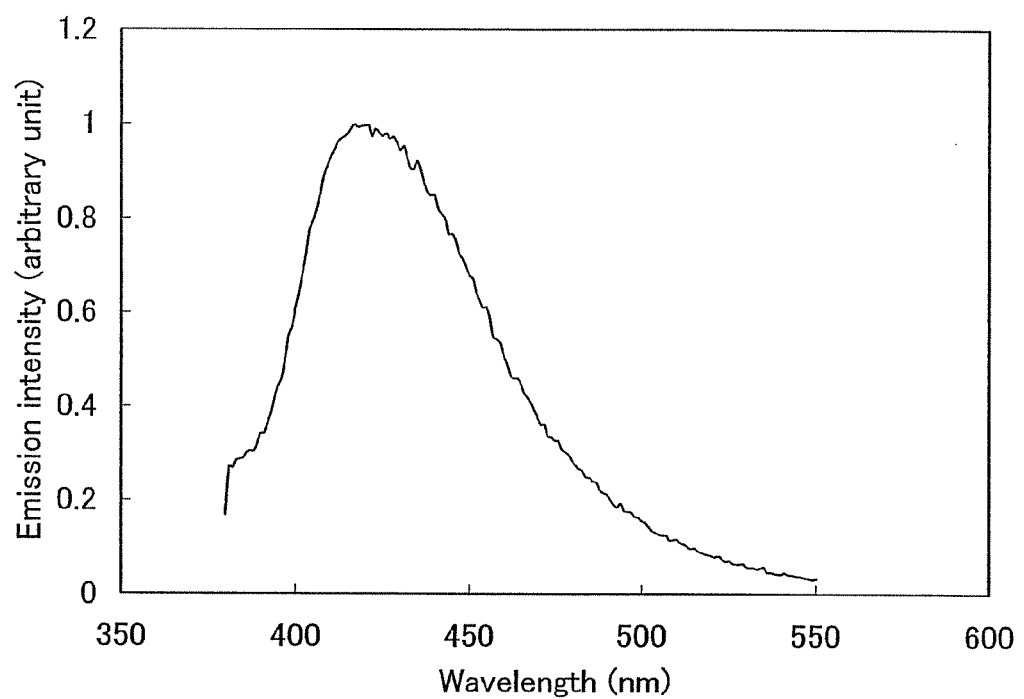
FIG. 41 is a graph showing a light emission spectrum of 2,3-bis{4-[4-(carbazole-9-yl)phenyl]phenyl}quinoxaline (abbrev.: CzPPQ), which is a quinoxaline derivative of the present invention, in a toluene solution.

Further, an absorption spectrum of toluene solution of CzPPQ is shown in FIG. 40. An ultraviolet-visible spectrophotometer (type V550, manufactured by Japan Spectroscopy Corporation) was used for the measurement. For making the sample, the solution was contained in a quartz cell, and the thin film was deposited over a quartz substrate. The absorption spectrum of the solution shown in FIG. 40 was obtained by subtracting the spectrum of the quartz. In FIG. 40, a horizontal axis indicates wavelength (nm) and a vertical axis indicates absorption intensity (unit is arbitrary). For the toluene solution, absorption was observed at around 280 nm, 290 nm, and 340 nm. Further, an emission spectrum of the toluene solution of CzPPQ (excitation wavelength: 340 nm) is shown in FIG. 41. In FIG. 41, a horizontal axis indicates wavelength (nm) and a vertical axis indicates emission intensity (unit is arbitrary). The maximum emission wavelength was 420 nm (excitation wavelength: 340 nm) for the toluene solution.

This application is based on Japanese Patent Application Serial No. 2006270084 filed in Japan Patent Office on Sep. 29, 2006, the entire contents of which are hereby incorporated by reference.

What is claimed is:

1. A light-emitting element comprising:
   a first electrode;
   a layer over the first electrode, wherein the layer comprises a light-emitting material and an organic compound; and
   a second electrode over the layer,
   wherein the organic compound comprises:
      a quinoxaline skeleton;
      a first carbazole skeleton which is substituted with a first aryl group at a 9-position of the first carbazole skeleton;
      a second carbazole skeleton which is substituted with a second aryl group at a 9-position of the second carbazole skeleton;
      a first phenylene group bonding to the quinoxaline skeleton and the first carbazole skeleton; and
      a second phenylene group bonding to the quinoxaline skeleton and the second carbazole skeleton,
   wherein an amount of the organic compound in the layer is larger than that of the light-emitting material in the layer,
   wherein one of the first phenylene group and the second phenylene group is bonded to the 2-position of the quinoxaline skeleton, and wherein the other of the first phenylene group and the second phenylene group is bonded to the 3-position of the quinoxaline skeleton.

2. The light-emitting element according to claim 1, wherein the first phenylene group is bonded to 3-position of the first carbazole skeleton, and
wherein the second phenylene group is bonded to 3-position of the second carbazole skeleton.

3. The light-emitting element according to claim 1, wherein each of the first aryl group and the second aryl group is a phenyl group.

4. A light-emitting device comprising:
a transistor; and
the light-emitting element according to claim 1, wherein the light-emitting element is electrically connected to the transistor.

5. A liquid crystal display device comprising:
a backlight unit comprising the light-emitting device according to claim 4; and
a liquid crystal layer over the backlight unit.

6. A lighting device comprising the light-emitting device according to claim 4.

7. An electronic device comprising the light-emitting device according to claim 4, wherein the electronic device is one selected from the group consisting of a camera, a goggle type display, a navigation system, an audio reproducing device, a computer, a game machine, a portable information terminal, and an image reproducing device.

8. A light-emitting element comprising:
a first electrode;
a layer over the first electrode, wherein the layer comprises a light-emitting material and an organic compound;
a second electrode over the layer,
wherein the organic compound is represented by the general formula (1):

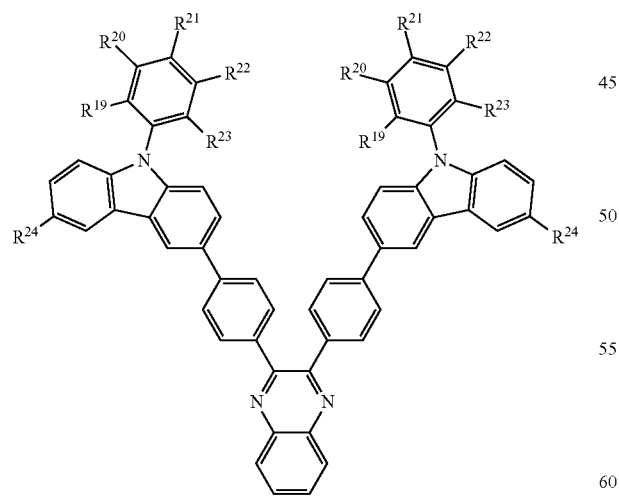

(1)

wherein $R^{19}$ to $R^{24}$ independently represent any one of a hydrogen atom, an alkyl group of carbon number 1 to 4, and an aryl group of carbon number 6 to 15, and
wherein an amount of the organic compound in the layer is larger than that of the light-emitting material in the layer.

9. A light-emitting device comprising:
a transistor; and
the light-emitting element according to claim 8, wherein the light-emitting element is electrically connected to the transistor.

10. A liquid crystal display device comprising:
a backlight unit comprising the light-emitting device according to claim 9; and
a liquid crystal layer over the backlight unit.

11. A lighting device comprising the light-emitting device according to claim 9.

12. An electronic device comprising the light-emitting device according to claim 9, wherein the electronic device is one selected from the group consisting of a camera, a goggle type display, a navigation system, an audio reproducing device, a computer, a game machine, a portable information terminal, and an image reproducing device.

13. A light-emitting element comprising:
a first electrode;
a layer over the first electrode, wherein the layer comprises a light-emitting material and an organic compound;
a second electrode over the layer,
wherein the organic compound is represented by the structural formula (2):

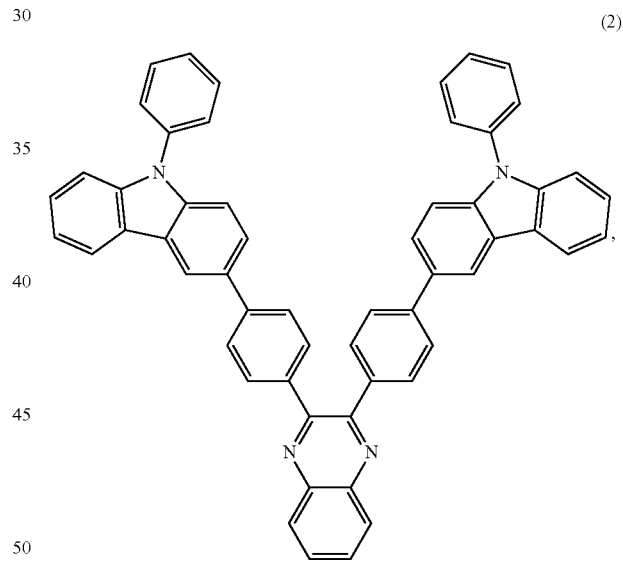

(2)

wherein an amount of the organic compound in the layer is larger than that of the light-emitting material in the layer.

14. A light-emitting device comprising:
a transistor; and
the light-emitting element according to claim 13, wherein the light-emitting element is electrically connected to the transistor.

15. A liquid crystal display device comprising:
a backlight unit comprising the light-emitting device according to claim 14; and
a liquid crystal layer over the backlight unit.

16. A lighting device comprising the light-emitting device according to claim 14.

17. An electronic device comprising the light-emitting device according to claim 14, wherein the electronic device is one selected from the group consisting of a camera, a goggle type display, a navigation system, an audio reproducing device, a computer, a game machine, a portable information terminal, and an image reproducing device.

18. The light-emitting element according to claim 1, wherein the light-emitting material is dispersed in the organic compound.

19. The light-emitting element according to claim 8, wherein the light-emitting material is dispersed in the organic compound.

20. The light-emitting element according to claim 13, wherein the light-emitting material is dispersed in the organic compound.

* * * * *

UNITED STATES PATENT AND TRADEMARK OFFICE
CERTIFICATE OF CORRECTION

PATENT NO. : 8,703,305 B2
APPLICATION NO. : 13/459981
DATED : April 22, 2014
INVENTOR(S) : Masakazu Egawa et al.

It is certified that error appears in the above-identified patent and that said Letters Patent is hereby corrected as shown below:

In the Specification:

Column 70, Line 12; Change "is; a" to --is, a--.

Column 72, Line 25 to 26; Change "staggered may" to --staggered TFT may--.

Column 74, Line 20; Change "560 ran" to --560 nm--.

Column 75, Line 67; Change "Only" to --only--.

Column 92, Line 53; Change "fowled." to --formed.--.

Column 96, Line 8; Change "(m, 41-1)." to --(m, 4H).--.

Signed and Sealed this
Sixteenth Day of September, 2014

Michelle K. Lee
*Deputy Director of the United States Patent and Trademark Office*